United States Patent
Alimi et al.

(10) Patent No.: US 11,974,573 B2
(45) Date of Patent: *May 7, 2024

(54) COMPOSITIONS, METHODS AND USES FOR CLEANING, DISINFECTING AND/OR STERILIZING

(71) Applicant: Collidion, Inc., Petaluma, CA (US)

(72) Inventors: Hojabr Alimi, Petaluma, CA (US); Sridhar Govinda Prasad, San Diego, CA (US); Surya Kanta De, San Diego, CA (US)

(73) Assignee: Collidion, Inc., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/994,847

(22) Filed: Aug. 17, 2020

(65) Prior Publication Data

US 2020/0375188 A1    Dec. 3, 2020

Related U.S. Application Data

(63) Continuation of application No. 16/540,707, filed on Aug. 14, 2019, now Pat. No. 10,750,747, which is a continuation of application No. 16/022,673, filed on Jun. 28, 2018, now Pat. No. 10,412,968, application No. 16/994,847 is a continuation of application No. 16/540,733, filed on Aug. 14, 2019, now Pat. No. 10,750,748, which is a continuation of application No. 16/022,673, filed on Jun. 28, 2018, now Pat. No. 10,412,968.

(60) Provisional application No. 62/577,225, filed on Oct. 26, 2017, provisional application No. 62/526,175, filed on Jun. 28, 2017.

(51) Int. Cl.
*A01N 47/44* (2006.01)
*A01N 31/02* (2006.01)
*A61L 2/00* (2006.01)
*A61L 2/18* (2006.01)

(52) U.S. Cl.
CPC ............. *A01N 47/44* (2013.01); *A01N 31/02* (2013.01); *A61L 2/0088* (2013.01); *A61L 2/18* (2013.01); *A61L 2202/24* (2013.01)

(58) Field of Classification Search
CPC ........ A01N 47/44; A01N 33/12; A01N 25/02; A01N 31/02; A01N 35/02; A61L 2/18; A61L 2/0088; A61L 2202/24
See application file for complete search history.

(56) References Cited

U.S. PATENT DOCUMENTS

| | | |
|---|---|---|
| 2,140,401 A | 12/1938 | Fink |
| 3,914,397 A | 10/1975 | Mueller |
| 4,190,638 A | 2/1980 | Hoekje et al. |
| 4,394,517 A | 7/1983 | Martin et al. |
| 4,670,592 A | 6/1987 | Eakin et al. |
| 4,908,215 A | 3/1990 | Perlman |
| 5,019,173 A | 5/1991 | Gettings et al. |
| 5,098,970 A | 3/1992 | Hsieh et al. |
| 5,322,677 A | 6/1994 | Shaffer et al. |
| 5,332,511 A | 7/1994 | Gay et al. |
| 5,368,749 A | 11/1994 | La |
| 5,547,662 A | 8/1996 | Khan et al. |
| 5,700,742 A | 12/1997 | Payne |
| 5,750,579 A | 5/1998 | Kamishita et al. |
| 5,885,562 A * | 3/1999 | Lowry ............... A61K 8/35 424/68 |
| 6,180,684 B1 | 1/2001 | Halmo et al. |
| 6,207,201 B1 | 3/2001 | Piacenza |
| 6,245,361 B1 | 6/2001 | Merritt |
| 6,333,054 B1 | 12/2001 | Rogozinski |
| 6,426,066 B1 | 7/2002 | Najafi et al. |
| 6,455,086 B1 | 9/2002 | Trinh et al. |
| 6,544,401 B1 | 4/2003 | Colic |

(Continued)

FOREIGN PATENT DOCUMENTS

| | | |
|---|---|---|
| EP | 0129980 B1 | 1/1989 |
| EP | 1355681 B1 | 3/2006 |

(Continued)

OTHER PUBLICATIONS

Noguchi et al. BMC Proceedings, 2011, 5 (Suppl 6): P270. (Year: 2011).*

(Continued)

*Primary Examiner* — Doan T Phan
(74) *Attorney, Agent, or Firm* — UltimatEdge IP Law Group, P.C.; Dean G. Stathakis

(57) ABSTRACT

The present specification discloses a composition comprising, consisting essentially of, or consisting of hypochlorous acid or free available chlorine and one or more disinfectants, a composition comprising, consisting essentially of, or consisting of hypochlorous acid or free available chlorine, one or more disinfectants and one or more surfactants, a composition comprising, consisting essentially of, or consisting of hypochlorous acid or free available chlorine and one or more surfactants, a composition comprising, consisting essentially of, or consisting of one or more guanide-containing compound and one or more alcohols, kits comprising, consisting essentially of, or consisting of a disclosed composition, as well as methods and uses to clean, disinfect and/or sterilize a device using such compositions, methods and uses to clean, disinfect and/or sterilize a surface area using such compositions, methods and uses to clean, disinfect and/or sterilize a microbial infection in an individual using such compositions.

20 Claims, No Drawings

(56) References Cited

U.S. PATENT DOCUMENTS

| | | | |
|---|---|---|---|
| 7,008,545 B2 | 3/2006 | Mayer | |
| 7,048,859 B1 | 5/2006 | Moffett | |
| 7,323,118 B2 | 1/2008 | Calderon | |
| 7,700,076 B2 | 4/2010 | Tamarkin et al. | |
| 7,700,530 B2 | 4/2010 | Mundschau et al. | |
| 7,718,122 B2 | 5/2010 | Smith et al. | |
| 7,884,089 B2 | 2/2011 | Gimvang | |
| 8,062,500 B2 | 11/2011 | Sumita | |
| 8,318,654 B2 | 11/2012 | Hoffman et al. | |
| 8,840,911 B2 | 9/2014 | Flugge-Berendes et al. | |
| 8,883,222 B2 | 11/2014 | Norton | |
| 8,945,630 B2 | 2/2015 | Calderon | |
| 9,072,726 B2 | 7/2015 | Alimi et al. | |
| 9,168,318 B2 | 10/2015 | Alimi | |
| 9,273,220 B2 | 3/2016 | Scheuing et al. | |
| 9,381,214 B2 | 7/2016 | Sampson et al. | |
| 9,474,768 B1 | 10/2016 | Richards et al. | |
| 9,486,479 B2 | 11/2016 | Northey | |
| 9,597,353 B2 | 3/2017 | Hoover | |
| 9,833,471 B1 | 12/2017 | Richards et al. | |
| 10,412,968 B2 | 9/2019 | Alimi et al. | |
| 2002/0022660 A1* | 2/2002 | Jampani | A61P 31/04 514/635 |
| 2003/0109411 A1* | 6/2003 | Kilkenny | A01N 47/44 510/438 |
| 2004/0003473 A1 | 1/2004 | Glenn et al. | |
| 2004/0050781 A1 | 3/2004 | Coffey et al. | |
| 2004/0214785 A1* | 10/2004 | Dees | A01N 31/16 514/37 |
| 2004/0219227 A1* | 11/2004 | Modak | A61K 8/347 424/641 |
| 2005/0139808 A1 | 6/2005 | Alimi | |
| 2005/0142157 A1 | 6/2005 | Alimi | |
| 2005/0239675 A1 | 10/2005 | Makansi | |
| 2006/0003023 A1 | 1/2006 | Williams | |
| 2006/0140998 A1 | 6/2006 | Nakanishi et al. | |
| 2006/0193789 A1 | 8/2006 | Tamarkin et al. | |
| 2006/0231505 A1 | 10/2006 | Mayer et al. | |
| 2006/0281663 A1 | 12/2006 | Asmus | |
| 2007/0217946 A1 | 9/2007 | Smith et al. | |
| 2007/0231247 A1 | 10/2007 | Bromberg et al. | |
| 2008/0014289 A1 | 1/2008 | Li | |
| 2009/0117164 A1 | 5/2009 | Toreki et al. | |
| 2009/0148342 A1 | 6/2009 | Bromberg et al. | |
| 2009/0246165 A1 | 10/2009 | Toreki et al. | |
| 2010/0028290 A1 | 2/2010 | Sokol | |
| 2011/0052506 A1 | 3/2011 | Abel et al. | |
| 2011/0135702 A1 | 6/2011 | Hoffman et al. | |
| 2012/0121679 A1 | 5/2012 | Cannon et al. | |
| 2012/0164235 A1 | 6/2012 | Northey | |
| 2012/0223022 A1 | 9/2012 | Hassler et al. | |
| 2012/0269904 A1 | 10/2012 | Northey | |
| 2012/0301528 A1 | 11/2012 | Uhlmann et al. | |
| 2013/0129648 A1 | 5/2013 | Nguyen et al. | |
| 2013/0171224 A1 | 7/2013 | Percival et al. | |
| 2013/0259955 A1 | 10/2013 | Chen et al. | |
| 2014/0115765 A1 | 5/2014 | Carpenter et al. | |
| 2015/0119245 A1 | 4/2015 | Robertson et al. | |
| 2015/0125543 A1 | 5/2015 | Croke et al. | |
| 2015/0190536 A1 | 7/2015 | Degala et al. | |
| 2015/0231173 A1 | 8/2015 | Sampson et al. | |
| 2015/0264935 A1 | 9/2015 | Chang | |
| 2015/0265666 A1 | 9/2015 | Modak et al. | |
| 2015/0297411 A1 | 10/2015 | Wang et al. | |
| 2015/0306137 A1 | 10/2015 | Alimi et al. | |
| 2015/0335544 A1 | 11/2015 | Lull et al. | |
| 2016/0024667 A1 | 1/2016 | Shanahan et al. | |
| 2016/0120183 A1 | 5/2016 | Northey | |
| 2016/0143944 A1 | 5/2016 | Panicheva et al. | |
| 2016/0166495 A1 | 6/2016 | Sarkar et al. | |
| 2016/0166497 A1 | 6/2016 | Saxena et al. | |
| 2016/0256369 A1 | 9/2016 | Dutton et al. | |
| 2016/0330969 A1 | 11/2016 | O'Connell | |
| 2017/0042800 A1 | 2/2017 | Wenzel et al. | |
| 2017/0071980 A1 | 3/2017 | Alimi | |
| 2017/0156336 A1 | 6/2017 | Joshi | |
| 2017/0202877 A1 | 7/2017 | Hoover et al. | |
| 2017/0290789 A1 | 10/2017 | Dicosmo | |
| 2019/0000086 A1 | 1/2019 | Alimi et al. | |

FOREIGN PATENT DOCUMENTS

| | | | |
|---|---|---|---|
| EP | 1874913 B1 | 7/2008 | |
| EP | 1941797 B1 | 6/2010 | |
| EP | 3028568 A1 | 6/2016 | |
| GB | 2541407 A | 2/2017 | |
| JP | 57-61099 A | 4/1982 | |
| WO | WO-0015036 A1 * | 3/2000 | ............ A01N 25/24 |
| WO | WO-2009005936 A1 * | 1/2009 | ............ G01N 31/22 |
| WO | 2013051013 A2 | 4/2013 | |
| WO | WO-2013061082 A1 * | 5/2013 | ............ A01N 25/02 |
| WO | 2013109850 A2 | 7/2013 | |
| WO | 2014147643 A2 | 9/2014 | |
| WO | 2015002932 A1 | 1/2015 | |
| WO | 2015145100 A1 | 10/2015 | |
| WO | 2016100543 A2 | 6/2016 | |
| WO | 2019006217 A1 | 1/2019 | |

OTHER PUBLICATIONS

Saraya. "Alsoft E Hyienic and Surgical Hand Disinfectant." Retrieved on Jun. 30, 2021. Retrieved online at <URL: https://services.crmservice.eu/raiminisite/Image/Download?docid=9749>; pp. 1-2. (Year: 2021).*

ECHA-EUROPA. "Polyhexamethylene biguanide." Retrieved online at <URL:https://echa.europa.eu/documents/10162/1ab 1bdf9-c012-21be-f99f-03d7fad2ab2d>; published date: Jun. 2, 2015; pp. 1-132. (Year: 2015).*

Anonymous, "Auxopan Product Label, Briotech (2016).".

Anonymous, "Hypochlorous Acid Handling, USDA Technical Evaluation Report (Aug. 13, 2015).".

Anonymous, "Preventing Cross-Contamination in Endoscope Processing: FDA Safety Communication (Nov. 19, 2009).".

Eryilmaz, et al., "Hypochlorous Acid—Analytical Methods and Antimicrobial Activity, Trop. J. Pharma. Res. 12(1):123-126 (2013).".

Hughson, et al., "Inactivation of Prions and Amyloid Seeds with Hypochlorous Acid, PLoS Pathog 12(9): e1005914 (2016).".

Kuruvilla, et al., "Antimicrobial Activity of 2.5% Sofium Hypochlorite and 0.2% Ch;orhexidine Gluconate Seperately and Combined, as Endodontic Irrigants, J. Endodon. 24(7): 472-476 (1998).".

Leung, et al., "Topical Hypochlorite Ameliorates NF-κB-Mediated Skin Diseases in Mice, J. Clin. Invest. 123(12): 5361-5370 (2013).".

Li, et al., "Synthesis and Characterization of Biocompatible Antimicrobial N-Halamine-Functionalized Titanium Dioxide Core-Shell Nanoparticles, Colloids Surf. B: Biointerfaces 148: 511-517 (2016).".

Mitchell, et al., "Evaluation of a Combination of Sodium Hypochlorite and Polyhexamethylene Biguanide as an Egg Wash for Red-Eared Slider Turtles (*Trachemys scripta elegans*) to Suppress or Eliminate *Salmonella* Organisms on Egg Surfaces and in Hatchlings, Am. J. Vet. Res. 68(".

Rutala, et al., "Guideline for Disinfection and Sterilization in Healthcare Facilities, 2008, CDC, p. 158 (2008).".

Vervier, et al., "A Multifunctional Ingredient for Next-Generation Skin Care Products, Dow Corning Europe Form No. 27-1237B-01 (Unknown Date).".

Walia, et al., "The Efficacy of Different Cleaning and Disinfection Procedures to Reduce *Salmonella* and Enterobacteriaceae in the Lairage Environment of a Pig Abattoir, Int. J. Food Microbiol. 246: 64-71 (2017).".

WIPO, "PCT Form ISA210, International Search Report for International Patent Application Serial No. PCT/US2018/040155, pp. 4 (dated Aug. 21, 2018).".

WIPO, "PCT Form ISA210, International Search Report for International Patent Application Serial No. PCT/US2018/054263, p. 4 (dated Feb. 4, 2019).".

(56) References Cited

OTHER PUBLICATIONS

WIPO, "PCT Form ISA210, International Search Report for International Patent Application Serial No. PCT/US2019/013542, pp. 4 (dated May 8, 2019).".
WIPO, "PCT Form ISA237, Written Opinion for International Patent Application Serial No. PCT/US2018/040155, pp. 9 (dated Aug. 21, 2018).".
WIPO, "PCT Form ISA237, Written Opinion for International Patent Application Serial No. PCT/US2018/054263, pp. 7 (dated Feb. 4, 2019).".
WIPO, "PCT Form ISA237, Written Opinion for International Patent Application Serial No. PCT/US2019/013542, pp. 5 (dated May 8, 2019).".
Yuan, et al., "Reaction of Silver Nanoparticles in the Disinfection Process, Chemosphere 93: 619-625 (2013).".
WIPO, PCT Form IB373, International Preliminary Report on Patentability for International Patent Application Serial No. PCT/US2018/054263, pp. 9 (dated Apr. 16, 2020).
U.S. Appl. No. 16/022,673, filed Jun. 28, 2018, US 2019/0000086, U.S. Pat. No. 10,412,968.
U.S. Appl. No. 16/151,294, filed Oct. 3, 2018, US 2019/0099336.
U.S. Appl. No. 16/247,501, filed Jan. 14, 2019, US 2019/0216090.
U.S. Appl. No. 16/540,707, filed Aug. 14, 2019, US 2019/0364900-, U.S. Pat. No. 10,750,747.
U.S. Appl. No. 16/540,733, filed Aug. 14, 2019, US 2019/0364901, U.S. Pat. No. 10,750,748.
U.S. Appl. No. 16/994,862, filed Aug. 17, 2020.

\* cited by examiner

COMPOSITIONS, METHODS AND USES FOR CLEANING, DISINFECTING AND/OR STERILIZING

This continuation application claims the benefit of priority and the filing date pursuant to 35 U.S.C. § 120 to U.S. Non-Provisional application Ser. No. 16/540,707, filed Aug. 14, 2019, a continuation application which claims priority to U.S. Non-Provisional application Ser. No. 16/022,673, filed Jun. 28, 2018, now U.S. Pat. No. 10,412,968, which claims the benefit of priority and the filing date pursuant to 35 U.S.C. § 119(e) to U.S. Provisional Patent Application 62/577,225, filed Oct. 26, 2017, and U.S. Provisional Patent Application 62/526,175, filed Jun. 28, 2017; and this continuation application claims the benefit of priority and the filing date pursuant to 35 U.S.C. § 120 to U.S. Non-Provisional application Ser. No. 16/540,737, filed Aug. 14, 2019, a continuation application which claims priority to U.S. Non-Provisional application Ser. No. 16/022,673, filed Jun. 28, 2018, now U.S. Pat. No. 10,412,968, which claims the benefit of priority and the filing date pursuant to 35 U.S.C. § 119(e) to U.S. Provisional Patent Application 62/577,225, filed Oct. 26, 2017, and U.S. Provisional Patent Application 62/526,175, filed Jun. 28, 2017, the entire content of each of which is hereby incorporated by reference in its entirety.

In the United States, approximately 46.5 million surgical procedures and even more invasive medical procedures, including approximately 5 million gastrointestinal endoscopies, are performed each year. Each procedure involves contact by a medical device with a patient's sterile tissue or mucous membranes. A major risk of all such procedures is the introduction of pathogens that can lead to infection. Failure to properly clean, disinfect and/or sterilize a medical device can expose a patient to body fluids and/or tissue contaminants from a prior patient which can result in person-to-person or environmental transmission of pathogens and infect large numbers of people.

Endoscopes are used for the diagnosis and treatment of numerous medical conditions and are part of a family of valuable diagnostic and therapeutic tools. Unfortunately, endoscopes have been traced to more healthcare-associated disease outbreaks than any other medical device. This is due primarily to the fact that endoscopes 1) acquire high levels of microbial contamination (bioburden) during use due to the types of body cavities this device is exposed to; and 2) are fundamentally difficult to clean, disinfect and/or sterilize. For example, in 2012 the source of transmission of Carbapenem-Resistant Enterobacteriaceae (CRE) "superbug" infections in patients from hospitals in Seattle, Pittsburgh and Chicago were traced to contaminated endoscopes.

Sterilization of a medical device is preferred because this process destroys or eliminates all forms of microbial life. However, the high temperature and pressures used in sterilization processes are not suitable for heat-sensitive medical device. Such heat-sensitive devices must be cleaned using a disinfection process. However, one problem associated with currently used disinfection processes is that the type and amounts of disinfectants used are destructive to the medical device. This reduces the overall life-time use of a medical device, ultimately resulting in increased medical costs due to the need to replace the medical device sooner with a new one. In addition, given the recent infectious outbreaks due to contaminated medical devices, a better disinfection method better than currently available methods is needed.

The present specification discloses disinfection compositions, methods and uses that provide superior cleaning and disinfection of a medical device including a heat-sensitive medical device and a device classified as a critical, semi-critical or noncritical item. At the same time, the disclosed disinfection compositions, methods and uses are less harsh than conventional compositions, methods and uses resulting in a longer lifetime use of a medical device

SUMMARY

Aspects of the present specification disclose a composition comprising hypochlorous acid or free available chlorine and one or more disinfectants. A disinfectant disclosed herein can be one or more compounds containing a guanide moiety or functional group, one or more aldehyde-containing compounds, or one or more organic peroxides, or any combination thereof. A disclosed guanide-containing compound includes one or more biguanide-containing compounds, one or more biguanidine-containing compounds, one or more triguanide-containing compounds, or any combination thereof. A disclosed aldehyde-containing compound includes one or more aldehydes, one or more dialdehydes, or any combination thereof.

In other aspects of the present specification disclose a composition comprising hypochlorous acid or free available chlorine, one or more disinfectants and one or more surfactants. A disinfectant disclosed herein can be one or more compounds containing a guanide moiety or functional group, one or more aldehyde-containing compounds, or one or more organic peroxides, or any combination thereof. A disclosed guanide-containing compound includes one or more biguanide-containing compounds, one or more biguanidine-containing compounds, one or more triguanide-containing compounds, or any combination thereof. A disclosed aldehyde-containing compound includes one or more aldehydes, one or more dialdehydes, or any combination thereof. A surfactant disclosed herein can be one or more ionic surfactants, one or more zwitterionic (amphoteric) surfactants or one or more non-ionic surfactants.

In other aspects, the present specification discloses a composition comprising hypochlorous acid or free available chlorine and one or more surfactants. A disinfectant disclosed herein can be one or more compounds containing a guanide moiety or functional group, one or more aldehyde-containing compounds, or one or more organic peroxides, or any combination thereof. A disclosed guanide-containing compound includes one or more biguanide-containing compounds, one or more biguanidine-containing compounds, one or more triguanide-containing compounds, or any combination thereof. A disclosed aldehyde-containing compound includes one or more aldehydes, one or more dialdehydes, or any combination thereof. A surfactant disclosed herein can be one or more ionic surfactants, one or more zwitterionic (amphoteric) surfactants or one or more non-ionic surfactants.

In other aspects, the present specification discloses a composition comprising one or more guanide-containing compound and one or more alcohols. A disclosed guanide-containing compound includes one or more biguanide-containing compounds, one or more biguanidine-containing compounds, one or more triguanide-containing compounds, or any combination thereof. A disclosed alcohol includes ethanol, methanol, isopropyl alcohol, or any combination thereof.

In other aspects, the present specification discloses a method to clean, disinfect and/or sterilize a device. The disclosed method comprising applying a composition disclosed herein to a device, wherein application of the composition cleans, disinfects and/or sterilizes the device. The disclosed method may further comprise rinsing a cleaned, disinfected and/or sterilized device with a rinse solution disclosed herein. In other aspects of the present specification disclose a composition disclosed herein for use in cleaning, disinfecting and/or sterilizing a device. In other aspects of the present specification disclose a use of a disclosed composition clean, disinfect and/or sterilize a device.

In other aspects, the present specification discloses a method to clean, disinfect and/or sterilize a surface area. The disclosed method comprising applying a composition disclosed herein to a surface area, wherein application of the composition cleans, disinfects and/or sterilizes the surface area. The disclosed method may further comprise rinsing a cleaned, disinfected and/or sterilized surface area with a rinse solution disclosed herein. In other aspects of the present specification disclose a composition disclosed herein for use in cleaning, disinfecting and/or sterilizing a surface area. In other aspects of the present specification disclose a use of a disclosed composition clean, disinfect and/or sterilize a surface area.

In other aspects, the present specification discloses a method to clean, disinfect and/or sterilize a microbial infection in an individual. The disclosed method comprising applying a composition disclosed herein to an individual, wherein application of the composition cleans, disinfects and/or sterilizes a microbial infection. In other aspects of the present specification disclose a composition disclosed herein for use in cleaning, disinfecting and/or sterilizing of a microbial infection in an individual. In other aspects of the present specification disclose a use of a disclosed composition clean, disinfect and/or sterilize of a microbial infection in an individual. In other aspects of the present specification disclose a use of a disclosed composition in the manufacture of a medicament to clean, disinfect and/or sterilize of a microbial infection in an individual.

DETAILED DESCRIPTION

Disinfection and sterilization are essential for ensuring that a medical device does not transmit infectious pathogens to an individual. During manufacturing, a medical device for human or veterinary health should be cleaned to implantable standards prior to coating and packaging. After use, a medical device should be cleaned, disinfected and/or sterilized in order to prevent the spread of nosocomial (treatment-induced) infections to a subsequent individual.

With respect cleaning, disinfecting and/or sterilization, a medical device can be classified as a critical item, semi-critical item or noncritical item. A critical item is a device that must be sterile because it can be associated with a high risk for infection since the medical device enters sterile tissue or the vascular system and any microbial contamination could transmit disease. Non-limiting examples of a medical device that is a critical item include a surgical instrument, a catheter, such as, e.g., a cardiac or urinary catheter, an implant, a heart-lung machine, and an ultrasound probe used in sterile body cavities.

A semi-critical item is a medical device that contacts a mucous membrane or non-intact skin. Although a medical device should be free from all microorganisms, a small number of bacterial spores are permissible since the mucous membrane or non-intact skin are generally resistant to infection by common bacterial spores, but susceptible to other organisms, such as bacteria, mycobacteria, and viruses. As such, a medical device classified as a semi-critical item must minimally undergo high-level disinfection using chemical disinfectants as this procedure completely eliminates all microorganisms in or on a medical device, except for small numbers of bacterial spores. Non-limiting examples of a medical device that is a semi-critical item include a respiratory therapy equipment, an anesthesia equipment, an endoscope, such as, e.g., a gastrointestinal endoscope, a bronchoscope, or a nasopharyngoscope, an arthroscope, a laparoscope, laryngoscope blade, an esophageal manometry probe, a cystoscope, a spirometer, an anorectal manometry catheter, in vitro fertilization instruments, and a diaphragm fitting ring.

A noncritical item is a medical device that contacts intact skin but not a mucous membrane. Intact skin acts as an effective barrier to most microorganisms; therefore, the sterility of items coming in contact with intact skin is "not critical." Virtually no risk has been documented for transmission of infectious agents to patients through noncritical items when they are used as noncritical items and do not contact non-intact skin and/or mucous membranes. In contrast to critical and some semi-critical items, most noncritical reusable items may be decontaminated where they are used and do not need to be transported to a central processing area. As such, a medical device classified as a noncritical item can be cleaned with a low-level disinfectant. Noncritical items can be divided into a noncritical patient care item and noncritical environmental surface. Non-limiting examples of a medical device that is a noncritical patient care item include a bedpan, a blood pressure cuff, crutches and a computer. Non-limiting examples of a non-critical environmental surface include a bed rail, a food utensil, a bedside table, furniture and floor.

A composition disclosed herein is suitable to clean, disinfect and/or sterilize a medical device. In an aspect of this embodiment, a composition disclosed herein is suitable to clean, disinfect and/or sterilize a heat-sensitive medical device. In another aspect of this embodiment, a composition disclosed herein is suitable to clean, disinfect and/or sterilize a medical device classified as a semi-critical item or non-critical item.

A composition disclosed herein may comprise hypochlorous acid. A weak acid, the chemical formula of hypochlorous acid is HOCl, while its molecular formula is written as HClO. As shown in formula I, hypochlorous acid is a simple molecule with the central oxygen atom connected to chlorine and hydrogen atoms through single bonds and has molar mass is 52.46 g/mol.

(I)

Hypochlorous acid is a colorless solution, and its exact physical properties are variable, depending on the concentration of hypochlorous in solution. Hypochlorous acid reacts with bases to form salts called hypochlorites. For example, sodium hypochlorite (NaOCl), the active ingredient in bleach, is formed by reacting hypochlorous acid with sodium hydroxide. Hypochlorous acid also readily reacts with a variety of organic molecules and biomolecules.

The hypochlorous acid solution can be produced, e.g., by dissolving chlorine in water, hydrolysis of chlorine gas, electrolysis of a salt solution or acidification of hypochloride. For example, stable hypochlorous salts, such as, e.g., alkali metal hypochlorites like sodium hypochlorite, calcium hypochlorite, potassium hypochlorite, lithium hypochlorite and magnesium hypochlorite, can be obtained by dissolving chlorine gas into an aqueous alkali metal hydroxide solution, like a sodium hydroxide solution, a calcium hydroxide solution, a potassium hydroxide solution, a lithium hydroxide solution, or a magnesium hydroxide solution, respectively. Hypochlorous acid can also be prepared by dissolving dichlorine monoxide in water. As another example, hypochlorous acid can also be produced by electrolytically treating a saline solution. In one method, an electrical current is applied to a three-compartment cell comprising a cathode chamber, an anode chamber, and a central saline solution chamber interposed between the other two chambers where each chamber is separated by a semi-permeable membrane. During electrolysis, sodium chloride (NaCl) dissociates into negatively charged chloride (Cl$^-$) and positively charged sodium (Na$^+$). At the same time, water dissociates into hydroxide (OH–) and hydrogen (H$^+$) ions are formed. The negatively charged chloride (Cl$^-$) and hydroxide (OH$^-$) ions move to the anode to lose electrons and form hypochlorous acid (HOCl) as well as hypochlorite ions (OCl$^-$) and oxygen (O$_2$) and chlorine (Cl$_2$) gases. The reductive water comprising the hypochlorous acid is then dispensed into a collection chamber for subsequent use. Methods to produce hypochlorous acid are described in, e.g., U.S. Pat. Nos. 3,914,397, 4,190,638, 4,908,215, 5,322,677, 6,426,066, 7,323,118, 8,062,500, 8,945,630, 9,168,318, and 9,486,479, each of which is hereby incorporated by reference in its entirety.

In an embodiment, a composition disclosed herein comprises an amount of hypochlorous acid that provides a desired beneficial effect to a composition disclosed herein. In aspects of this embodiment, a composition disclosed herein comprises hypochlorous acid in an amount of, e.g., about 0.00005%, about 0.00006%, about 0.00007%, about 0.000075%, about 0.00008%, about 0.00009%, about 0.0001%, about 0.0005%, about 0.001%, about 0.0015%, about 0.002%, about 0.0025%, about 0.003%, about 0.0035%, about 0.004%, about 0.0045%, about 0.005%, about 0.0055%, about 0.006%, about 0.007%, about 0.0075%, about 0.008%, about 0.009%, about 0.01%, about 0.02%, about 0.03%, about 0.04% or about 0.05% by weight of the composition. In other aspects of this embodiment, a composition disclosed herein comprises hypochlorous acid in an amount of, e.g., at least 0.00005%, at least 0.00006%, at least 0.00007%, at least 0.000075%, at least 0.00008%, at least 0.00009%, at least 0.0001%, at least 0.0005%, at least 0.001%, at least 0.0015%, at least 0.002%, at least 0.0025%, at least 0.003%, at least 0.0035%, at least 0.004%, at least 0.0045%, at least 0.005%, at least 0.0055%, at least 0.006%, at least 0.007%, at least 0.0075%, at least 0.008%, at least 0.009%, at least 0.01%, at least 0.02%, at least 0.03%, at least 0.04% or at least 0.05% by weight of the composition. In yet other aspects of this embodiment, a composition disclosed herein comprises hypochlorous acid in an amount of, e.g., at most 0.00005%, at most 0.00006%, at most 0.00007%, at most 0.000075%, at most 0.00008%, at most 0.00009%, at most 0.0001%, at most 0.0005%, at most 0.001%, at most 0.0015%, at most 0.002%, at most 0.0025%, at most 0.003%, at most 0.0035%, at most 0.004%, at most 0.0045%, at most 0.005%, at most 0.0055%, at most 0.006%, at most 0.007%, at most 0.0075%, at most 0.008%, at most 0.009%, at most 0.01%, at most 0.02%, at most 0.03%, at most 0.04 or at most 0.05% by weight of the composition. In still other aspects of this embodiment, a composition disclosed herein comprises hypochlorous acid in an amount of from, e.g., about 0.00075% to about 0.002%, about 0.00075% to about 0.003%, about 0.00075% to about 0.004%, about 0.00075% to about 0.005%, about 0.00075% to about 0.006%, about 0.00075% to about 0.007%, about 0.00075% to about 0.008%, about 0.00075% to about 0.009%, about 0.00075% to about 0.01%, about 0.001% to about 0.002%, about 0.001% to about 0.003%, about 0.001% to about 0.004%, about 0.001% to about 0.005%, about 0.001% to about 0.006%, about 0.001% to about 0.007%, about 0.001% to about 0.008%, about 0.001% to about 0.009%, about 0.001% to about 0.01%, about 0.002% to about 0.003%, about 0.002% to about 0.004%, about 0.002% to about 0.005%, about 0.002% to about 0.006%, about 0.002% to about 0.007%, about 0.002% to about 0.008%, about 0.002% to about 0.009%, or about 0.002% to about 0.01% by weight of the composition.

In other aspects of this embodiment, a composition disclosed herein comprises hypochlorous acid in an amount of, e.g., about 0.01%, about 0.02%, about 0.025%, about 0.03%, about 0.04%, about 0.05%, about 0.06%, about 0.07%, about 0.075%, about 0.08%, about 0.09%, about 0.10%, about 0.11%, about 0.12%, about 0.13%, about 0.14%, or about 0.15% by weight of the composition. In yet other aspects of this embodiment, a composition disclosed herein comprises hypochlorous acid in an amount of, e.g., at least 0.01%, at least 0.02%, at least 0.025%, at least 0.03%, at least 0.04%, at least 0.05%, at least 0.06%, at least 0.07%, at least 0.075%, at least 0.08%, at least 0.09%, at least 0.10%, at least 0.11%, at least 0.12%, at least 0.13%, at least 0.14%, or at least 0.15% by weight of the composition. In still other aspects of this embodiment, a composition disclosed herein comprises hypochlorous acid in an amount of, e.g., at most 0.01%, at most 0.02%, at most 0.025%, at most 0.03%, at most 0.04%, at most 0.05%, at most 0.06%, at most 0.07%, at most 0.075%, at most 0.08%, at most 0.09%, at most 0.10%, at most 0.11%, at most 0.12%, at most 0.13%, at most 0.14%, or at most 0.15% by weight of the composition. In still other aspects of this embodiment, a composition disclosed herein comprises hypochlorous acid in an amount of, e.g., about 0.01% to about 0.02%, about 0.01% to about 0.03%, about 0.01% to about 0.04%, about 0.01% to about 0.05%, about 0.01% to about 0.06%, about 0.01% to about 0.07%, about 0.01% to about 0.08%, about 0.01% to about 0.09%, about 0.01% to about 0.10%, about 0.01% to about 0.11%, about 0.01% to about 0.12%, about 0.01% to about 0.13%, about 0.01% to about 0.14%, about 0.01% to about 0.15%, about 0.02% to about 0.03%, about 0.02% to about 0.04%, about 0.02% to about 0.05%, about 0.02% to about 0.06%, about 0.02% to about 0.07%, about 0.02% to about 0.08%, about 0.02% to about 0.09%, about 0.02% to about 0.10%, about 0.02% to about 0.11%, about 0.02% to about 0.12%, about 0.02% to about 0.13%, about 0.02% to about 0.14%, about 0.02% to about 0.15%, about 0.03% to about 0.04%, about 0.03% to about 0.05%, about 0.03% to about 0.06%, about 0.03% to about 0.07%, about 0.03% to about 0.08%, about 0.03% to about 0.09%, about 0.03% to about 0.10%, about 0.03% to about 0.11%, about 0.03% to about 0.12%, about 0.03% to about 0.13%, about 0.03% to about 0.14%, about 0.03% to about 0.15%, about 0.04% to about 0.05%, about 0.04% to about 0.06%, about 0.04% to about 0.07%, about 0.04% to about 0.08%, about 0.04% to about 0.09%, about 0.04% to about 0.10%, about 0.04% to about 0.11%, about 0.04% to about 0.12%, about 0.04% to about 0.13%, about 0.04% to about 0.14%, about 0.04% to about 0.15%, about 0.05% to about 0.06%, about 0.05% to about 0.07%, about 0.05% to about 0.08%, about 0.05% to about 0.09%, about 0.05% to about 0.10%, about 0.05% to about 0.11%, about 0.05% to about 0.12%, about 0.05% to about 0.13%, about 0.05% to about 0.14%, about 0.05% to about 0.15%, about 0.06% to about 0.07%, about 0.06% to about 0.08%, about 0.06% to about 0.09%, about 0.06% to about 0.10%, about 0.06% to about 0.11%, about 0.06% to about 0.12%, about 0.06% to about 0.13%, about 0.06% to about 0.14%, about 0.06% to about 0.15%, about 0.07% to about 0.08%, about 0.07% to about 0.09%, about 0.07% to about 0.10%, about 0.07% to about 0.11%, about 0.07% to about 0.12%, about 0.07% to about 0.13%, about 0.07% to about 0.14%, about 0.07% to about 0.15%, about 0.08% to about 0.09%, about 0.08% to about 0.10%, about 0.08% to about 0.11%, about 0.08% to about 0.12%, about 0.08% to about 0.13%, about 0.08% to about 0.14%, about 0.08% to about 0.15%, about 0.09% to about 0.10%, about 0.09% to about 0.11%, about 0.09% to about 0.12%, about 0.09% to about 0.13%, about 0.09% to about 0.14%, about 0.09% to about 0.15%, about 0.10% to about 0.11%, about 0.10% to about 0.12%, about 0.10% to about 0.13%, about 0.10% to about 0.14%, about 0.10% to about 0.15%, about 0.11% to about 0.12%, about 0.11% to about 0.13%, about 0.11% to about 0.14%, about 0.11% to about 0.15%, about 0.12% to about 0.13%, about 0.12% to about 0.14%, about 0.12% to about 0.15%, about 0.13% to about 0.14%, about 0.13% to about 0.15%, or about 0.14% to about 0.15%, by weight of the composition.

In aspects of this embodiment, a composition disclosed herein comprises hypochlorous acid in an amount of, e.g., 0.05 ppm, 0.10 ppm, 0.15 ppm, 0.20 ppm, 0.25 ppm, 0.30 ppm, 0.35 ppm, 0.40 ppm, 0.45 ppm, 0.50 ppm, 0.55 ppm, 0.60 ppm, 0.65 ppm, 0.70 ppm, 0.75 ppm, 0.80 ppm, 0.85 ppm, 0.90 ppm, 0.95 ppm, 1 ppm, 5 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm. In other aspects of this embodiment, a composition disclosed herein comprises hypochlorous acid in an amount of, e.g., at least 0.05 ppm, at least 0.10 ppm, at least 0.20 ppm, at least 0.30 ppm, at least 0.40 ppm, at least 0.50 ppm, at least 0.60 ppm, at least 0.70 ppm, at least 0.80 ppm, at least 0.90 ppm, at least 1 ppm, at least 10 ppm, at least 20 ppm, at least 30 ppm, at least 40 ppm, at least 50 ppm, at least 60 ppm, at least 70 ppm, at least 80 ppm, at least 90 ppm, at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, at least 1,000 ppm, at least 1,025 ppm, at least 1,050 ppm, at least 1075 ppm, at least 1,100 ppm, at least 1,125 ppm, at least 1,150 ppm, at least 1,175 ppm, at least 1,200 ppm, at least 1,225 ppm, at least 1,250 ppm, at least 1,275 ppm, at least 1,300 ppm, at least 1,325 ppm, at least 1,350 ppm, at least 1,375 ppm, at least 1,400 ppm, at least 1,425 ppm, at least 1,450 ppm, at least 1,475 ppm, or at least 1,500 ppm. In yet other aspects of this embodiment, a composition disclosed herein comprises hypochlorous acid in an amount of, e.g., at most 0.05 ppm, at most 0.10 ppm, at most 0.20 ppm, at most 0.30 ppm, at most 0.40 ppm, at most 0.50 ppm, at most 0.60 ppm, at most 0.70 ppm, at most 0.80 ppm, at most 0.90 ppm, at most 1 ppm, at most 10 ppm, at most 20 ppm, at most 30 ppm, at most 40 ppm, at most 50 ppm, at most 60 ppm, at most 70 ppm, at most 80 ppm, at most 90 ppm, at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, at most 1,000 ppm, at most 1,025 ppm, at most 1,050 ppm, at most 1075 ppm, at most 1,100 ppm, at most 1,125 ppm, at most 1,150 ppm, at most 1,175 ppm, at most 1,200 ppm, at most 1,225 ppm, at most 1,250 ppm, at most 1,275 ppm, at most 1,300 ppm, at most 1,325 ppm, at most 1,350 ppm, at most 1,375 ppm, at most 1,400 ppm, at most 1,425 ppm, at most 1,450 ppm, at most 1,475 ppm, or at most 1,500 ppm.

In still other aspects of this embodiment, a composition disclosed herein comprises hypochlorous acid in an amount of from, e.g., about 0.5 ppm to about 20 ppm, about 0.5 ppm to about 25 ppm, about 0.5 ppm to about 30 ppm, about 0.5 ppm to about 35 ppm, about 0.5 ppm to about 40 ppm, about 0.5 ppm to about 45 ppm, about 0.5 ppm to about 50 ppm, about 0.5 ppm to about 55 ppm, about 0.5 ppm to about 60 ppm, about 0.5 ppm to about 65 ppm, about 0.5 ppm to about 70 ppm, about 0.5 ppm to about 75 ppm, about 0.5 ppm to about 80 ppm, about 0.5 ppm to about 85 ppm, about 0.5 ppm to about 90 ppm, about 0.5 ppm to about 95 ppm, about 0.5 ppm to about 100 ppm, about 0.75 ppm to about 20 ppm, about 0.75 ppm to about 25 ppm, about 0.75 ppm to about 30 ppm, about 0.75 ppm to about 35 ppm, about 0.75 ppm to about 40 ppm, about 0.75 ppm to about 45 ppm, about 0.75 ppm to about 50 ppm, about 0.75 ppm to about 55 ppm, about 0.75 ppm to about 60 ppm, about 0.75 ppm to about 65 ppm, about 0.75 ppm to about 70 ppm, about 0.75 ppm to about 75 ppm, about 0.75 ppm to about 80 ppm, about 0.75 ppm to about 85 ppm, about 0.75 ppm to about 90 ppm, about 0.75 ppm to about 95 ppm, about 0.75 ppm to about 100 ppm, about 1 ppm to about 20 ppm, about 1 ppm to about 25 ppm, about 1 ppm to about 30 ppm, about 1 ppm to about 35 ppm, about 1 ppm to about 40 ppm, about 1 ppm to about 45 ppm, about 1 ppm to about 50 ppm, about 1 ppm to about 55 ppm, about 1 ppm to about 60 ppm, about 1 ppm to about 65 ppm, about 1 ppm to about 70 ppm, about 1 ppm to about 75 ppm, about 1 ppm to about 80 ppm, about 1 ppm to about 85 ppm, about 1 ppm to about 90 ppm, about 1 ppm to about 95 ppm, about 1 ppm to about 100 ppm, about 5 ppm to about 20 ppm, about 5 ppm to about 25 ppm, about 5 ppm to about 30 ppm, about 5 ppm to about 35 ppm, about 5 ppm to about 40 ppm, about 5 ppm to about 45 ppm, about 5 ppm to about 50 ppm, about 5 ppm to about 55 ppm, about 5 ppm to about 60 ppm, about 5 ppm to about 65 ppm, about 5 ppm to about 70 ppm, about 5 ppm to about 75 ppm, about 5 ppm to about 80 ppm, about 5 ppm to about 85 ppm, about 5 ppm to about 90 ppm, about 5 ppm to about 95 ppm, about 5 ppm to about 100 ppm, about 10 ppm to about 20 ppm, about 10 ppm to about 25 ppm, about 10 ppm to about 30 ppm, about 10 ppm to about 35 ppm, about 10 ppm to about 40 ppm, about 10 ppm to about 45 ppm, about 10 ppm to about 50 ppm, about 10 ppm to about 55 ppm, about 10 ppm to about 60 ppm, about 10 ppm to about 65 ppm, about 10 ppm to about 70 ppm, about 10 ppm to about 75 ppm, about 10 ppm to about 80 ppm, about 10 ppm to about 85 ppm, about 10 ppm to about 90 ppm, about 10 ppm to about 95 ppm, or about 10 ppm to about 100 ppm.

In other aspects of this embodiment, a composition disclosed herein comprises hypochlorous acid in an amount of from, e.g., about 1 ppm to about 25 ppm, about 1 ppm to about 50 ppm, about 1 ppm to about 75 ppm, about 1 ppm to about 100 ppm, about 1 ppm to about 125 ppm, about 1 ppm to about 150 ppm, about 1 ppm to about 175 ppm, about 1 ppm to about 200 ppm, about 1 ppm to about 225 ppm, about 1 ppm to about 250 ppm, about 1 ppm to about 275 ppm, about 1 ppm to about 300 ppm, about 1 ppm to about 325 ppm, about 1 ppm to about 350 ppm, about 1 ppm to about 375 ppm, about 1 ppm to about 400 ppm, about 10 ppm to about 25 ppm, about 10 ppm to about 50 ppm, about 10 ppm to about 75 ppm, about 10 ppm to about 100 ppm, about 10 ppm to about 125 ppm, about 10 ppm to about 150 ppm, about 10 ppm to about 175 ppm, about 10 ppm to about 200 ppm, about 10 ppm to about 225 ppm, about 10 ppm to about 250 ppm, about 10 ppm to about 275 ppm, about 10 ppm to about 300 ppm, about 10 ppm to about 325 ppm, about 10 ppm to about 350 ppm, about 10 ppm to about 375 ppm, about 10 ppm to about 400 ppm, about 25 ppm to about 50 ppm, about 25 ppm to about 75 ppm, about 25 ppm to about 100 ppm, about 25 ppm to about 125 ppm, about 25 ppm to about 150 ppm, about 25 ppm to about 175 ppm, about 25 ppm to about 200 ppm, about 25 ppm to about 225 ppm, about 25 ppm to about 250 ppm, about 25 ppm to about 275 ppm, about 25 ppm to about 300 ppm, about 25 ppm to about 325 ppm, about 25 ppm to about 350 ppm, about 25 ppm to about 375 ppm, about 25 ppm to about 400 ppm, about 50 ppm to about 75 ppm, about 50 ppm to about 100 ppm, about 50 ppm to about 125 ppm, about 50 ppm to about 150 ppm, about 50 ppm to about 175 ppm, about 50 ppm to about 200 ppm, about 50 ppm to about 225 ppm, about 50 ppm to about 250 ppm, about 50 ppm to about 275 ppm, about 50 ppm to about 300 ppm, about 50 ppm to about 325 ppm, about 50 ppm to about 350 ppm, about 50 ppm to about 375 ppm, about 50 ppm to about 400 ppm, about 75 ppm to about 100 ppm, about 75 ppm to about 125 ppm, about 75 ppm to about 150 ppm, about 75 ppm to about 175 ppm, about 75 ppm to about 200 ppm, about 75 ppm to about 225 ppm, about 75 ppm to about 250 ppm, about 75 ppm to about 275 ppm, about 75 ppm to about 300 ppm, about 75 ppm to about 325 ppm, about 75 ppm to about 350 ppm, about 75 ppm to about 375 ppm, about 75 ppm to about 400 ppm, about 100 ppm to about 125 ppm, about 100 ppm to about 150 ppm, about 100 ppm to about 175 ppm, about 100 ppm to about 200 ppm, about 100 ppm to about 225 ppm, about 100 ppm to about 250 ppm, about 100 ppm to about 275 ppm, about 100 ppm to about 300 ppm, about 100 ppm to about 325 ppm, about 100 ppm to about 350 ppm, about 100 ppm to about 375 ppm, about 100 ppm to about 400 ppm, about 150 ppm to about 175 ppm, about 150 ppm to about 200 ppm, about 150 ppm to about 225 ppm, about 150 ppm to about 250 ppm, about 150 ppm to about 275 ppm, about 150 ppm to about 300 ppm, about 150 ppm to about 325 ppm, about 150 ppm to about 350 ppm, about 150 ppm to about 375 ppm, about 150 ppm to about 400 ppm, about 200 ppm to about 225 ppm, about 200 ppm to about 250 ppm, about 200 ppm to about 275 ppm, about 200 ppm to about 300 ppm, about 200 ppm to about 325 ppm, about 200 ppm to about 350 ppm, about 200 ppm to about 375 ppm, about 200 ppm to about 400 ppm, about 250 ppm to about 275 ppm, about 250 ppm to about 300 ppm, about 250 ppm to about 325 ppm, about 250 ppm to about 350 ppm, about 250 ppm to about 375 ppm, about 250 ppm to about 400 ppm, about 300 ppm to about 325 ppm, about 300 ppm to about 350 ppm, about 300 ppm to about 375 ppm, about 300 ppm to about 400 ppm, about 350 ppm to about 375 ppm, about 350 ppm to about 400 ppm, or about 375 ppm to about 400 ppm.

In other aspects of this embodiment, a composition disclosed herein comprises hypochlorous acid in an amount of, e.g., about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 400 ppm to about 1,100 ppm, about 400 ppm to about 1,200 ppm, about 400 ppm to about 1,300 ppm, about 400 ppm to about 1,400 ppm, about 400 ppm to about 1,500 ppm, about 500 ppm to about 600 ppm, about 500 ppm to about 700 ppm, about 500 ppm to about 800 ppm, about 500 ppm to about 900 ppm, about 500 ppm to about 1,000 ppm, about 500 ppm to about 1,100 ppm, about 500 ppm to about 1,200 ppm, about 500 ppm to about 1,300 ppm, about 500 ppm to about 1,400 ppm, about 500 ppm to about 1,500 ppm, about 600 ppm to about 700 ppm, about 600 ppm to about 800 ppm, about 600 ppm to about 900 ppm, about 600 ppm to about 1,000 ppm, about 600 ppm to about 1,100 ppm, about 600 ppm to about 1,200 ppm, about 600 ppm to about 1,300 ppm, about 600 ppm to about 1,400 ppm, about 600 ppm to about 1,500 ppm, about 700 ppm to about 800 ppm, about 700 ppm to about 900 ppm, about 700 ppm to about 1,000 ppm, about 700 ppm to about 1,100 ppm, about 700 ppm to about 1,200 ppm, about 700 ppm to about 1,300 ppm, about 700 ppm to about 1,400 ppm, about 700 ppm to about 1,500 ppm, about 800 ppm to about 900 ppm, about 800 ppm to about 1,000 ppm, about 800 ppm to about 1,100 ppm, about 800 ppm to about 1,200 ppm, about 800 ppm to about 1,300 ppm, about 800 ppm to about 1,400 ppm, about 800 ppm to about 1,500 ppm, about 900 ppm to about 1,000 ppm, about 900 ppm to about 1,100 ppm, about 900 ppm to about 1,200 ppm, about 900 ppm to about 1,300 ppm, about 900 ppm to about 1,400 ppm, about 900 ppm to about 1,500 ppm, about 1,000 ppm to about 1,100 ppm, about 1,000 ppm to about 1,200 ppm, about 1,000 ppm to about 1,300 ppm, about 1,000 ppm to about 1,400 ppm, about 1,000 ppm to about 1,500 ppm, about 1,100 ppm to about 1,200 ppm, about 1,100 ppm to about 1,300 ppm, about 1,100 ppm to about 1,400 ppm, about 1,100 ppm to about 1,500 ppm, about 1,200 ppm to about 1,300 ppm, about 1,200 ppm to about 1,400 ppm, about 1,200 ppm to about 1,500 ppm, about 1,300 ppm to about 1,400 ppm, about 1,300 ppm to about 1,500 ppm, or about 1,400 ppm to about 1,500 ppm.

The concentration of hypochlorous acid in solution may be described as free available chlorine in parts per million. Hypochlorous acid is in equilibrium with hypochlorite ions (OCl$^-$) and dissolved chlorine gas (Cl$_2$). The extent of the equilibrium is determined predominately by the pH of the solution. Temperature also impacts the ratio of the free chlorine component. Therefore, both FAC and pH need to be known to understand the amount of chlorine present as hypochlorous acid. In general, when the pH range is about 4.0 to about 5.6, approximately 100% of the available chlorine is present as HOCl. As the pH is lowered below about 4, there is an increase in dissolved chlorine gas (Cl$_2$). Thus, at a pH of about 3, about 90% of the available chlorine is present as hypochlorous acid, at a pH of about 2, about 75% of the available chlorine is present as hypochlorous acid, at a pH of about 1.5, about 50% of the available chlorine is present as hypochlorous acid, while at a pH of about 1, about 25% of the available chlorine is present as hypochlorous acid. As the pH is increase above about 5.6, there is an increase in hypochlorite ions (OCl⁻). Thus, at a pH a pH of about 6.5, about 90% of the available chlorine is present as hypochlorous acid, at a pH of about 7, about 75% of the available chlorine is present as hypochlorous acid, at a pH of about 7.5, about 50% of the available chlorine is present as hypochlorous acid, while at a pH of about 8, about 25% of the available chlorine is present as hypochlorous acid.

The chlorine amount may be measured by methods known in the art, such as the DPD colorimeter method (Lamotte Company, Chestertown, Md.) or other known methods established by the Environmental Protection Agency. In the DPD colorimeter method, a yellow color is formed by the reaction of free chlorine With N,N-diethyl-p-phenylenediamine (DPD) and the intensity is measured With a calibrated calorimeter that provides the output in parts per million. Further addition of potassium iodide turns the solution a pink color to provide the total chlorine value.

In aspects of this embodiment, a composition disclosed herein comprises free available chlorine in an amount of, e.g., 0.05 ppm, 0.10 ppm, 0.15 ppm, 0.20 ppm, 0.25 ppm, 0.30 ppm, 0.35 ppm, 0.40 ppm, 0.45 ppm, 0.50 ppm, 0.55 ppm, 0.60 ppm, 0.65 ppm, 0.70 ppm, 0.75 ppm, 0.80 ppm, 0.85 ppm, 0.90 ppm, 0.95 ppm, 1 ppm, 5 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm. In other aspects of this embodiment, a composition disclosed herein comprises free available chlorine in an amount of, e.g., at least 0.05 ppm, at least 0.10 ppm, at least 0.20 ppm, at least 0.30 ppm, at least 0.40 ppm, at least 0.50 ppm, at least 0.60 ppm, at least 0.70 ppm, at least 0.80 ppm, at least 0.90 ppm, at least 1 ppm, at least 10 ppm, at least 20 ppm, at least 30 ppm, at least 40 ppm, at least 50 ppm, at least 60 ppm, at least 70 ppm, at least 80 ppm, at least 90 ppm, at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, at least 1,000 ppm, at least 1,025 ppm, at least 1,050 ppm, at least 1075 ppm, at least 1,100 ppm, at least 1,125 ppm, at least 1,150 ppm, at least 1,175 ppm, at least 1,200 ppm, at least 1,225 ppm, at least 1,250 ppm, at least 1,275 ppm, at least 1,300 ppm, at least 1,325 ppm, at least 1,350 ppm, at least 1,375 ppm, at least 1,400 ppm, at least 1,425 ppm, at least 1,450 ppm, at least 1,475 ppm, or at least 1,500 ppm. In yet other aspects of this embodiment, a composition disclosed herein comprises free available chlorine in an amount of, e.g., at most 0.05 ppm, at most 0.10 ppm, at most 0.20 ppm, at most 0.30 ppm, at most 0.40 ppm, at most 0.50 ppm, at most 0.60 ppm, at most 0.70 ppm, at most 0.80 ppm, at most 0.90 ppm, at most 1 ppm, at most 10 ppm, at most 20 ppm, at most 30 ppm, at most 40 ppm, at most 50 ppm, at most 60 ppm, at most 70 ppm, at most 80 ppm, at most 90 ppm, at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, at most 1,000 ppm, at most 1,025 ppm, at most 1,050 ppm, at most 1075 ppm, at most 1,100 ppm, at most 1,125 ppm, at most 1,150 ppm, at most 1,175 ppm, at most 1,200 ppm, at most 1,225 ppm, at most 1,250 ppm, at most 1,275 ppm, at most 1,300 ppm, at most 1,325 ppm, at most 1,350 ppm, at most 1,375 ppm, at most 1,400 ppm, at most 1,425 ppm, at most 1,450 ppm, at most 1,475 ppm, or at most 1,500 ppm.

In still other aspects of this embodiment, a composition disclosed herein comprises free available chlorine in an amount of from, e.g., about 0.5 ppm to about 20 ppm, about 0.5 ppm to about 25 ppm, about 0.5 ppm to about 30 ppm, about 0.5 ppm to about 35 ppm, about 0.5 ppm to about 40 ppm, about 0.5 ppm to about 45 ppm, about 0.5 ppm to about 50 ppm, about 0.5 ppm to about 55 ppm, about 0.5 ppm to about 60 ppm, about 0.5 ppm to about 65 ppm, about 0.5 ppm to about 70 ppm, about 0.5 ppm to about 75 ppm, about 0.5 ppm to about 80 ppm, about 0.5 ppm to about 85 ppm, about 0.5 ppm to about 90 ppm, about 0.5 ppm to about 95 ppm, about 0.5 ppm to about 100 ppm, about 0.75 ppm to about 20 ppm, about 0.75 ppm to about 25 ppm, about 0.75 ppm to about 30 ppm, about 0.75 ppm to about 35 ppm, about 0.75 ppm to about 40 ppm, about 0.75 ppm to about 45 ppm, about 0.75 ppm to about 50 ppm, about 0.75 ppm to about 55 ppm, about 0.75 ppm to about 60 ppm, about 0.75 ppm to about 65 ppm, about 0.75 ppm to about 70 ppm, about 0.75 ppm to about 75 ppm, about 0.75 ppm to about 80 ppm, about 0.75 ppm to about 85 ppm, about 0.75 ppm to about 90 ppm, about 0.75 ppm to about 95 ppm, about 0.75 ppm to about 100 ppm, about 1 ppm to about 20 ppm, about 1 ppm to about 25 ppm, about 1 ppm to about 30 ppm, about 1 ppm to about 35 ppm, about 1 ppm to about 40 ppm, about 1 ppm to about 45 ppm, about 1 ppm to about 50 ppm, about 1 ppm to about 55 ppm, about 1 ppm to about 60 ppm, about 1 ppm to about 65 ppm, about 1 ppm to about 70 ppm, about 1 ppm to about 75 ppm, about 1 ppm to about 80 ppm, about 1 ppm to about 85 ppm, about 1 ppm to about 90 ppm, about 1 ppm to about 95 ppm, about 1 ppm to about 100 ppm, about 5 ppm to about 20 ppm, about 5 ppm to about 25 ppm, about 5 ppm to about 30 ppm, about 5 ppm to about 35 ppm, about 5 ppm to about 40 ppm, about 5 ppm to about 45 ppm, about 5 ppm to about 50 ppm, about 5 ppm to about 55 ppm, about 5 ppm to about 60 ppm, about 5 ppm to about 65 ppm, about 5 ppm to about 70 ppm, about 5 ppm to about 75 ppm, about 5 ppm to about 80 ppm, about 5 ppm to about 85 ppm, about 5 ppm to about 90 ppm, about 5 ppm to about 95 ppm, about 5 ppm to about 100 ppm, about 10 ppm to about 20 ppm, about 10 ppm to about 25 ppm, about 10 ppm to about 30 ppm, about 10 ppm to about 35 ppm, about 10 ppm to about 40 ppm, about 10 ppm to about 45 ppm, about 10 ppm to about 50 ppm, about 10 ppm to about 55 ppm, about 10 ppm to about 60 ppm, about 10 ppm to about 65 ppm, about 10 ppm to about 70 ppm, about 10 ppm to about 75 ppm, about 10 ppm to about 80 ppm, about 10 ppm to about 85 ppm, about 10 ppm to about 90 ppm, about 10 ppm to about 95 ppm, or about 10 ppm to about 100 ppm.

In other aspects of this embodiment, a composition disclosed herein comprises free available chlorine in an amount of from, e.g., about 1 ppm to about 25 ppm, about 1 ppm to about 50 ppm, about 1 ppm to about 75 ppm, about 1 ppm to about 100 ppm, about 1 ppm to about 125 ppm, about 1 ppm to about 150 ppm, about 1 ppm to about 175 ppm, about 1 ppm to about 200 ppm, about 1 ppm to about 225 ppm, about 1 ppm to about 250 ppm, about 1 ppm to about 275 ppm, about 1 ppm to about 300 ppm, about 1 ppm to about 325 ppm, about 1 ppm to about 350 ppm, about 1 ppm to about 375 ppm, about 1 ppm to about 400 ppm, about 10 ppm to about 25 ppm, about 10 ppm to about 50 ppm, about 10 ppm to about 75 ppm, about 10 ppm to about 100 ppm, about 10 ppm to about 125 ppm, about 10 ppm to about 150 ppm, about 10 ppm to about 175 ppm, about 10 ppm to about 200 ppm, about 10 ppm to about 225 ppm, about 10 ppm to about 250 ppm, about 10 ppm to about 275 ppm, about 10 ppm to about 300 ppm, about 10 ppm to about 325 ppm, about 10 ppm to about 350 ppm, about 10 ppm to about 375 ppm, about 10 ppm to about 400 ppm, about 25 ppm to about 50 ppm, about 25 ppm to about 75 ppm, about 25 ppm to about 100 ppm, about 25 ppm to about 125 ppm, about 25 ppm to about 150 ppm, about 25 ppm to about 175 ppm, about 25 ppm to about 200 ppm, about 25 ppm to about 225 ppm, about 25 ppm to about 250 ppm, about 25 ppm to about 275 ppm, about 25 ppm to about 300 ppm, about 25 ppm to about 325 ppm, about 25 ppm to about 350 ppm, about 25 ppm to about 375 ppm, about 25 ppm to about 400 ppm, about 50 ppm to about 75 ppm, about 50 ppm to about 100 ppm, about 50 ppm to about 125 ppm, about 50 ppm to about 150 ppm, about 50 ppm to about 175 ppm, about 50 ppm to about 200 ppm, about 50 ppm to about 225 ppm, about 50 ppm to about 250 ppm, about 50 ppm to about 275 ppm, about 50 ppm to about 300 ppm, about 50 ppm to about 325 ppm, about 50 ppm to about 350 ppm, about 50 ppm to about 375 ppm, about 50 ppm to about 400 ppm, about 75 ppm to about 100 ppm, about 75 ppm to about 125 ppm, about 75 ppm to about 150 ppm, about 75 ppm to about 175 ppm, about 75 ppm to about 200 ppm, about 75 ppm to about 225 ppm, about 75 ppm to about 250 ppm, about 75 ppm to about 275 ppm, about 75 ppm to about 300 ppm, about 75 ppm to about 325 ppm, about 75 ppm to about 350 ppm, about 75 ppm to about 375 ppm, about 75 ppm to about 400 ppm, about 100 ppm to about 125 ppm, about 100 ppm to about 150 ppm, about 100 ppm to about 175 ppm, about 100 ppm to about 200 ppm, about 100 ppm to about 225 ppm, about 100 ppm to about 250 ppm, about 100 ppm to about 275 ppm, about 100 ppm to about 300 ppm, about 100 ppm to about 325 ppm, about 100 ppm to about 350 ppm, about 100 ppm to about 375 ppm, about 100 ppm to about 400 ppm, about 150 ppm to about 175 ppm, about 150 ppm to about 200 ppm, about 150 ppm to about 225 ppm, about 150 ppm to about 250 ppm, about 150 ppm to about 275 ppm, about 150 ppm to about 300 ppm, about 150 ppm to about 325 ppm, about 150 ppm to about 350 ppm, about 150 ppm to about 375 ppm, about 150 ppm to about 400 ppm, about 200 ppm to about 225 ppm, about 200 ppm to about 250 ppm, about 200 ppm to about 275 ppm, about 200 ppm to about 300 ppm, about 200 ppm to about 325 ppm, about 200 ppm to about 350 ppm, about 200 ppm to about 375 ppm, about 200 ppm to about 400 ppm, about 250 ppm to about 275 ppm, about 250 ppm to about 300 ppm, about 250 ppm to about 325 ppm, about 250 ppm to about 350 ppm, about 250 ppm to about 375 ppm, about 250 ppm to about 400 ppm, about 300 ppm to about 325 ppm, about 300 ppm to about 350 ppm, about 300 ppm to about 375 ppm, about 300 ppm to about 400 ppm, about 350 ppm to about 375 ppm, about 350 ppm to about 400 ppm, or about 375 ppm to about 400 ppm.

In other aspects of this embodiment, a composition disclosed herein comprises free available chlorine in an amount of, e.g., about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 400 ppm to about 1,100 ppm, about 400 ppm to about 1,200 ppm, about 400 ppm to about 1,300 ppm, about 400 ppm to about 1,400 ppm, about 400 ppm to about 1,500 ppm, about 500 ppm to about 600 ppm, about 500 ppm to about 700 ppm, about 500 ppm to about 800 ppm, about 500 ppm to about 900 ppm, about 500 ppm to about 1,000 ppm, about 500 ppm to about 1,100 ppm, about 500 ppm to about 1,200 ppm, about 500 ppm to about 1,300 ppm, about 500 ppm to about 1,400 ppm, about 500 ppm to about 1,500 ppm, about 600 ppm to about 700 ppm, about 600 ppm to about 800 ppm, about 600 ppm to about 900 ppm, about 600 ppm to about 1,000 ppm, about 600 ppm to about 1,100 ppm, about 600 ppm to about 1,200 ppm, about 600 ppm to about 1,300 ppm, about 600 ppm to about 1,400 ppm, about 600 ppm to about 1,500 ppm, about 700 ppm to about 800 ppm, about 700 ppm to about 900 ppm, about 700 ppm to about 1,000 ppm, about 700 ppm to about 1,100 ppm, about 700 ppm to about 1,200 ppm, about 700 ppm to about 1,300 ppm, about 700 ppm to about 1,400 ppm, about 700 ppm to about 1,500 ppm, about 800 ppm to about 900 ppm, about 800 ppm to about 1,000 ppm, about 800 ppm to about 1,100 ppm, about 800 ppm to about 1,200 ppm, about 800 ppm to about 1,300 ppm, about 800 ppm to about 1,400 ppm, about 800 ppm to about 1,500 ppm, about 900 ppm to about 1,000 ppm, about 900 ppm to about 1,100 ppm, about 900 ppm to about 1,200 ppm, about 900 ppm to about 1,300 ppm, about 900 ppm to about 1,400 ppm, about 900 ppm to about 1,500 ppm, about 1,000 ppm to about 1,100 ppm, about 1,000 ppm to about 1,200 ppm, about 1,000 ppm to about 1,300 ppm, about 1,000 ppm to about 1,400 ppm, about 1,000 ppm to about 1,500 ppm, about 1,100 ppm to about 1,200 ppm, about 1,100 ppm to about 1,300 ppm, about 1,100 ppm to about 1,400 ppm, about 1,100 ppm to about 1,500 ppm, about 1,200 ppm to about 1,300 ppm, about 1,200 ppm to about 1,400 ppm, about 1,200 ppm to about 1,500 ppm, about 1,300 ppm to about 1,500 ppm, or about 1,400 ppm to about 1,500 ppm.

In one embodiment, a composition disclosed herein does not comprise ozone. In another embodiment, a composition disclosed herein can comprise ozone.

In one embodiment, a composition disclosed herein does not comprise hydrogen peroxide. In another embodiment, a composition disclosed herein can comprise hydrogen peroxide.

A composition disclosed herein may comprise a disinfectant. A disinfectant can be one or more compounds containing a biguanide moiety or functional group, one or more aldehyde-containing compounds, or one or more organic peroxides, or any combination thereof.

A composition disclosed herein may comprise a compound containing a guanide moiety and/or functional group. Non-limiting examples of a guanide-containing compound include an organic compound containing a biguanide functional group, a biguanidine functional group or a triguanide functional group. In one embodiment, a guanide-containing compound disclosed herein is a biguanide or a biguanide-containing compound. In an aspect of this embodiment, a biguanide-containing compound comprises one, two, three, four or five biguanide functional groups. In an aspect of this embodiment, a biguanide-containing compound comprises of formula II,

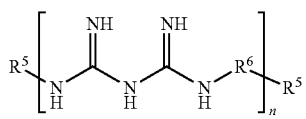

II wherein $R^5$ and $R^6$ can each independently be a bond, H, C, NH, $NH^2$, a $C_{1-10}$ alkyl, a $C_{1-10}$ alkane, a $C_{1-10}$ alkyne, a 5 or 6 carbon aromatic ring, optionally substituted with a halogen; and n is 1-5. A halogen is F, Br, Cl, I, and At. Non-limiting examples of a biguanide-containing compound include a polyhexamethylene biguanide (PHMB), a polyaminopropyl biguanide (PAPB), a 1,1'-(1,6-Hexanediyl)bis{2-[N'-(2-ethylhexyl)carbamimidoyl]guanidine} (alexidine), a chlorhexidine and a chlorhexidine gluconate.

In one embodiment, a guanide-containing compound disclosed herein is a biguanidine or a biguanidine-containing compound. In an aspect of this embodiment, a biguanidine-containing compound comprises one, two, three, four or five biguanidine functional groups. In an aspect of this embodiment, a biguanidine-containing compound comprises of formula III,

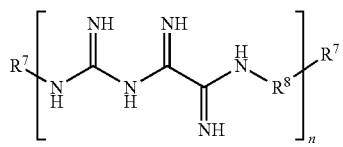

III wherein $R^7$ and $R^8$ can each independently be a bond, H, C, NH, $NH^2$, a $C_{1-10}$ alkyl, a $C_{1-10}$ alkane, a $C_{1-10}$ alkyne, a 5 or 6 carbon aromatic ring, optionally substituted with a halogen; and n is 1-5. A halogen is F, Br, Cl, I, and At.

In one embodiment, a guanide-containing compound disclosed herein is a triguanide or a triguanide-containing compound. In an aspect of this embodiment, a triguanide-containing compound comprises one, two, three, four or five triguanide functional groups. In an aspect of this embodiment, a triguanide-containing compound comprises formula IV,

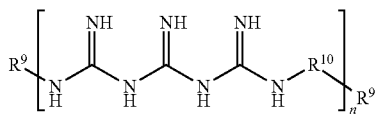

IV wherein $R^9$ and $R^{19}$ can each independently be a bond, H, C, NH, $NH^2$, a $C_{1-10}$ alkyl, a $C_{1-10}$ alkane, a $C_{1-10}$ alkyne, a 5 or 6 carbon aromatic ring, optionally substituted with a halogen; and n is 1-5. A halogen is F, Br, Cl, I, and At.

In one embodiment, a single guanide-containing compound is present in a composition disclosed herein. In another embodiment, a plurality of guanide-containing compounds is present in a composition disclosed herein. In aspects of this embodiment, a composition disclosed herein comprises, e.g., one or more guanide-containing compounds, two or more guanide-containing compounds, three or more guanide-containing compounds, four or more guanide-containing compounds or five or more guanide-containing compounds. In other aspects of this embodiment, a composition disclosed herein comprises, e.g., only one guanide-containing compound, at most two guanide-containing compounds, at most three guanide-containing compounds, at most four guanide-containing compounds, or at most five guanide-containing compounds. In yet other aspects of this embodiment, a composition disclosed herein comprises from, e.g., 1 to 2 guanide-containing compounds, 1 to 3 guanide-containing compounds, 1 to 4 guanide-containing compounds, 1 to 5 guanide-containing compounds, 2 to 3 guanide-containing compounds, 2 to 4 guanide-containing compounds, 2 to 5 guanide-containing compounds, 3 to 4 guanide-containing compounds, 3 to 5 guanide-containing compounds or 4 to 5 guanide-containing compounds.

Any amount of a guanide-containing compound disclosed herein may be used, with the proviso that the amount is useful to practice the methods disclosed herein. In aspects of this embodiment, a composition disclosed herein comprises a guanide-containing compound in an amount of, e.g., about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0%, about 10.0%. about 11%, about 12%, about 13%, about 14%, about 15%, about 20%, about 25%, or about 30% by weight of the composition. In other aspects of this embodiment, a composition disclosed herein comprises a guanide-containing compound in an amount of, e.g., at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, at least 10.0%, at least 11%, at least 12%, at least 13%, at least 14%, at least 15%, at least 20%, at least 25%, or at least 30% by weight of the composition. In yet other aspects of this embodiment, a composition disclosed herein comprises a guanide-containing compound in an amount of, e.g., at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0%, at most 10.0%, at most 11%, at most 12%, at most 13%, at most 14%, at most 15%, at most 20%, at most 25%, or at most 30% by weight of the composition.

In still other aspects of this embodiment, a composition disclosed herein comprises a guanide-containing compound in an amount of, e.g., about 0.1% to about 0.5%, about 0.1% to about 0.75%, about 0.1% to about 1.0%, about 0.1% to about 1.5%, about 0.1% to about 2.0%, about 0.1% to about 2.5%, about 0.1% to about 3.0%, about 0.1% to about 3.5%, about 0.1% to about 4.0%, about 0.1% to about 4.5%, about 0.1% to about 5.0%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.2% to about 3.0%, about 0.2% to about 3.5%, about 0.2% to about 4.0%, about 0.2% to about 4.5%, about 0.2% to about 5.0%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 1.0% to about 15.0%, about 1.0% to about 20.0%, about 1.0% to about 25.0%, about 1.0% to about 30.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 2.0% to about 15.0%, about 2.0% to about 20.0%, about 2.0% to about 25.0%, about 2.0% to about 30.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0%, about 5.0% to about 15.0%, about 5.0% to about 20.0%, about 5.0% to about 25.0%, about 5.0% to about 30.0%, about 6.0% to about 7.0%, about 6.0% to about 7.5%, about 6.0% to about 8.0%, about 6.0% to about 9.0%, about 6.0% to about 10.0%, about 6.0% to about 11.0%, about 6.0% to about 12.0%, about 6.0% to about 13.0%, about 6.0% to about 14.0%, about 6.0% to about 15.0%, about 6.0% to about 20.0%, about 6.0% to about 25.0%, about 6.0% to about 30.0%, about 7.0% to about 8.0%, about 7.0% to about 9.0%, about 7.0% to about 10.0%, about 7.0% to about 11.0%, about 7.0% to about 12.0%, about 7.0% to about 13.0%, about 7.0% to about 14.0%, about 7.0% to about 15.0%, about 7.0% to about 20.0%, about 7.0% to about 25.0%, about 7.0% to about 30.0%, about 8.0% to about 9.0%, about 8.0% to about 10.0%, about 8.0% to about 11.0%, about 8.0% to about 12.0%, about 8.0% to about 13.0%, about 8.0% to about 14.0%, about 8.0% to about 15.0%, about 8.0% to about 20.0%, about 8.0% to about 25.0%, about 8.0% to about 30.0%, about 9.0% to about 10.0%, about 9.0% to about 11.0%, about 9.0% to about 12.0%, about 9.0% to about 13.0%, about 9.0% to about 14.0%, about 9.0% to about 15.0%, about 9.0% to about 20.0%, about 9.0% to about 25.0%, about 9.0% to about 30.0%, about 10.0% to about 11.0%, about 10.0% to about 12.0%, about 10.0% to about 13.0%, about 10.0% to about 14.0%, about 10.0% to about 15.0%, about 10.0% to about 20.0%, about 10.0% to about 25.0%, about 10.0% to about 30.0%, about 15.0% to about 20.0%, about 15.0% to about 25.0%, about 15.0% to about 30.0%, about 20.0% to about 25.0%, about 20.0% to about 30.0%, or about 20.0% to about 30.0%, by weight of the composition.

In another embodiment, a composition disclosed herein does not comprise a guanide-containing compound. In another embodiment, a composition disclosed herein does not comprise biguanide. In another embodiment, a composition disclosed herein does not comprise a biguanide-containing compound. In another embodiment, a composition disclosed herein does not comprise biguanidine. In another embodiment, a composition disclosed herein does not comprise a biguanidine-containing compound. In another embodiment, a composition disclosed herein does not comprise triguanide. In another embodiment, a composition disclosed herein does not comprise a triguanide-containing compound.

A composition disclosed herein may comprise an aldehyde-containing compound. An aldehyde-containing compound can be a linear aldehyde, a branched aldehyde, a cyclic aldehyde an aromatic aldehyde, a linear dialdehyde, a branched dialdehyde, a cyclic dialdehyde, or an aromatic dialdehyde.

An aldehyde is an organic compound containing a —CHO functional group and having a carbonyl center (a carbon double-bonded to oxygen) with the carbon atom also bonded to hydrogen and an R group. In one embodiment, an aldehyde disclosed herein is a compound of formula V, wherein the $R^1$ group can be H, a $C_{1-6}$ alkyl, a $C_{1-6}$ alkane, a $C_{1-6}$ alkyne, a $C_{3-6}$ cyclic alkyl, or a $C_{3-6}$ aryl.

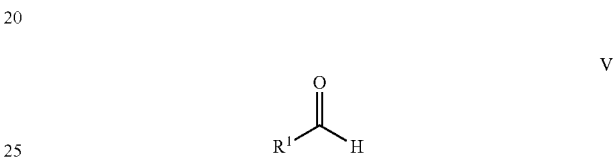

V

Non-limiting examples of an aldehyde include formaldehyde, acetaldehyde, propionaldehyde, and butyraldehyde.

A dialdehyde is an organic chemical compound with two aldehyde groups. In one embodiment, an aldehyde disclosed herein is a compound of formula VI, wherein the $R^2$ group can be a bond, a $C_{1-6}$ alkyl, a $C_{1-6}$ alkane, a $C_{1-6}$ alkyne, a $C_{3-6}$ cyclic alkyl, or a $C_{3-6}$ aryl.

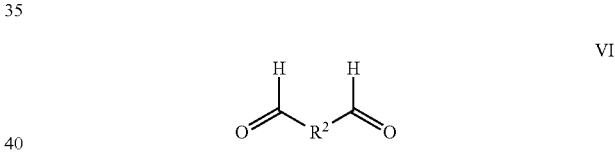

VI

Non-limiting examples of a dialdehyde include oxaldehyde, malondialdehyde, glutaraldehyde, succinicdialdehyde, phthalaldehyde (ortho-phthalaldehyde), isophthalaldehyde (meta-phthalaldehyde), and terephthalaldehyde (para-phthalaldehyde).

In one embodiment, a single aldehyde-containing compound is present in a composition disclosed herein. In another embodiment, a plurality of aldehyde-containing compounds is present in a composition disclosed herein. In aspects of this embodiment, a composition disclosed herein comprises, e.g., one or more aldehyde-containing compounds, two or more aldehyde-containing compounds, three or more aldehyde-containing compounds, four or more aldehyde-containing compounds or five or more aldehyde-containing compounds. In other aspects of this embodiment, a composition disclosed herein comprises, e.g., only one aldehyde-containing compound, at most two aldehyde-containing compounds, at most three aldehyde-containing compounds, at most four aldehyde-containing compounds, or at most five aldehyde-containing compounds. In yet other aspects of this embodiment, a composition disclosed herein comprises from, e.g., 1 to 2 aldehyde-containing compounds, 1 to 3 aldehyde-containing compounds, 1 to 4 aldehyde-containing compounds, 1 to 5 aldehyde-containing compounds, 2 to 3 aldehyde-containing compounds, 2 to 4 aldehyde-containing compounds, 2 to 5 aldehyde-containing compounds, 3 to 4 aldehyde-containing compounds, 3 to 5 aldehyde-containing compounds or 4 to 5 aldehyde-containing compounds.

Any amount of an aldehyde-containing compound disclosed herein may be used, with the proviso that the amount is useful to practice the methods disclosed herein. In aspects of this embodiment, a composition disclosed herein comprises an aldehyde-containing compound in an amount of, e.g., about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition. In other aspects of this embodiment, a composition disclosed herein comprises an aldehyde-containing compound in an amount of, e.g., at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0% by weight of the composition. In yet other aspects of this embodiment, a composition disclosed herein comprises an aldehyde-containing compound in an amount of, e.g., at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition.

In still other aspects of this embodiment, a composition disclosed herein comprises an aldehyde-containing compound in an amount of, e.g., about 0.1% to about 0.5%, about 0.1% to about 0.75%, about 0.1% to about 1.0%, about 0.1% to about 1.5%, about 0.1% to about 2.0%, about 0.1% to about 2.5%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0% or about 5.0% to about 15.0% by weight of the composition.

In aspects of this embodiment, a composition disclosed herein comprises an aldehyde-containing compound in an amount of, e.g., 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, or 1,000 ppm. In other aspects of this embodiment, a composition disclosed herein comprises an aldehyde-containing compound in an amount of, e.g., at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, or at least 1,000 ppm. In yet other aspects of this embodiment, a composition disclosed herein comprises an aldehyde-containing compound in an amount of, e.g., at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, or at most 1,000 ppm.

In still other aspects of this embodiment, a composition disclosed herein comprises an aldehyde-containing compound in an amount of, e.g., about 100 ppm to about 200 ppm, about 100 ppm to about 300 ppm, about 100 ppm to about 400 ppm, about 100 ppm to about 500 ppm, about 100 ppm to about 600 ppm, about 100 ppm to about 700 ppm, about 100 ppm to about 800 ppm, about 100 ppm to about 900 ppm, about 100 ppm to about 1,000 ppm, about 200 ppm to about 300 ppm, about 200 ppm to about 400 ppm, about 200 ppm to about 500 ppm, about 200 ppm to about 600 ppm, about 200 ppm to about 700 ppm, about 200 ppm to about 800 ppm, about 200 ppm to about 900 ppm, about 200 ppm to about 1,000 ppm, about 300 ppm to about 400 ppm, about 300 ppm to about 500 ppm, about 300 ppm to about 600 ppm, about 300 ppm to about 700 ppm, about 300 ppm to about 800 ppm, about 300 ppm to about 900 ppm, about 300 ppm to about 1,000 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 500 ppm to about 600 ppm, about 500 ppm to about 700 ppm, about 500 ppm to about 800 ppm, about 500 ppm to about 900 ppm, about 500 ppm to about 1,000 ppm, about 600 ppm to about 700 ppm, about 600 ppm to about 800 ppm, about 600 ppm to about 900 ppm, about 600 ppm to about 1,000 ppm, about 700 ppm to about 800 ppm, about 700 ppm to about 900 ppm, about 700 ppm to about 1,000 ppm, about 800 ppm to about 900 ppm, about 800 ppm to about 1,000 ppm, or about 900 ppm to about 1,000 ppm.

In another embodiment, a composition disclosed herein does not comprise an aldehyde-containing compound.

In one embodiment, a single aldehyde is present in a composition disclosed herein. In another embodiment, a plurality of aldehydes is present in a composition disclosed herein. In aspects of this embodiment, a composition disclosed herein comprises, e.g., one or more aldehydes, two or more aldehydes, three or more aldehydes, four or more aldehydes or five or more aldehydes. In other aspects of this embodiment, a composition disclosed herein comprises, e.g., only one aldehyde, at most two aldehydes, at most three aldehydes, at most four aldehydes, or at most five aldehydes.

In yet other aspects of this embodiment, a composition disclosed herein comprises from, e.g., 1 to 2 aldehydes, 1 to 3 aldehydes, 1 to 4 aldehydes, 1 to 5 aldehydes, 2 to 3 aldehydes, 2 to 4 aldehydes, 2 to 5 aldehydes, 3 to 4 aldehydes, 3 to 5 aldehydes or 4 to 5 aldehydes.

Any amount of an aldehyde disclosed herein may be used, with the proviso that the amount is useful to practice the methods disclosed herein. In aspects of this embodiment, a composition disclosed herein comprises an aldehyde in an amount of, e.g., about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition. In other aspects of this embodiment, a composition disclosed herein comprises an aldehyde in an amount of, e.g., at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0% by weight of the composition. In yet other aspects of this embodiment, a composition disclosed herein comprises an aldehyde in an amount of, e.g., at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition.

In still other aspects of this embodiment, a composition disclosed herein comprises an aldehyde in an amount of, e.g., about 0.1% to about 0.5%, about 0.1% to about 0.75%, about 0.1% to about 1.0%, about 0.1% to about 1.5%, about 0.1% to about 2.0%, about 0.1% to about 2.5%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0% or about 5.0% to about 15.0% by weight of the composition.

In aspects of this embodiment, a composition disclosed herein comprises an aldehyde in an amount of, e.g., 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, or 1,000 ppm. In other aspects of this embodiment, a composition disclosed herein comprises an aldehyde in an amount of, e.g., at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, or at least 1,000 ppm. In yet other aspects of this embodiment, a composition disclosed herein comprises an aldehyde in an amount of, e.g., at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, or at most 1,000 ppm.

In still other aspects of this embodiment, a composition disclosed herein comprises an aldehyde in an amount of, e.g., about 100 ppm to about 200 ppm, about 100 ppm to about 300 ppm, about 100 ppm to about 400 ppm, about 100 ppm to about 500 ppm, about 100 ppm to about 600 ppm, about 100 ppm to about 700 ppm, about 100 ppm to about 800 ppm, about 100 ppm to about 900 ppm, about 100 ppm to about 1,000 ppm, about 200 ppm to about 300 ppm, about 200 ppm to about 400 ppm, about 200 ppm to about 500 ppm, about 200 ppm to about 600 ppm, about 200 ppm to about 700 ppm, about 200 ppm to about 800 ppm, about 200 ppm to about 900 ppm, about 200 ppm to about 1,000 ppm, about 300 ppm to about 400 ppm, about 300 ppm to about 500 ppm, about 300 ppm to about 600 ppm, about 300 ppm to about 700 ppm, about 300 ppm to about 800 ppm, about 300 ppm to about 900 ppm, about 300 ppm to about 1,000 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 500 ppm to about 600 ppm, about 500 ppm to about 700 ppm, about 500 ppm to about 800 ppm, about 500 ppm to about 900 ppm, about 500 ppm to about 1,000 ppm, about 600 ppm to about 700 ppm, about 600 ppm to about 800 ppm, about 600 ppm to about 900 ppm, about 600 ppm to about 1,000 ppm, about 700 ppm to about 800 ppm, about 700 ppm to about 900 ppm, about 700 ppm to about 1,000 ppm, about 800 ppm to about 900 ppm, about 800 ppm to about 1,000 ppm, or about 900 ppm to about 1,000 ppm.

In another embodiment, a composition disclosed herein does not comprise an aldehyde.

In one embodiment, a single dialdehyde is present in a composition disclosed herein. In another embodiment, a plurality of dialdehydes is present in a composition disclosed herein. In aspects of this embodiment, a composition disclosed herein comprises, e.g., one or more dialdehydes, two or more dialdehydes, three or more dialdehydes, four or more dialdehydes or five or more dialdehydes. In other aspects of this embodiment, a composition disclosed herein comprises, e.g., only one dialdehyde, at most two dialdehydes, at most three dialdehydes, at most four dialdehydes, or at most five dialdehydes. In yet other aspects of this embodiment, a composition disclosed herein comprises from, e.g., 1 to 2 dialdehydes, 1 to 3 dialdehydes, 1 to 4 dialdehydes, 1 to 5 dialdehydes, 2 to 3 dialdehydes, 2 to 4 dialdehydes, 2 to 5 dialdehydes, 3 to 4 dialdehydes, 3 to 5 dialdehydes or 4 to 5 dialdehydes.

Any amount of a dialdehyde disclosed herein may be used, with the proviso that the amount is useful to practice the methods disclosed herein. In aspects of this embodiment, a composition disclosed herein comprises a dialdehyde in an amount of, e.g., about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition. In other aspects of this embodiment, a composition disclosed herein comprises a dialdehyde in an amount of, e.g., at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0 by weight of the composition. In yet other aspects of this embodiment, a composition disclosed herein comprises a dialdehyde in an amount of, e.g., at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition.

In still other aspects of this embodiment, a composition disclosed herein comprises a dialdehyde in an amount of, e.g., about 0.1% to about 0.5%, about 0.1% to about 0.75%, about 0.1% to about 1.0%, about 0.1% to about 1.5%, about 0.1% to about 2.0%, about 0.1% to about 2.5%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0% or about 5.0% to about 15.0% by weight of the composition.

In aspects of this embodiment, a composition disclosed herein comprises a dialdehyde in an amount of, e.g., 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, or 1,000 ppm. In other aspects of this embodiment, a composition disclosed herein comprises a dialdehyde in an amount of, e.g., at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, or at least 1,000 ppm. In yet other aspects of this embodiment, a composition disclosed herein comprises a dialdehyde in an amount of, e.g., at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, or at most 1,000 ppm.

In still other aspects of this embodiment, a composition disclosed herein comprises a dialdehyde in an amount of, e.g., about 100 ppm to about 200 ppm, about 100 ppm to about 300 ppm, about 100 ppm to about 400 ppm, about 100 ppm to about 500 ppm, about 100 ppm to about 600 ppm, about 100 ppm to about 700 ppm, about 100 ppm to about 800 ppm, about 100 ppm to about 900 ppm, about 100 ppm to about 1,000 ppm, about 200 ppm to about 300 ppm, about 200 ppm to about 400 ppm, about 200 ppm to about 500 ppm, about 200 ppm to about 600 ppm, about 200 ppm to about 700 ppm, about 200 ppm to about 800 ppm, about 200 ppm to about 900 ppm, about 200 ppm to about 1,000 ppm, about 300 ppm to about 400 ppm, about 300 ppm to about 500 ppm, about 300 ppm to about 600 ppm, about 300 ppm to about 700 ppm, about 300 ppm to about 800 ppm, about 300 ppm to about 900 ppm, about 300 ppm to about 1,000 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 500 ppm to about 600 ppm, about 500 ppm to about 700 ppm, about 500 ppm to about 800 ppm, about 500 ppm to about 900 ppm, about 500 ppm to about 1,000 ppm, about 600 ppm to about 700 ppm, about 600 ppm to about 800 ppm, about 600 ppm to about 900 ppm, about 600 ppm to about 1,000 ppm, about 700 ppm to about 800 ppm, about 700 ppm to about 900 ppm, about 700 ppm to about 1,000 ppm, about 800 ppm to about 900 ppm, about 800 ppm to about 1,000 ppm, or about 900 ppm to about 1,000 ppm.

In another embodiment, a composition disclosed herein does not comprise a dialdehyde.

A composition disclosed herein may comprise an organic peroxide. An organic peroxide is an organic compound containing a peroxide (ROOR') functional group. If one of the R groups is a hydrogen, the compound is referred to as an organic hydroperoxide. In one embodiment, an organic peroxide disclosed herein is a compound of formula VII, wherein $R^3$ and $R^4$ can each be independently H, a $C_{1-6}$ alkyl, a $C_{1-6}$ alkane, a $C_{1-6}$ alkyne, a $C_{3-6}$ cyclic alkyl, or a $C_{3-6}$ aryl.

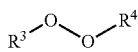

VII

Non-limiting examples of an organic peroxide include benzoyl peroxide and ethaneperoxoic acid (peracetic acid).

In one embodiment, a single organic peroxide is present in a composition disclosed herein. In another embodiment, a plurality of organic peroxides is present in a composition disclosed herein. In aspects of this embodiment, a composition disclosed herein comprises, e.g., one or more organic peroxides, two or more organic peroxides, three or more organic peroxides, four or more organic peroxides or five or more organic peroxides. In other aspects of this embodiment, a composition disclosed herein comprises, e.g., only one organic peroxide, at most two organic peroxides, at most three organic peroxides, at most four organic peroxides, or at most five organic peroxides. In yet other aspects of this embodiment, a composition disclosed herein comprises from, e.g., 1 to 2 organic peroxides, 1 to 3 organic peroxides, 1 to 4 organic peroxides, 1 to 5 organic peroxides, 2 to 3 organic peroxides, 2 to 4 organic peroxides, 2 to 5 organic peroxides, 3 to 4 organic peroxides, 3 to 5 organic peroxides or 4 to 5 organic peroxides.

Any amount of an organic peroxide disclosed herein may be used, with the proviso that the amount is useful to practice the methods disclosed herein. In aspects of this embodiment, a composition disclosed herein comprises an organic peroxide in an amount of, e.g., about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition. In other aspects of this embodiment, a composition disclosed herein comprises an organic peroxide in an amount of, e.g., at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0% by weight of the composition. In yet other aspects of this embodiment, a composition disclosed herein comprises an organic peroxide in an amount of, e.g., at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition.

In still other aspects of this embodiment, a composition disclosed herein comprises an organic peroxide in an amount of, e.g., about 0.1% to about 0.5%, about 0.1% to about 0.75%, about 0.1% to about 1.0%, about 0.1% to about 1.5%, about 0.1% to about 2.0%, about 0.1% to about 2.5%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0% or about 5.0% to about 15.0% by weight of the composition.

In aspects of this embodiment, a composition disclosed herein comprises an organic peroxide in an amount of, e.g., 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, or 1,000 ppm. In other aspects of this embodiment, a composition disclosed herein comprises an organic peroxide in an amount of, e.g., at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, or at least 1,000 ppm. In yet other aspects of this embodiment, a composition disclosed herein comprises an organic peroxide in an amount of, e.g., at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, or at most 1,000 ppm.

In still other aspects of this embodiment, a composition disclosed herein comprises an organic peroxide in an amount of, e.g., about 100 ppm to about 200 ppm, about 100 ppm to about 300 ppm, about 100 ppm to about 400 ppm, about 100 ppm to about 500 ppm, about 100 ppm to about 600 ppm, about 100 ppm to about 700 ppm, about 100 ppm to about 800 ppm, about 100 ppm to about 900 ppm, about 100 ppm to about 1,000 ppm, about 200 ppm to about 300 ppm, about 200 ppm to about 400 ppm, about 200 ppm to about 500 ppm, about 200 ppm to about 600 ppm, about 200 ppm to about 700 ppm, about 200 ppm to about 800 ppm, about 200 ppm to about 900 ppm, about 200 ppm to about 1,000 ppm, about 300 ppm to about 400 ppm, about 300 ppm to about 500 ppm, about 300 ppm to about 600 ppm, about 300 ppm to about 700 ppm, about 300 ppm to about 800 ppm, about 300 ppm to about 900 ppm, about 300 ppm to about 1,000 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 500 ppm to about 600 ppm, about 500 ppm to about 700 ppm, about 500 ppm to about 800 ppm, about 500 ppm to about 900 ppm, about 500 ppm to about 1,000 ppm, about 600 ppm to about 700 ppm, about 600 ppm to about 800 ppm, about 600 ppm to about 900 ppm, about 600 ppm to about 1,000 ppm, about 700 ppm to about 800 ppm, about 700 ppm to about 900 ppm, about 700 ppm to about 1,000 ppm, about 800 ppm to about 900 ppm, about 800 ppm to about 1,000 ppm, or about 900 ppm to about 1,000 ppm.

In another embodiment, a composition disclosed herein does not comprise an organic peroxide.

A composition disclosed herein may comprise one or more alcohols. An organic peroxide is an organic compound containing a peroxide (ROOR') functional group. If one of the R groups is a hydrogen, the compound is referred to as an organic hydroperoxide. In one embodiment, an organic peroxide disclosed herein is a compound of formula VII, wherein $R^3$ and $R^4$ can each be independently H, a $C_{1-6}$ alkyl, a $C_{1-6}$ alkane, a $C_{1-6}$ alkyne, a $C_{3-6}$ cyclic alkyl, or a $C_{3-6}$ aryl.

An alcohol is an organic molecule comprising a hydroxyl functional group (—OH) bond to a carbon atom, where the carbon atom is saturated. In aspects of this embodiment, the alcohol may be, e.g., a $C_{2-4}$ alcohol, a $C_{1-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol. In other aspects of this embodiment, an alcohol may be, e.g., a primary alcohol, a secondary alcohol, or a tertiary alcohol. In other aspects of this embodiment, an alcohol may be, e.g., an acyclic alcohol, a monohydric alcohol, a polyhydric alcohol (also known as a polyol or sugar alcohol), an unsaturated aliphatic alcohol, an alicyclic alcohol, or a combination thereof. Examples of a monohydric alcohol include, without limitation, methanol, ethanol, propanol, isopropanol, butanol, pentanol, and 1-hexadecanol. Examples of a polyhydric alcohol include, without limitation, glycol, glycerol, arabitol, erythritol, xylitol, maltitol, sorbitol (gluctiol), mannitol, inositol, lactitol, galactitol (iditol), and isomalt. Examples of an unsaturated aliphatic alcohol include, without limitation, prop-2-ene-1-ol, 3,7-dimethylocta-2,6-dien-1-ol, and prop-2-in-1-ol. Examples of an alicyclic alcohol include, without limitation, cyclohexane-1,2,3,4,5,6-hexol and 2-(2-propyl)-5-methyl-cyclohexane-1-ol.

In one embodiment, a single alcohol is present in a composition disclosed herein. In another embodiment, a plurality of alcohols is present in a composition disclosed herein. In aspects of this embodiment, a composition disclosed herein comprises, e.g., one or more alcohols, two or more alcohols, three or more alcohols, four or more alcohols or five or more alcohols. In other aspects of this embodiment, a composition disclosed herein comprises, e.g., only one alcohol, at most two alcohols, at most three alcohols, at most four alcohols, or at most five alcohols. In yet other aspects of this embodiment, a composition disclosed herein comprises from, e.g., 1 to 2 alcohols, 1 to 3 alcohols, 1 to 4 alcohols, 1 to 5 alcohols, 2 to 3 alcohols, 2 to 4 alcohols, 2 to 5 alcohols, 3 to 4 alcohols, 3 to 5 alcohols or 4 to 5 alcohols.

In aspects of this embodiment, a plurality of alcohols is present in a composition disclosed herein may comprise, e.g., about 95% of a first alcohol and about 5% of a second alcohol, about 90% of a first alcohol and about 10% of a second alcohol, about 80% of a first alcohol and about 20% of a second alcohol, about 70% of a first alcohol and about 30% of a second alcohol, about 66.7% of a first alcohol and about 33.3% of a second alcohol, about 60% of a first alcohol and about 40% of a second alcohol, about 50% of a first alcohol and about 50% of a second alcohol, about 40% of a first alcohol and about 60% of a second alcohol, about 30% of a first alcohol and about 70% of a second alcohol, about 20% of a first alcohol and about 80% of a second alcohol, about 10% of a first alcohol and about 90% of a second alcohol, about 5% of a first alcohol and about 95% of a second alcohol. In other aspects of this embodiment, the ratio of a first alcohol to a second alcohol is, e.g., 100:1, 90:1, 80:1, 70:1, 60:1, 50:1, 40:1, 30:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or 1:100. In other aspects, the first alcohol is isopropanol and the second alcohol is ethanol.

Any amount of an alcohol disclosed herein may be used, with the proviso that the amount is useful to practice the methods disclosed herein. In aspects of this embodiment, a composition disclosed herein comprises an alcohol in an amount of, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99%, by weight of the composition. In other aspects of this embodiment, a composition disclosed herein comprises an alcohol in an amount of, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%, by weight of the composition. In yet other aspects of this embodiment, a composition disclosed herein comprises an alcohol in an amount of, e.g., at most 5%, at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95%, at most 96%, at most 97%, at most 98%, or at most 99%, by weight of the composition. In still other aspects of this embodiment, a composition disclosed herein comprises an alcohol in an amount of, e.g., about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 5% to about 95%, about 5% to about 97%, about 5% to about 99%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 10% to about 97%, about 10% to about 99%, about 20% to about 30%, about 20% to about 40%, about 20% to about 50%, about 20% to about 60%, about 20% to about 70%, about 20% to about 80%, about 20% to about 90%, about 20% to about 95%, about 20% to about 97%, about 20% to about 99%, about 30% to about 40%, about 30% to about 50%, about 30% to about 60%, about 30% to about 70%, about 30% to about 80%, about 30% to about 90%, about 30% to about 95%, about 30% to about 97%, about 30% to about 99%, about 35% to about 40%, about 35% to about 50%, about 35% to about 60%, about 35% to about 70%, about 35% to about 80%, about 35% to about 90%, about 35% to about 95%, about 35% to about 97%, about 35% to about 99%, about 40% to about 50%, about 40% to about 60%, about 40% to about 70%, about 40% to about 80%, about 40% to about 90%, about 40% to about 95%, about 40% to about 97%, about 40% to about 99%, about 45% to about 50%, about 45% to about 60%, about 45% to about 70%, about 45% to about 80%, about 45% to about 90%, about 45% to about 95%, about 45% to about 97%, about 45% to about 99%, about 50% to about 60%, about 50% to about 70%, about 50% to about 80%, about 50% to about 90%, about 50% to about 95%, about 50% to about 97%, about 50% to about 99%, about 60% to about 70%, about 60% to about 80%, about 60% to about 90%, about 60% to about 95%, about 60% to about 97%, about 60% to about 99%, about 70% to about 80%, about 70% to about 90%, about 70% to about 95%, about 70% to about 97%, about 70% to about 99%, about 80% to about 90%, about 80% to about 95%, about 80% to about 97%, about 80% to about 99%, about 90% to about 95%, about 90% to about 97%, about 90% to about 99%, by weight of the composition.

In aspects of this embodiment, a composition disclosed herein comprises a plurality of alcohols in a total amount of, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99%, by weight of the composition. In other aspects of this embodiment, a composition disclosed herein comprises a plurality of alcohols in a total amount of, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%, by weight of the composition. In yet other aspects of this embodiment, a composition disclosed herein comprises a plurality of alcohols in a total amount of, e.g., at most 5%, at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95%, at most 96%, at most 97%, at most 98%, or at most 99%, by weight of the composition. In still other aspects of this embodiment, a composition disclosed herein comprises a plurality of alcohols in a total amount of, e.g., about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 5% to about 95%, about 5% to about 97%, about 5% to about 99%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 10% to about 97%, about 10% to about 99%, about 20% to about 30%, about 20% to about 40%, about 20% to about 50%, about 20% to about 60%, about 20% to about 70%, about 20% to about 80%, about 20% to about 90%, about 20% to about 95%, about 20% to about 97%, about 20% to about 99%, about 30% to about 40%, about 30% to about 50%, about 30% to about 60%, about 30% to about 70%, about 30% to about 80%, about 30% to about 90%, about 30% to about 95%, about 30% to about 97%, about 30% to about 99%, about 35% to about 40%, about 35% to about 50%, about 35% to about 60%, about 35% to about 70%, about 35% to about 80%, about 35% to about 90%, about 35% to about 95%, about 35% to about 97%, about 35% to about 99%, about 40% to about 50%, about 40% to about 60%, about 40% to about 70%, about 40% to about 80%, about 40% to about 90%, about 40% to about 95%, about 40% to about 97%, about 40% to about 99%, about 45% to about 50%, about 45% to about 60%, about 45% to about 70%, about 45% to about 80%, about 45% to about 90%, about 45% to about 95%, about 45% to about 97%, about 45% to about 99%, about 50% to about 60%, about 50% to about 70%, about 50% to about 80%, about 50% to about 90%, about 50% to about 95%, about 50% to about 97%, about 50% to about 99%, about 60% to about 70%, about 60% to about 80%, about 60% to about 90%, about 60% to about 95%, about 60% to about 97%, about 60% to about 99%, about 70% to about 80%, about 70% to about 90%, about 70% to about 95%, about 70% to about 97%, about 70% to about 99%, about 80% to about 90%, about 80% to about 95%, about 80% to about 97%, about 80% to about 99%, about 90% to about 95%, about 90% to about 97%, about 90% to about 99%, by weight of the composition.

In another embodiment, a composition disclosed herein does not comprise an alcohol. In an aspect of this embodiment, a composition disclosed herein does not comprise an ethanol. In another aspect of this embodiment, a composition disclosed herein does not comprise an isopropanol.

A composition disclosed herein may comprise a carrier. A carrier, also known as a vehicle, can be any material typically known in the skin care, cosmetic and medical arts that is used as a base to formulate a composition disclosed herein. A carrier may be an aqueous carrier, a semi-solid carrier or a solid carrier. A carrier can also provide a skin care benefit as disclosed herein. A carrier includes, without limitation, water, a vegetable oil, a mineral oil, an ester oil, an ether, an alcohol, a fatty alcohol, an isoparaffin, a hydrocarbon oil, a polyol, and a wax. Non-limiting examples of an ester oil include octal palmitate, isopropyl myristate and isopropyl palmitate. Non-limiting examples of an ether includes dicapryl ether and dimethyl isosorbide. Non-limiting examples of an alcohol includes ethanol and isopropanol. Non-limiting examples of a fatty alcohol include cetyl alcohol, cetearyl alcohol, stearyl alcohol and behenyl alcohol. Non-limiting examples of an isoparaffin include isooctane, isododecane (IDD) and isohexadecane. Non-limiting examples of a hydrocarbon oil include mineral oil, petrolatum, isoeicosane and a polyolefin, including (hydrogenated) polyisobutene. Non-limiting examples of a polyol include propylene glycol, glycerin, butylene glycol, pentylene glycol, hexylene glycol, caprylyl glycol. Non-limiting examples of a wax include beeswax, carnauba, ozokerite, microcrystalline wax, polyethylene wax, and a botanical wax.

In one embodiment, a single carrier is present in a composition disclosed herein. In another embodiment, a plurality of carriers is present in a composition disclosed herein. In aspects of this embodiment, a composition disclosed herein comprises, e.g., one or more carriers, two or more carriers, three or more carriers, four or more carriers or five or more carriers. In other aspects of this embodiment, a composition disclosed herein comprises, e.g., only one carrier, at most two carriers, at most three carriers, at most four carriers, or at most five carriers. In yet other aspects of this embodiment, a composition disclosed herein comprises from, e.g., 1 to 2 carriers, 1 to 3 carriers, 1 to 4 carriers, 1 to 5 carriers, 2 to 3 carriers, 2 to 4 carriers, 2 to 5 carriers, 3 to 4 carriers, 3 to 5 carriers or 4 to 5 carriers.

In another embodiment, a composition disclosed herein comprises an amount of carrier that provides a desired formulative or beneficial effect to a composition disclosed herein. In aspects of this embodiment, a composition disclosed herein comprises a carrier in an amount of, e.g., at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% by weight of the composition. In other aspects of this embodiment, a composition disclosed herein comprises a carrier in an amount of, e.g., at most 25%, at most 30%, at most 35%, at most 40%, at most 45%, at most 50%, at most 55%, at most 60%, at most 65%, at most 70%, at most 75%, at most 80%, at most 85%, at most 90%, at most 95%, at most 96%, at most 97%, at most 98% or at most 99% by weight of the composition. In yet other aspects of this embodiment, a composition disclosed herein comprises a carrier in an amount of from, e.g., about 25% to about 50%, about 25% to about 75%, about 25% to about 90%, about 25% to about 95%, about 25% to about 96%, about 25% to about 97%, about 25% to about 98%, about 25% to about 99%, about 50% to about 75%, about 50% to about 90%, about 50% to about 95%, about 50% to about 96%, about 50% to about 97%, about 50% to about 98%, about 50% to about 99%, about 75% to about 80%, about 75% to about 85%, about 75% to about 90%, about 75% to about 95%, about 75% to about 96%, about 75% to about 97%, about 75% to about 98%, about 75% to about 99%, about 80% to about 85%, about 80% to about 90%, about 80% to about 95%, about 80% to about 96%, about 80% to about 97%, about 80% to about 98%, about 80% to about 99%, about 85% to about 90%, about 85% to about 95%, about 85% to about 96%, about 85% to about 97%, about 85% to about 98%, about 85% to about 99%, about 90% to about 95%, about 90% to about 96%, about 90% to about 97%, about 90% to about 98%, about 90% to about 99%, or about 95% to about 99%, by weight of the composition.

In another embodiment, a composition disclosed herein comprises a carrier which is not an alcohol. In aspects of this embodiment, when a composition disclosed herein comprises hypochlorous acid or free available chlorine, then the composition may comprise a carrier where the carrier is not an alcohol.

A composition disclosed herein may further optionally include additional ingredients. An additional ingredient is one known to be useful in finishing a composition disclosed herein. An additional ingredient includes, without limitation, a surfactant, a preservative, or a chelating agent. An additional ingredient disclosed herein is known in the art.

Surfactants are compounds that lower the surface tension of a liquid, allowing easier spreading, and lowering of the interfacial tension between two liquids, or between a liquid and a solid. By acting at the interface of two surfaces, surfactants modulate the interfacial tension resulting in the formation of the foam. Either a single surfactant may be mixed with the buffered solution disclosed herein, or a plurality of surfactants may be mixed with the buffered solution disclosed herein. Useful surfactants, include, without limitation, ionic surfactants, zwitterionic (amphoteric) surfactants, non-ionic surfactants, or any combination therein. The surfactant used in a composition disclosed herein can be varied as appropriate by one skilled in the art and generally depends, in part, on the particular buffer being used, the protein being eluted, and the conductivity values being employed.

Ionic surfactants include anionic surfactants. Anionic surfactants include ones based on permanent functional groups attached to the head, such as, e.g., sulfate, sulfonate, phosphate carboxylates) or pH dependent anionic surfactants. Anionic surfactants include, without limitation, alkyl sulfates like ammonium lauryl sulfate and sodium lauryl sulfate (SDS); alkyl ether sulfates like sodium laureth sulfate and sodium myreth sulfate; docusates like dioctyl sodium sulfosuccinate; sulfonate fluorosurfactants like perfluorooctanesulfonate (PFOS) and perfluorobutanesulfonate; alkyl-diphenyloxide Disulfonates like DOWFAX™ 2A1 (Disodium Lauryl Phenyl Ether Disulfonate), DOWFAX™ 3B2 (Disodium Decyl Phenyl Ether Disulfonate), DOWFAX™ C10L (Disodium Decyl Phenyl Ether Disulfonate), DOWFAX™ 2EP, and DOWFAX™ 8390 (Disodium Cetyl Phenyl Ether Disulfonate); potassium phosphate polyether esters like TRITON™ H-55 and TRITON™ H-66; alkyl benzene sulfonates; alkyl aryl ether phosphates; alkyl ether phosphates; alkyl carboxylates like fatty acid salts and sodium stearate; sodium lauroyl sarcosinate; carboxylate fluorosurfactants like perfluorononanoate and perfluorooctanoate; and Sodium Hexyldiphenyl Ether Sulfonate (DOWFAX™ C6L).

Ionic surfactants also include cationic surfactants. Cationic surfactants include ones based on permanent or pH dependent cationic surfactants, such as, e.g., primary, secondary or tertiary amines. Cationic surfactants include, without limitation, quaternary ammonium surfactants like alkyl-trimethylammonium salts and alkyl-benzyldimethyl-ammonium salts as well as pH-dependent primary, secondary or tertiary amines like surfactants where the primary amines become positively charged at pH greater than 10, or the secondary amines become charged at pH less than 4, like octenidine dihydrochloride. Non-limiting examples of quaternary ammonium surfactants include first generation quaternary ammonium surfactants comprising $C_{12-18}$ alkyl chains, second generation quaternary ammonium surfactants comprising aromatic ring groups, third generation quaternary ammonium surfactants comprising dual first generation quaternary ammonium compounds and/or mixtures of alkyl dimethyl ammonium chloride, fourth generation quaternary ammonium surfactants comprising dialkylmethyl aminos with twin chains, fifth generation quaternary ammonium surfactants comprising synergistic combinations of dual quaternary ammonium compounds, six generation quaternary ammonium surfactants comprising polymeric quaternary ammonium compounds, and seventh generation quaternary ammonium surfactants comprising bis-quaternary ammonium compounds with polymeric quaternary ammonium compounds. Quaternary ammonium surfactants include, without limitation, benzalkonium chloride (BAC), benzethonium chloride (BZT), benzododecinium bromide (or dimethyldodecylbenzylammonium bromide), bronidox, (or 5-bromo-5-nitro-1,3-dioxane), carbethopendecinium bromide, cetalkonium chloride (CKC), cetrimonium, cetrimide, cetylpyridinium chloride (CPC), cetyl trimethylammonium bromide (CTAB or cetrimonium bromide) and cetyl trimethylammonium chloride (CTAC or cetrimonium chloride), didecyldimethylammonium chloride (DDAC), dioctadecyldimethylammonium bromide (DODAB or dimethyldioctadecylammonium bromide), dioctadecyldimethylammonium chloride (DODAC or dimethyldioctadecylammonium chloride), docosyltrimethylammonium chloride (DCTAC or behentrimonium chloride), dofanium chloride, domiphen bromide, methylbenzethonium chloride, octenidine dihydrochloride, polidronium chloride, stearalkonium chloride (or dimethylbenzyloctadecylammonium), tetraethylammonium bromide, tetramethylammonium hydroxide (TMAH) and thonzonium bromide. Other useful anionic surfactants include bio-based anionic surfactants, including, without limitation, STEPONOL® AM 30-KE, an ammonium lauryl sulfate, and STEPONOL® EHS, a sodium 2-ethyl hexyl sulfate. Such bio-based surfactants are not synthetic molecules, but instead are anionic biosurfactants derived from organic matter such as plants.

Zwitterionic surfactants are based on primary, secondary or tertiary amines or quaternary ammonium cation with a sulfonate, a carboxylate, or a phosphate. Zwitterionic surfactants include, without limitation, 3-[(3-Cholamidopropyl)dimethylammonio]-1-propanesulfonate (CHAPS); sultaines like cocamidopropyl hydroxysultaine; betaines like cocamidopropyl betaine; or lecithins.

Non-ionic surfactants are less denaturing and as such are useful to solubilize membrane proteins and lipids while retaining protein-protein interactions. Nonionic surfactants include polyether nonionic surfactants, polyhydroxyl nonionic surfactants and biosurfactants. Nonionic surfactants include alcohol ethoxylates, alkylphenol ethoxylates, phenol ethoxylates, amide ethoxylates, glyceride ethoxylates, fatty acid ethoxylates, fatty amine ethoxylates and polyethoxylated tallow amine (POEA). Other useful non-ionic surfactants include bio-based non-ionic surfactants, including, without limitation, STEPOSOL® MET-10U, a metathesis-derived, nonionic surfactant that is an unsaturated, short chain amide. Such bio-based surfactants are not synthetic molecules, but instead are non-ionic biosurfactants derived from organic matter such as plants.

Non-limiting examples of surfactants include polyoxyethylene glycol sorbitan alkyl esters (or ethoxylated sorbital esters) like polysorbate 20 sorbitan monooleate (TWEEN® 20), polysorbate 40 sorbitan monooleate (TWEEN® 40), polysorbate 60 sorbitan monooleate (TWEEN® 60), polysorbate 61 sorbitan monooleate (TWEEN® 61), polysorbate 65 sorbitan monooleate (TWEEN® 65), polysorbate 80 sorbitan monooleate (TWEEN® 80), polysorbate 81 sorbitan monooleate (TWEEN® 81) and polysorbate 85 sorbitan monooleate (TWEEN® 85); sorbital esters like sorbitan monooleate, sorbitan monolaurate, sorbitan monopalmitate, sorbitan monostearate and sorbitan tristearate; polyglycerol esters like glycerol monooleate, glycerol monolaurate, glycerol monopalmitate, glycerol monostearate, glycerol trioleate, glycerol ricinoleate, glycerol tristearate, mono diglycerides and glycerol triacetate; ethoxylated polyglycerol esters; alkyl glucosides like arachidyl glucoside, $C_{12-20}$ alkyl glucoside, caprylyl/capryl glucoside, cetearyl glucoside, coco-glucoside, ethyl glucoside and lauryl glucoside. decyl glucoside; ethoxylated alkyl glucosides; sucrose esters like sucrose monooleate, sucrose monolaurate, sucrose monopalmitate, sucrose monostearate, sucrose trioleate, sucrose ricinoleate, sucrose tristearate, sucrose diglycerides and sucrose triacetate; ethoxylated sucrose ester; amine oxides; ethoxylated alcohols; ethoxylated aliphatic alcohols; alkylamines; ethoxylated alkylamines; ethoxylated alkyl phenols like ethoxylated nonyl phenol and ethoxylated octyl phenol; alkyl polysaccharides; ethoxylated alkyl polysaccharides; ethoxylated fatty acids like ethoxylated castor oil; ethoxylated fatty alcohols like ethoxylated ceto-oleyl alcohol, ethoxylated ceto-stearyl alcohol, ethoxylated decyl alcohol, ethoxylated dodecyl alcohol and ethoxylated tridecyl alcohol; ethoxylated fatty amines; poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), and Poloxamer 407 (PLURONIC® F127); linear secondary alcohol ethoxylates like TERGITOL™ 15-S-5, TERGITOL™ 15-S-7, TERGITOL™ 15-S-9, TERGITOL™ 15-S-12, TERGITOL™ 15-S-15, TERGITOL™ 15-S-20, TERGITOL™ 15-S-30 and TERGITOL™ 15-S-40; alkyl phenol polyglycol ethers; polyethylene glycol alkyl aryl ethers; polyoxyethylene glycol alkyl ethers, like octaethylene glycol monododecyl ether, pentaethylene glycol monododecyl ether, BRIJ® 30, and BRIJ® 35; 2-dodecoxyethanol (LUBROL®-PX); polyoxyethylene glycol octylphenol ethers like polyoxyethylene (4-5) p-t-octyl phenol (TRITON® X-45) and polyoxyethylene octyl phenyl ether (TRITON® X-100); polyoxyethylene glycol alkylphenol ethers like Nonoxynol-9; phenoxypolyethoxylethanols like nonylphenoxypolyethoxylethanol and octylphenoxypolyethoxylethanol (IGEPAL® CA-630 or NONIDET™ P-40); glucoside alkyl ethers like octyl glucopyranoside; maltoside alkyl ethers like dodecyl maltopyranoside; thioglucoside alkyl ethers like heptyl thioglucopyranoside; digitonins; glycerol alkyl esters like glyceryl laurate; alkyl aryl polyether sulfates; alcohol sulfonates; sorbitan alkyl esters; cocamide ethanolamines like cocamide monoethanolamine and cocamide diethanolamine; sucrose monolaurate; dodecyl dimethylamine oxide, and sodium cholate. Other non-limiting examples of surfactants useful in the methods disclosed herein can be found in, e.g., Winslow, et al., Methods and Compositions for Simultaneously Isolating Hemoglobin from Red Blood Cells and Inactivating Viruses, U.S. 2008/0138790; Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

In one embodiment, a single surfactant is present in a composition disclosed herein. In another embodiment, a plurality of surfactants is present in a composition disclosed herein. In aspects of this embodiment, a composition disclosed herein comprises, e.g., one or more surfactants, two or more surfactants, three or more surfactants, four or more surfactants or five or more surfactants. In other aspects of this embodiment, a composition disclosed herein comprises, e.g., only one surfactant, at most two surfactants, at most three surfactants, at most four surfactants, or at most five surfactants. In yet other aspects of this embodiment, a composition disclosed herein comprises from, e.g., 1 to 2 surfactants, 1 to 3 surfactants, 1 to 4 surfactants, 1 to 5 surfactants, 2 to 3 surfactants, 2 to 4 surfactants, 2 to 5 surfactants, 3 to 4 surfactants, 3 to 5 surfactants or 4 to 5 surfactants.

Any amount of a surfactant disclosed herein may be used, with the proviso that the amount is useful to practice the methods disclosed herein. In aspects of this embodiment, a composition disclosed herein comprises a surfactant in an amount of, e.g., about 0.001%, about 0.005%, about 0.0075%, about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition. In other aspects of this embodiment, a composition disclosed herein comprises a surfactant in an amount of, e.g., at least 0.001%, at least 0.005%, at least 0.0075%, at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0% by weight of the composition. In yet other aspects of this embodiment, a composition disclosed herein comprises a surfactant in an amount of, e.g., at most 0.001%, at most 0.005%, at most 0.0075%, at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition.

In still other aspects of this embodiment, a composition disclosed herein comprises a surfactant in an amount of, e.g., about 0.001% to about 0.005%, about 0.001% to about 0.0075%, about 0.001% to about 0.01%, about 0.001% to about 0.025%, about 0.001% to about 0.05%, about 0.001% to about 0.075%, about 0.001% to about 0.1%, about 0.001% to about 0.25%, about 0.001% to about 0.75%, about 0.001% to about 1.0%, about 0.005% to about 0.0075%, about 0.005% to about 0.01%, about 0.005% to about 0.025%, about 0.005% to about 0.05%, about 0.005% to about 0.075%, about 0.005% to about 0.1%, about 0.005% to about 0.25%, about 0.005% to about 0.75%, about 0.005% to about 1.0%, about 0.01% to about 0.05%, about 0.01% to about 0.075%, about 0.01% to about 0.1%, about 0.01% to about 0.25%, about 0.01% to about 0.5%, about 0.01% to about 0.75%, about 0.01% to about 1.0%, about 0.01% to about 1.5%, about 0.01% to about 2.0%, about 0.01% to about 2.5%, about 0.05% to about 0.075%, about 0.05% to about 0.1%, about 0.05% to about 0.25%, about 0.05% to about 0.5%, about 0.05% to about 0.75%, about 0.05% to about 1.0%, about 0.05% to about 1.5%, about 0.05% to about 2.0%, about 0.05% to about 2.5%, about 0.1% to about 0.5%, about 0.1% to about 0.75%, about 0.1% to about 1.0%, about 0.1% to about 1.5%, about 0.1% to about 2.0%, about 0.1% to about 2.5%, about 0.1% to about 3.0%, about 0.1% to about 4.0%, about 0.1% to about 5.0%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.2% to about 3.0%, about 0.2% to about 4.0%, about 0.2% to about 5.0%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0%, about 5.0% to about 15.0%, about 6.0% to about 7.0%, about 6.0% to about 7.5%, about 6.0% to about 8.0%, about 6.0% to about 9.0%, about 6.0% to about 10.0%, about 6.0% to about 11.0%, about 6.0% to about 12.0%, about 6.0% to about 13.0%, about 6.0% to about 14.0% or about 6.0% to about 15.0% by weight of the composition.

In another embodiment, a composition disclosed herein does not comprise a surfactant.

A preservative preserves the stability of a composition disclosed herein. A preservatives can also prevent the growth of microbial organisms in a composition disclosed herein. Non-limiting examples of a preservative include methylparaben, phenoxyethanol, capryl glycol, glyceryl caprylate, benzoic acid, sorbic acid, gallic acid, and propylparaben.

A composition disclosed herein may be adjusted to any pH that enables a composition disclosed herein to achieve a desired beneficial effect. In aspects of this embodiment, the pH of a composition disclosed herein is, e.g., at least 2, at least 3, at least 4, at least 5, at least 6, at least 7, at least 8, at least 9, at least 10, or at least 11. In other aspects of this embodiment, the pH of a composition disclosed herein is, e.g., at most 2, at most 3, at most 4, at most 5, at most 6, at most 7, at most 8, at most 9, at most 10, or at most 11.

In yet other aspects of this embodiment, the pH of a composition disclosed herein is between, e.g., about 2 to about 5, about 2 to about 5.5, about 2 to about 6, about 2 to about 6.5, about 2 to about 7, about 2 to about 7.5, about 2 to about 8, about 2 to about 8.5, about 2 to about 9, about 2.5 to about 5, about 2.5 to about 5.5, about 2.5 to about 6, about 2.5 to about 6.5, about 2.5 to about 7, about 2.5 to about 7.5, about 2.5 to about 8, about 2.5 to about 8.5, about 2.5 to about 9, about 3 to about 5, about 3 to about 5.5, about 3 to about 6, about 3 to about 6.5, about 3 to about 7, about 3 to about 7.5, about 3 to about 8, about 3 to about 8.5, about 3 to about 9, about 3.5 to about 5, about 3.5 to about 5.5, about 3.5 to about 6, about 3.5 to about 6.5, about 3.5 to about 7, about 3.5 to about 7.5, about 3.5 to about 8, about 3.5 to about 8.5, about 3.5 to about 9, about 4 to about 5, about 4 to about 5.5, about 4 to about 6, about 4 to about 6.5, about 4 to about 7, about 4 to about 7.5, about 4 to about 8, about 4 to about 8.5, about 4 to about 9, about 4.5 to about 5, about 4.5 to about 5.5, about 4.5 to about 6, about 4.5 to about 6.5, about 4.5 to about 7, about 4.5 to about 7.5, about 4.5 to about 8, about 4.5 to about 8.5, about 4.5 to about 9, about 5 to about 5.5, about 5 to about 6, about 5 to about 6.5, about 5 to about 7, about 5 to about 7.5, about 5 to about 8, about 5 to about 8.5, about 5 to about 9, about 5.5 to about 6, about 5.5 to about 6.5, about 5.5 to about 7, about 5.5 to about 7.5, about 5.5 to about 8, about 5.5 to about 8.5, about 5.5 to about 9, about 6 to about 6.5, about 6 to about 7, about 6 to about 7.5, about 6 to about 8, about 6 to about 8.5, about 6 to about 9, about 6.5 to about 7, about 6.5 to about 7.5, about 6.5 to about 8, about 6.5 to about 8.5, about 6.5 to about 9, about 7 to about 7.5, about 7 to about 8, about 7 to about 8.5, about 7 to about 9, about 7.5 to about 8, about 7.5 to about 8.5, about 7.5 to about 9, about 8 to about 8.5, about 8 to about 9, or about 8.5 to about 9.

In still other aspects of this embodiment, the pH of a composition disclosed herein is between, e.g., about 6 to about 8, about 6.7 to about 7.7, about 6.8 to about 7.6, about 6.9 to about 7.5, about 7.0 to about 7.4, about 7.1 to about 7.3, or about 7.2. In an aspect of this embodiment, a composition disclosed herein is between, e.g., about 6 to about 8, about 6.7 to about 7.7, about 6.8 to about 7.6, about 6.9 to about 7.5, about 7.0 to about 7.4, about 7.1 to about 7.3, or about 7.2. In another embodiment, the pH of a composition disclosed herein is between, e.g., about 5.0 to about 6.5, about 5.2 to about 6.2, about 5.3 to about 6.1, about 5.4 to about 6.0, about 5.5 to about 5.9, about 5.6 to about 5.8, or about 5.7. In an aspect of this embodiment, a composition disclosed herein is between, e.g., about 5.0 to about 6.5, about 5.2 to about 6.2, about 5.3 to about 6.1, about 5.4 to about 6.0, about 5.5 to about 5.9, about 5.6 to about 5.8, or about 5.7.

A composition disclosed herein is stable. In one embodiment, a composition disclosed herein is stable when it shows, e.g., at most 1% degradation, at most 2% degradation, at most 3% degradation, at most 4% degradation, at most 5% degradation, at most 6% degradation, at most 7% degradation, at most 8% degradation, at most 9% degradation, or at most 10% degradation of hypochlorous acid. In another embodiment, a composition disclosed herein is stable when it shows, e.g., at most 10% degradation, at most 15% degradation, at most 20% degradation, at most 25% degradation, at most 30% degradation, at most 35% degradation, at most 40% degradation, at most 45% degradation, at most 50% degradation, at most 55% degradation, at most 60% degradation, at most 65% degradation, at most 70% degradation, at most 75% degradation, at most 80% degradation, at most 85% degradation, at most 90% degradation, or at most 95% degradation of hypochlorous acid. In another embodiment, a composition disclosed herein is stable when it shows, e.g., about 1% to about 10% degradation, about 1% to about 20% degradation, about 1% to about 30% degradation, about 1% to about 40% degradation, about 1% to about 50% degradation, about 1% to about 60% degradation, about 1% to about 70% degradation, about 1% to about 80% degradation, about 1% to about 90% degradation, about 1% to about 95% degradation, about 5% to about 10% degradation, about 5% to about 20% degradation, about 5% to about 30% degradation, about 5% to about 40% degradation, about 5% to about 50% degradation, about 5% to about 60% degradation, about 5% to about 70% degradation, about 5% to about 80% degradation, about 5% to about 90% degradation, about 5% to about 95% degradation, about 10% to about 20% degradation, about 10% to about 30% degradation, about 10% to about 40% degradation, about 10% to about 50% degradation, about 10% to about 60% degradation, about 10% to about 70% degradation, about 10% to about 80% degradation, about 10% to about 90% degradation, about 10% to about 95% degradation, 20% to about 30% degradation, about 20% to about 40% degradation, about 20% to about 50% degradation, about 20% to about 60% degradation, about 20% to about 70% degradation, about 20% to about 80% degradation, about 20% to about 90% degradation, about 20% to about 95% degradation, about 30% to about 40% degradation, about 30% to about 50% degradation, about 30% to about 60% degradation, about 30% to about 70% degradation, about 30% to about 80% degradation, about 30% to about 90% degradation, about 30% to about 95% degradation, about 40% to about 50% degradation, about 40% to about 60% degradation, about 40% to about 70% degradation, about 40% to about 80% degradation, about 40% to about 90% degradation, about 40% to about 95% degradation, about 50% to about 60% degradation, about 50% to about 70% degradation, about 50% to about 80% degradation, about 50% to about 90% degradation, about 50% to about 95% degradation, about 60% to about 70% degradation, about 60% to about 80% degradation, about 60% to about 90% degradation, about 60% to about 95% degradation, about 70% to about 80% degradation, about 70% to about 90% degradation, about 70% to about 95% degradation, about 80% to about 90% degradation, about 80% to about 95% degradation, or about 90% to about 95% degradation of hypochlorous acid.

In one embodiment, a composition disclosed herein is stable when it shows, e.g., at most 1% degradation, at most 2% degradation, at most 3% degradation, at most 4% degradation, at most 5% degradation, at most 6% degradation, at most 7% degradation, at most 8% degradation, at most 9% degradation, or at most 10% degradation of free available chlorine. In another embodiment, a composition disclosed herein is stable when it shows, e.g., at most 10% degradation, at most 15% degradation, at most 20% degradation, at most 25% degradation, at most 30% degradation, at most 35% degradation, at most 40% degradation, at most 45% degradation, at most 50% degradation, at most 55% degradation, at most 60% degradation, at most 65% degradation, at most 70% degradation, at most 75% degradation, at most 80% degradation, at most 85% degradation, at most 90% degradation, or at most 95% degradation of free available chlorine. In another embodiment, a composition disclosed herein is stable when it shows, e.g., about 1% to about 10% degradation, about 1% to about 20% degradation, about 1% to about 30% degradation, about 1% to about 40% degradation, about 1% to about 50% degradation, about 1% to about 60% degradation, about 1% to about 70% degradation, about 1% to about 80% degradation, about 1% to about 90% degradation, about 1% to about 95% degradation, about 5% to about 10% degradation, about 5% to about 20% degradation, about 5% to about 30% degradation, about 5% to about 40% degradation, about 5% to about 50% degradation, about 5% to about 60% degradation, about 5% to about 70% degradation, about 5% to about 80% degradation, about 5% to about 90% degradation, about 5% to about 95% degradation, about 10% to about 20% degradation, about 10% to about 30% degradation, about 10% to about 40% degradation, about 10% to about 50% degradation, about 10% to about 60% degradation, about 10% to about 70% degradation, about 10% to about 80% degradation, about 10% to about 90% degradation, about 10% to about 95% degradation, 20% to about 30% degradation, about 20% to about 40% degradation, about 20% to about 50% degradation, about 20% to about 60% degradation, about 20% to about 70% degradation, about 20% to about 80% degradation, about 20% to about 90% degradation, about 20% to about 95% degradation, about 30% to about 40% degradation, about 30% to about 50% degradation, about 30% to about 60% degradation, about 30% to about 70% degradation, about 30% to about 80% degradation, about 30% to about 90% degradation, about 30% to about 95% degradation, about 40% to about 50% degradation, about 40% to about 60% degradation, about 40% to about 70% degradation, about 40% to about 80% degradation, about 40% to about 90% degradation, about 40% to about 95% degradation, about 50% to about 60% degradation, about 50% to about 70% degradation, about 50% to about 80% degradation, about 50% to about 90% degradation, about 50% to about 95% degradation, about 60% to about 70% degradation, about 60% to about 80% degradation, about 60% to about 90% degradation, about 60% to about 95% degradation, about 70% to about 80% degradation, about 70% to about 90% degradation, about 70% to about 95% degradation, about 80% to about 90% degradation, about 80% to about 95% degradation, or about 90% to about 95% degradation of free available chlorine.

In aspects of this embodiment, a composition disclosed herein is stable for, e.g., about 1 day, about 2 days, 3 days, 4 days, 5 days, 6, days, 7 days, 8 days, 9 days, 10 days, 11 days, 12 days, 13 days, 14 days or 15 days. In other aspects of this embodiment, a composition disclosed herein is stable for, e.g., at least 1 day, at least 2 days, at least 3 days, at least 4 days, at least 5 days, at least 6, days, at least 7 days, at least 8 days, at least 9 days, at least 10 days, at least 11 days, at least 12 days, at least 13 days, at least 14 days or at least 15 days. In yet other aspects of this embodiment, a composition disclosed herein is stable for, e.g., at most 1 day, at most 2 days, at most 3 days, at most 4 days, at most 5 days, at most 6, days, at most 7 days, at most 8 days, at most 9 days, at most 10 days, at most 11 days, at most 12 days, at most 13 days, at most 14 days or at most 15 days.

In still aspects of this embodiment, a composition disclosed herein is stable for, e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 1 day to about 12 days, about 1 day to about 13 days, about 1 day to about 14 days, about 1 day to about 15 days, about 2 days to about 3 days, about 2 days to about 4 days, about 2 days to about 5 days, about 2 days to about 6 days, about 2 days to about 7 days, about 2 days to about 8 days, about 2 days to about 9 days, about 2 days to about 10 days, about 2 days to about 11 days, about 2 days to about 12 days, about 2 days to about 13 days, about 2 days to about 14 days, about 2 days to about 15 days, about 3 days to about 4 days, about 3 days to about 5 days, about 3 days to about 6 days, about 3 days to about 7 days, about 3 days to about 8 days, about 3 days to about 9 days, about 3 days to about 10 days, about 3 days to about 11 days, about 3 days to about 12 days, about 3 days to about 13 days, about 3 days to about 14 days, about 3 days to about 15 days, about 4 days to about 5 days, about 4 days to about 6 days, about 4 days to about 7 days, about 4 days to about 8 days, about 4 days to about 9 days, about 4 days to about 10 days, about 4 days to about 11 days, about 4 days to about 12 days, about 4 days to about 13 days, about 4 days to about 14 days, about 4 days to about 15 days, about 5 days to about 6 days, about 5 days to about 7 days, about 5 days to about 8 days, about 5 days to about 9 days, about 5 days to about 10 days, about 5 days to about 11 days, about 5 days to about 12 days, about 5 days to about 13 days, about 5 days to about 14 days, about 5 days to about 15 days, about 6 days to about 7 days, about 6 days to about 8 days, about 6 days to about 9 days, about 6 days to about 10 days, about 6 days to about 11 days, about 6 days to about 12 days, about 6 days to about 13 days, about 6 days to about 14 days, about 6 days to about 15 days, about 7 days to about 8 days, about 7 days to about 9 days, about 7 days to about 10 days, about 7 days to about 11 days, about 7 days to about 12 days, about 7 days to about 13 days, about 7 days to about 14 days, about 7 days to about 15 days, about 8 days to about 9 days, about 8 days to about 10 days, about 8 days to about 11 days, about 8 days to about 12 days, about 8 days to about 13 days, about 8 days to about 14 days, about 8 days to about 15 days, about 9 days to about 10 days, about 9 days to about 11 days, about 9 days to about 12 days, about 9 days to about 13 days, about 9 days to about 14 days, about 9 days to about 15 days, about 10 days to about 11 days, about 10 days to about 12 days, about 10 days to about 13 days, about 10 days to about 14 days, about 10 days to about 15 days, about 11 days to about 12 days, about 11 days to about 13 days, about 11 days to about 14 days, about 11 days to about 15 days, about 12 days to about 13 days, about 12 days to about 14 days, about 12 days to about 15 days, about 13 days to about 14 days, about 13 days to about 15 days, or about 14 days to about 15 days.

In other aspects of this embodiment, a composition disclosed herein is stable for, e.g., about 1 week, about 2 weeks, 3 weeks, 4 weeks, 5 weeks, 6, weeks, 7 weeks, 8 weeks, 9 weeks, 10 weeks, 11 weeks, 12 weeks, 13 weeks, 14 weeks or 15 weeks. In yet other aspects of this embodiment, a composition disclosed herein is stable for, e.g., at least 1 week, at least 2 weeks, at least 3 weeks, at least 4 weeks, at least 5 weeks, at least 6, weeks, at least 7 weeks, at least 8 weeks, at least 9 weeks, at least 10 weeks, at least 11 weeks, at least 12 weeks, at least 13 weeks, at least 14 weeks or at least 15 weeks. In still other aspects of this embodiment, a composition disclosed herein is stable for, e.g., at most 1 week, at most 2 weeks, at most 3 weeks, at most 4 weeks, at most 5 weeks, at most 6, weeks, at most 7 weeks, at most 8 weeks, at most 9 weeks, at most 10 weeks, at most 11 weeks, at most 12 weeks, at most 13 weeks, at most 14 weeks or at most 15 weeks.

In aspects of this embodiment, a composition disclosed herein is stable for, e.g., about 1 week to about 2 weeks, about 1 week to about 3 weeks, about 1 week to about 4 weeks, about 1 week to about 5 weeks, about 1 week to about 6 weeks, about 1 week to about 7 weeks, about 1 week to about 8 weeks, about 1 week to about 9 weeks, about 1 week to about 10 weeks, about 1 week to about 11 weeks, about 1 week to about 12 weeks, about 1 week to about 13 weeks, about 1 week to about 14 weeks, about 1 week to about 15 weeks, about 2 weeks to about 3 weeks, about 2 weeks to about 4 weeks, about 2 weeks to about 5 weeks, about 2 weeks to about 6 weeks, about 2 weeks to about 7 weeks, about 2 weeks to about 8 weeks, about 2 weeks to about 9 weeks, about 2 weeks to about 10 weeks, about 2 weeks to about 11 weeks, about 2 weeks to about 12 weeks, about 2 weeks to about 13 weeks, about 2 weeks to about 14 weeks, about 2 weeks to about 15 weeks, about 3 weeks to about 4 weeks, about 3 weeks to about 5 weeks, about 3 weeks to about 6 weeks, about 3 weeks to about 7 weeks, about 3 weeks to about 8 weeks, about 3 weeks to about 9 weeks, about 3 weeks to about 10 weeks, about 3 weeks to about 11 weeks, about 3 weeks to about 12 weeks, about 3 weeks to about 13 weeks, about 3 weeks to about 14 weeks, about 3 weeks to about 15 weeks, about 4 weeks to about 5 weeks, about 4 weeks to about 6 weeks, about 4 weeks to about 7 weeks, about 4 weeks to about 8 weeks, about 4 weeks to about 9 weeks, about 4 weeks to about 10 weeks, about 4 weeks to about 11 weeks, about 4 weeks to about 12 weeks, about 4 weeks to about 13 weeks, about 4 weeks to about 14 weeks, about 4 weeks to about 15 weeks, about 5 weeks to about 6 weeks, about 5 weeks to about 7 weeks, about 5 weeks to about 8 weeks, about 5 weeks to about 9 weeks, about 5 weeks to about 10 weeks, about 5 weeks to about 11 weeks, about 5 weeks to about 12 weeks, about 5 weeks to about 13 weeks, about 5 weeks to about 14 weeks, about 5 weeks to about 15 weeks, about 6 weeks to about 7 weeks, about 6 weeks to about 8 weeks, about 6 weeks to about 9 weeks, about 6 weeks to about 10 weeks, about 6 weeks to about 11 weeks, about 6 weeks to about 12 weeks, about 6 weeks to about 13 weeks, about 6 weeks to about 14 weeks, about 6 weeks to about 15 weeks, about 7 weeks to about 8 weeks, about 7 weeks to about 9 weeks, about 7 weeks to about 10 weeks, about 7 weeks to about 11 weeks, about 7 weeks to about 12 weeks, about 7 weeks to about 13 weeks, about 7 weeks to about 14 weeks, about 7 weeks to about 15 weeks, about 8 weeks to about 9 weeks, about 8 weeks to about 10 weeks, about 8 weeks to about 11 weeks, about 8 weeks to about 12 weeks, about 8 weeks to about 13 weeks, about 8 weeks to about 14 weeks, about 8 weeks to about 15 weeks, about 9 weeks to about 10 weeks, about 9 weeks to about 11 weeks, about 9 weeks to about 12 weeks, about 9 weeks to about 13 weeks, about 9 weeks to about 14 weeks, about 9 weeks to about 15 weeks, about 10 weeks to about 11 weeks, about 10 weeks to about 12 weeks, about 10 weeks to about 13 weeks, about 10 weeks to about 14 weeks, about 10 weeks to about 15 weeks, about 11 weeks to about 12 weeks, about 11 weeks to about 13 weeks, about 11 weeks to about 14 weeks, about 11 weeks to about 15 weeks, about 12 weeks to about 13 weeks, about 12 weeks to about 14 weeks, about 12 weeks to about 15 weeks, about 13 weeks to about 14 weeks, about 13 weeks to about 15 weeks, or about 14 weeks to about 15 weeks.

In other aspects of this embodiment, a composition disclosed herein is stable for, e.g., about 1 month, about 2 months, 3 months, 4 months, 5 months, 6, months, 7 months, 8 months, 9 months, 10 months, 11 months, 12 months, 13 months, 14 months, 15 months, 16 months, 17 months, or 18 months. In yet other aspects of this embodiment, a composition disclosed herein is stable for, e.g., at least 1 month, at least 2 months, at least 3 months, at least 4 months, at least 5 months, at least 6, months, at least 7 months, at least 8 months, at least 9 months, at least 10 months, at least 11 months, at least 12 months, at least 13 months, at least 14 months, at least 15 months, at least 16 months, at least 17 months, or at least 18 months. In still other aspects of this embodiment, a composition disclosed herein is stable for, e.g., at most 1 month, at most 2 months, at most 3 months, at most 4 months, at most 5 months, at most 6, months, at most 7 months, at most 8 months, at most 9 months, at most 10 months, at most 11 months, at most 12 months, at most 13 months, at most 14 months, at most 15 months, at le most ast 16 months, at most 17 months, or at most 18 months.

In aspects of this embodiment, a composition disclosed herein is stable for, e.g., about 1 month to about 2 months, about 1 month to about 3 months, about 1 month to about 4 months, about 1 month to about 5 months, about 1 month to about 6 months, about 1 month to about 7 months, about 1 month to about 8 months, about 1 month to about 9 months, about 1 month to about 10 months, about 1 month to about 11 months, about 1 month to about 12 months, about 1 month to about 13 months, about 1 month to about 14 months, about 1 month to about 15 months, about 1 month to about 16 months, about 1 month to about 17 months, about 1 month to about 18 months, about 2 months to about 3 months, about 2 months to about 4 months, about 2 months to about 5 months, about 2 months to about 6 months, about 2 months to about 7 months, about 2 months to about 8 months, about 2 months to about 9 months, about 2 months to about 10 months, about 2 months to about 11 months, about 2 months to about 12 months, about 2 months to about 13 months, about 2 months to about 14 months, about 2 months to about 15 months, about 2 months to about 16 months, about 2 months to about 17 months, about 2 months to about 18 months, about 3 months to about 4 months, about 3 months to about 5 months, about 3 months to about 6 months, about 3 months to about 7 months, about 3 months to about 8 months, about 3 months to about 9 months, about 3 months to about 10 months, about 3 months to about 11 months, about 3 months to about 12 months, about 3 months to about 13 months, about 3 months to about 14 months, about 3 months to about 15 months, about 3 months to about 16 months, about 3 months to about 17 months, about 3 months to about 18 months, about 4 months to about 5 months, about 4 months to about 6 months, about 4 months to about 7 months, about 4 months to about 8 months, about 4 months to about 9 months, about 4 months to about 10 months, about 4 months to about 11 months, about 4 months to about 12 months, about 4 months to about 13 months, about 4 months to about 14 months, about 4 months to about 15 months, about 4 months to about 16 months, about 4 months to about 17 months, about 4 months to about 18 months, about 5 months to about 6 months, about 5 months to about 7 months, about 5 months to about 8 months, about 5 months to about 9 months, about 5 months to about 10 months, about 5 months to about 11 months, about 5 months to about 12 months, about 5 months to about 13 months, about 5 months to about 14 months, about 5 months to about 15 months, about 5 months to about 16 months, about 5 months to about 17 months, about 5 months to about 18 months, about 6 months to about 7 months, about 6 months to about 8 months, about 6 months to about 9 months, about 6 months to about 10 months, about 6 months to about 11 months, about 6 months to about 12 months, about 6 months to about 13 months, about 6 months to about 14 months, about 6 months to about 15 months, about 6 months to about 16 months, about 6 months to about 17 months, about 6 months to about 18 months, about 7 months to about 8 months, about 7 months to about 9 months, about 7 months to about 10 months, about 7 months to about 11 months, about 7 months to about 12 months, about 7 months to about 13 months, about 7 months to about 14 months, about 7 months to about 15 months, about 7 months to about 16 months, about 7 months to about 17 months, about 7 months to about 18 months, about 8 months to about 9 months, about 8 months to about 10 months, about 8 months to about 11 months, about 8 months to about 12 months, about 8 months to about 13 months, about 8 months to about 14 months, about 8 months to about 15 months, about 8 months to about 16 months, about 8 months to about 17 months, about 8 months to about 18 months, about 9 months to about 10 months, about 9 months to about 11 months, about 9 months to about 12 months, about 9 months to about 13 months, about 9 months to about 14 months, about 9 months to about 15 months, about 9 months to about 16 months, about 9 months to about 17 months, about 9 months to about 18 months, about 10 months to about 11 months, about 10 months to about 12 months, about 10 months to about 13 months, about 10 months to about 14 months, about 10 months to about 15 months, about 10 months to about 16 months, about 10 months to about 17 months, about 10 months to about 18 months, about 11 months to about 12 months, about 11 months to about 13 months, about 11 months to about 14 months, about 11 months to about 15 months, about 11 months to about 16 months, about 11 months to about 17 months, about 1 months to about 18 months, about 12 months to about 13 months, about 12 months to about 14 months, about 12 months to about 15 months, about 12 months to about 16 months, about 12 months to about 17 months, about 12 months to about 18 months, about 13 months to about 14 months, about 13 months to about 15 months, about 13 months to about 16 months, about 13 months to about 17 months, about 13 months to about 18 months, about 14 months to about 15 months, about 14 months to about 16 months, about 14 months to about 17 months, about 14 months to about 18 months, about 15 months to about 16 months, about 15 months to about 17 months, about 15 months to about 18 months, about 16 months to about 17 months, about 16 months to about 18 months, or about 17 months to about 18 months.

In other aspects of this embodiment, a composition disclosed herein is stable for, e.g., about 1 year, about 2 years, about 3 years, about 4 years, or about 5 years. In yet other aspects of this embodiment, a composition disclosed herein is stable for, e.g., at least 1 year, at least 2 years, at least 3 years, at least 4 years, or at least 5 years. In still other aspects of this embodiment, a composition disclosed herein is stable for, e.g., at most 1 year, at most 2 years, at most 3 years, at most 4 years, or at most 5 years. In other aspects of this embodiment, a composition disclosed herein is stable for, e.g., about 1 year to about 2 years, about 1 year to about 3 years, about 1 year to about 4 years, about 1 year to about 5 years, about 2 years to about 3 years, about 2 years to about 4 years, about 2 years to about 5 years, about 3 years to about 4 years, about 3 years to about 5 years, or about 4 years to about 5 years.

A composition disclosed herein can be formulated into any form that enables application of a composition disclosed herein in a manner that achieves a desired beneficial effect. In one embodiment, a composition disclosed herein can be formulated into, e.g., a single-phase formulation or a biphasic formulation comprising a medium phase and a dispersed phase. In another embodiment, a composition disclosed herein can be formulated into, e.g., a liquid composition, a colloidal composition, a semi-solid composition, or a solid composition. In another embodiment, a composition disclosed herein can be formulated into, e.g., a liquid aerosol, a foam, an emulsion, a gel, a sol, or a solid sol. In another embodiment, a composition disclosed herein can be formulated into, e.g., a spray, a liquid aerosol, a soap, or a suspension.

In an embodiment, a composition disclosed herein comprises about 80 ppm to about 115 ppm hypochlorous acid or free available chlorine and about 0.01% to about 0.5% of a dialdehyde. In aspects of this embodiment, a composition disclosed herein comprises about 85 ppm to about 110 ppm hypochlorous acid or free available chlorine and about 0.025% to about 0.4% of a dialdehyde. In other aspects of this embodiment, a composition disclosed herein comprises about 90 ppm to about 105 ppm hypochlorous acid or free available chlorine and about 0.05% to about 0.3% of a dialdehyde. In yet other aspects of this embodiment, a composition disclosed herein comprises about 95 ppm to about 100 ppm hypochlorous acid or free available chlorine and about 0.075% to about 0.2% of a dialdehyde. In still other aspects of this embodiment, a composition disclosed herein comprises about 97 ppm hypochlorous acid or free available chlorine and about 0.1% of a dialdehyde.

In an embodiment, a composition disclosed herein comprises about 80 ppm to about 115 ppm hypochlorous acid or free available chlorine and about 0.01% to about 0.5% glutaraldehyde. In aspects of this embodiment, a composition disclosed herein comprises about 85 ppm to about 110 ppm hypochlorous acid or free available chlorine and about 0.025% to about 0.4% glutaraldehyde. In other aspects of this embodiment, a composition disclosed herein comprises about 90 ppm to about 105 ppm hypochlorous acid or free available chlorine and about 0.05% to about 0.3% glutaraldehyde. In yet other aspects of this embodiment, a composition disclosed herein comprises about 95 ppm to about 100 ppm hypochlorous acid or free available chlorine and about 0.075% to about 0.2% glutaraldehyde. In still other aspects of this embodiment, a composition disclosed herein comprises about 97 ppm hypochlorous acid or free available chlorine and about 0.1% glutaraldehyde.

In an embodiment, a composition disclosed herein comprises about 80 ppm to about 115 ppm hypochlorous acid or free available chlorine and about 0.05% to about 0.6% of a dialdehyde. In aspects of this embodiment, a composition disclosed herein comprises about 85 ppm to about 110 ppm hypochlorous acid or free available chlorine and about 0.075% to about 0.5% of a dialdehyde. In other aspects of this embodiment, a composition disclosed herein comprises about 90 ppm to about 105 ppm hypochlorous acid or free available chlorine and about 0.1% to about 0.4% of a dialdehyde. In yet other aspects of this embodiment, a composition disclosed herein comprises about 95 ppm to about 100 ppm hypochlorous acid or free available chlorine and about 0.2% to about 0.3% of a dialdehyde. In still other aspects of this embodiment, a composition disclosed herein comprises about 97 ppm hypochlorous acid or free available chlorine and about 0.25% of a dialdehyde.

In an embodiment, a composition disclosed herein comprises about 80 ppm to about 115 ppm hypochlorous acid or free available chlorine and about 0.05% to about 0.6% glutaraldehyde. In aspects of this embodiment, a composition disclosed herein comprises about 85 ppm to about 110 ppm hypochlorous acid or free available chlorine and about 0.075% to about 0.5% glutaraldehyde. In other aspects of this embodiment, a composition disclosed herein comprises about 90 ppm to about 105 ppm hypochlorous acid or free available chlorine and about 0.1% to about 0.4% glutaraldehyde. In yet other aspects of this embodiment, a composition disclosed herein comprises about 95 ppm to about 100 ppm hypochlorous acid or free available chlorine and about 0.2% to about 0.3% glutaraldehyde. In still other aspects of this embodiment, a composition disclosed herein comprises about 97 ppm hypochlorous acid or free available chlorine and about 0.25% glutaraldehyde.

In an embodiment, a composition disclosed herein comprises about 80 ppm to about 115 ppm hypochlorous acid or free available chlorine and about 0.1% to about 1.0% of a dialdehyde. In aspects of this embodiment, a composition disclosed herein comprises about 85 ppm to about 110 ppm hypochlorous acid or free available chlorine and about 0.2% to about 0.8% of a dialdehyde. In other aspects of this embodiment, a composition disclosed herein comprises about 90 ppm to about 105 ppm hypochlorous acid or free available chlorine and about 0.3% to about 0.7% of a dialdehyde. In yet other aspects of this embodiment, a composition disclosed herein comprises about 95 ppm to about 100 ppm hypochlorous acid or free available chlorine and about 0.4% to about 0.6% of a dialdehyde. In still other aspects of this embodiment, a composition disclosed herein comprises about 97 ppm hypochlorous acid or free available chlorine and about 0.5% of a dialdehyde.

In an embodiment, a composition disclosed herein comprises about 80 ppm to about 115 ppm hypochlorous acid or free available chlorine and about 0.1% to about 1.0% glutaraldehyde. In aspects of this embodiment, a composition disclosed herein comprises about 85 ppm to about 110 ppm hypochlorous acid or free available chlorine and about 0.2% to about 0.8% glutaraldehyde. In other aspects of this embodiment, a composition disclosed herein comprises about 90 ppm to about 105 ppm hypochlorous acid or free available chlorine and about 0.3% to about 0.7% glutaraldehyde. In yet other aspects of this embodiment, a composition disclosed herein comprises about 95 ppm to about 100 ppm hypochlorous acid or free available chlorine and about 0.4% to about 0.6% glutaraldehyde. In still other aspects of this embodiment, a composition disclosed herein comprises about 97 ppm hypochlorous acid or free available chlorine and about 0.5% glutaraldehyde.

In an embodiment, a composition disclosed herein comprises about 4% to about 12% of biguanide-containing compound, about 60% to about 80% of an alcohol and about 0.1% to about 5.0% of a dialdehyde. In aspects of this embodiment, a composition disclosed herein comprises about 5% to about 11% of biguanide-containing compound, about 62% to about 78% of an alcohol and about 0.5% to about 3.5% of a dialdehyde. In other aspects of this embodiment, a composition disclosed herein comprises about 6% to about 10% of biguanide-containing compound, about 65% to about 75% of an alcohol and about 1.0% to about 3.0% of a dialdehyde. In yet other aspects of this embodiment, a composition disclosed herein comprises about 7% to about 9% of biguanide-containing compound, about 67% to about 73% of an alcohol and about 1.5% to about 2.5% of a dialdehyde. In still other aspects of this embodiment, a composition disclosed herein comprises about 8% of biguanide-containing compound, about 70% of an alcohol and about 2.0% of a dialdehyde.

In an embodiment, a composition disclosed herein comprises about 4% to about 12% polyhexamethylene biguanide, about 60% to about 80% of isopropanol and about 0.1% to about 5.0% of glutaraldehyde. In aspects of this embodiment, a composition disclosed herein comprises about 5% to about 11% polyhexamethylene biguanide, about 62% to about 78% of isopropanol and about 0.5% to about 3.5% of glutaraldehyde. In other aspects of this embodiment, a composition disclosed herein comprises about 6% to about 10% polyhexamethylene biguanide, about 65% to about 75% of isopropanol and about 1.0% to about 3.0% of glutaraldehyde. In yet other aspects of this embodiment, a composition disclosed herein comprises about 7% to about 9% polyhexamethylene biguanide, about 67% to about 73% of isopropanol and about 1.5% to about 2.5% of glutaraldehyde. In still other aspects of this embodiment, a composition disclosed herein comprises about 8% polyhexamethylene biguanide, about 70% of isopropanol and about 2.0% of glutaraldehyde.

In an embodiment, a composition disclosed herein comprises about 5% to about 15% of biguanide-containing compound, about 60% to about 80% of an alcohol and about 0.1% to about 1.0% of a dialdehyde. In aspects of this embodiment, a composition disclosed herein comprises about 6.5% to about 12.5% of biguanide-containing compound, about 62% to about 78% of an alcohol and about 0.2% to about 0.8% of a dialdehyde. In other aspects of this embodiment, a composition disclosed herein comprises about 7.5% to about 11.5% of biguanide-containing compound, about 65% to about 75% of an alcohol and about 0.3% to about 0.7% of a dialdehyde. In yet other aspects of this embodiment, a composition disclosed herein comprises about 8.5% to about 10.5% of biguanide-containing compound, about 67% to about 73% of an alcohol and about 0.4% to about 0.6% of a dialdehyde. In still other aspects of this embodiment, a composition disclosed herein comprises about 9.5% of biguanide-containing compound, about 70% of an alcohol and about 0.5% of a dialdehyde.

In an embodiment, a composition disclosed herein comprises about 5% to about 15% polyhexamethylene biguanide, about 60% to about 80% of isopropanol and about 0.1% to about 1.0% of ortho-phthalaldehyde. In aspects of this embodiment, a composition disclosed herein comprises about 6.5% to about 12.5% polyhexamethylene biguanide, about 62% to about 78% of isopropanol and about 0.2% to about 0.8% of ortho-phthalaldehyde. In other aspects of this embodiment, a composition disclosed herein comprises about 7.5% to about 11.5% polyhexamethylene biguanide, about 65% to about 75% of isopropanol and about 0.3% to about 0.7% of ortho-phthalaldehyde. In yet other aspects of this embodiment, a composition disclosed herein comprises about 8.5% to about 10.5% polyhexamethylene biguanide, about 67% to about 73% of isopropanol and about 0.4% to about 0.6% of ortho-phthalaldehyde. In still other aspects of this embodiment, a composition disclosed herein comprises about 9.5% polyhexamethylene biguanide, about 70% of isopropanol and about 0.5% of ortho-phthalaldehyde.

In an embodiment, a composition disclosed herein comprises about 1% to about 10% of biguanide-containing compound, about 60% to about 80% of an alcohol and about 1% to about 10% of a quaternary ammonium surfactant. In aspects of this embodiment, a composition disclosed herein comprises about 2% to about 8% of biguanide-containing compound, about 62% to about 78% of an alcohol and about 2% to about 8% of a quaternary ammonium surfactant. In other aspects of this embodiment, a composition disclosed herein comprises about 3% to about 7% of biguanide-containing compound, about 65% to about 75% of an alcohol and about 3% to about 7% of a quaternary ammonium surfactant. In yet other aspects of this embodiment, a composition disclosed herein comprises about 4% to about 6% of biguanide-containing compound, about 67% to about 73% of an alcohol and about 4% to about 6% of a quaternary ammonium surfactant. In still other aspects of this embodiment, a composition disclosed herein comprises about 5% of biguanide-containing compound, about 70% of an alcohol and about 5% of a quaternary ammonium surfactant.

In an embodiment, a composition disclosed herein comprises about 1% to about 10% polyhexamethylene biguanide, about 60% to about 80% of isopropanol and about 1% to about 10% of benzalkonium chloride. In aspects of this embodiment, a composition disclosed herein comprises about 2% to about 8% polyhexamethylene biguanide, about 62% to about 78% of isopropanol and about 2% to about 8% of benzalkonium chloride. In other aspects of this embodiment, a composition disclosed herein comprises about 3% to about 7% polyhexamethylene biguanide, about 65% to about 75% of isopropanol and about 3% to about 7% of benzalkonium chloride. In yet other aspects of this embodiment, a composition disclosed herein comprises about 4% to about 6% polyhexamethylene biguanide, about 67% to about 73% of isopropanol and about 4% to about 6% of benzalkonium chloride. In still other aspects of this embodiment, a composition disclosed herein comprises about 5% polyhexamethylene biguanide, about 70% of isopropanol and about 5% of benzalkonium chloride or cetylpyridinium chloride.

In an embodiment, a composition disclosed herein comprises about 5% to about 15% of biguanide-containing compound, about 55% to about 75% of an alcohol and about 1% to about 10% of a quaternary ammonium surfactant. In aspects of this embodiment, a composition disclosed herein comprises about 7% to about 13% of biguanide-containing compound, about 57% to about 73% of an alcohol and about 2% to about 8% of a quaternary ammonium surfactant. In other aspects of this embodiment, a composition disclosed herein comprises about 8% to about 12% of biguanide-containing compound, about 60% to about 70% of an alcohol and about 3% to about 7% of a quaternary ammonium surfactant. In yet other aspects of this embodiment, a composition disclosed herein comprises about 9% to about 11% of biguanide-containing compound, about 62% to about 68% of an alcohol and about 4% to about 6% of a quaternary ammonium surfactant. In still other aspects of this embodiment, a composition disclosed herein comprises about 10% of biguanide-containing compound, about 65% of an alcohol and about 5% of a quaternary ammonium surfactant.

In an embodiment, a composition disclosed herein comprises about 5% to about 15% polyhexamethylene biguanide, about 55% to about 75% of isopropanol and about 1% to about 10% of benzalkonium chloride. In aspects of this embodiment, a composition disclosed herein comprises about 7% to about 13% polyhexamethylene biguanide, about 57% to about 73% of isopropanol and about 2% to about 8% of benzalkonium chloride. In other aspects of this embodiment, a composition disclosed herein comprises about 8% to about 12% polyhexamethylene biguanide, about 60% to about 70% of isopropanol and about 3% to about 7% of benzalkonium chloride. In yet other aspects of this embodiment, a composition disclosed herein comprises about 9% to about 11% polyhexamethylene biguanide, about 62% to about 68% of isopropanol and about 4% to about 6% of benzalkonium chloride. In still other aspects of this embodiment, a composition disclosed herein comprises about 10% polyhexamethylene biguanide, about 65% of isopropanol and about 5% of benzalkonium chloride or cetylpyridinium chloride.

In an embodiment, a composition disclosed herein comprises about 85 ppm to about 120 ppm hypochlorous acid or free available chlorine and about 1.0% to about 3.0% of biguanide-containing compound. In aspects of this embodiment, a composition disclosed herein comprises about 90 ppm to about 115 ppm hypochlorous acid or free available chlorine and about 1.25% to about 2.75% of biguanide-containing compound. In other aspects of this embodiment, a composition disclosed herein comprises about 95 ppm to about 110 ppm hypochlorous acid or free available chlorine and about 1.5% to about 2.5% of biguanide-containing compound. In yet other aspects of this embodiment, a composition disclosed herein comprises about 100 ppm to about 106 ppm hypochlorous acid or free available chlorine and about 1.75% to about 2.25% of biguanide-containing compound. In still other aspects of this embodiment, a composition disclosed herein comprises about 103 ppm hypochlorous acid or free available chlorine and about 2.0% of biguanide-containing compound.

In an embodiment, a composition disclosed herein comprises about 85 ppm to about 120 ppm hypochlorous acid or free available chlorine and about 1.0% to about 3.0% polyhexamethylene biguanide. In aspects of this embodiment, a composition disclosed herein comprises about 90 ppm to about 115 ppm hypochlorous acid or free available chlorine and about 1.25% to about 2.75% polyhexamethylene biguanide. In other aspects of this embodiment, a composition disclosed herein comprises about 95 ppm to about 110 ppm hypochlorous acid or free available chlorine and about 1.5% to about 2.5% polyhexamethylene biguanide. In yet other aspects of this embodiment, a composition disclosed herein comprises about 100 ppm to about 106 ppm hypochlorous acid or free available chlorine and about 1.75% to about 2.25% polyhexamethylene biguanide. In still other aspects of this embodiment, a composition disclosed herein comprises about 103 ppm hypochlorous acid or free available chlorine and about 2.0% polyhexamethylene biguanide.

In an embodiment, a composition disclosed herein comprises about 85 ppm to about 120 ppm hypochlorous acid or free available chlorine and about 0.5% to about 2.5% of biguanide-containing compound. In aspects of this embodiment, a composition disclosed herein comprises about 90 ppm to about 115 ppm hypochlorous acid or free available chlorine and about 0.75% to about 2.25% of biguanide-containing compound. In other aspects of this embodiment, a composition disclosed herein comprises about 95 ppm to about 110 ppm hypochlorous acid or free available chlorine and about 1.0% to about 2.0% of biguanide-containing compound. In yet other aspects of this embodiment, a composition disclosed herein comprises about 100 ppm to about 106 ppm hypochlorous acid or free available chlorine and about 1.25% to about 1.75% of biguanide-containing compound. In still other aspects of this embodiment, a composition disclosed herein comprises about 103 ppm hypochlorous acid or free available chlorine and about 1.5% of biguanide-containing compound.

In an embodiment, a composition disclosed herein comprises about 85 ppm to about 120 ppm hypochlorous acid or free available chlorine and about 0.5% to about 2.5% polyhexamethylene biguanide. In aspects of this embodiment, a composition disclosed herein comprises about 90 ppm to about 115 ppm hypochlorous acid or free available chlorine and about 0.75% to about 2.25% polyhexamethylene biguanide. In other aspects of this embodiment, a composition disclosed herein comprises about 95 ppm to about 110 ppm hypochlorous acid or free available chlorine and about 1.0% to about 2.0% polyhexamethylene biguanide. In yet other aspects of this embodiment, a composition disclosed herein comprises about 100 ppm to about 106 ppm hypochlorous acid or free available chlorine and about 1.25% to about 1.75% polyhexamethylene biguanide. In still other aspects of this embodiment, a composition disclosed herein comprises about 103 ppm hypochlorous acid or free available chlorine and about 1.5% polyhexamethylene biguanide.

In an embodiment, a composition disclosed herein comprises about 0.1% to about 7% of biguanide-containing compound and about 60% to about 80% of one or more alcohols. In aspects of this embodiment, a composition disclosed herein comprises about 0.5% to about 6% of biguanide-containing compound and about 62% to about 78% of one or more alcohols. In other aspects of this embodiment, a composition disclosed herein comprises about 1% to about 5% of biguanide-containing compound and about 65% to about 75% of one or more alcohols. In yet other aspects of this embodiment, a composition disclosed herein comprises about 2% to about 4% of biguanide-containing compound and about 67% to about 73% of one or more alcohols. In still other aspects of this embodiment, a composition disclosed herein comprises about 3% of biguanide-containing compound and about 70% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 0.1% to about 7% polyhexamethylene biguanide and about 60% to about 80% isopropanol. In aspects of this embodiment, a composition disclosed herein comprises about 0.5% to about 6% polyhexamethylene biguanide and about 62% to about 78% isopropanol. In other aspects of this embodiment, a composition disclosed herein comprises about 1% to about 5% polyhexamethylene biguanide and about 65% to about 75% isopropanol. In yet other aspects of this embodiment, a composition disclosed herein comprises about 2% to about 4% polyhexamethylene biguanide and about 67% to about 73% isopropanol. In still other aspects of this embodiment, a composition disclosed herein comprises about 3% polyhexamethylene biguanide and about 70% isopropanol. In other aspects of this embodiment, the isopropanol can be replaced with a 5:1 to 1:5 isopropanol: ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 0.1% to about 7% of biguanide-containing compound and about 50% to about 70% of one or more alcohols. In aspects of this embodiment, a composition disclosed herein comprises about 0.5% to about 6% of biguanide-containing compound and about 52% to about 68% of one or more alcohols. In other aspects of this embodiment, a composition disclosed herein comprises about 1% to about 5% of biguanide-containing compound and about 55% to about 65% of one or more alcohols. In yet other aspects of this embodiment, a composition disclosed herein comprises about 2% to about 4% of biguanide-containing compound and about 57% to about 63% of one or more alcohols. In still other aspects of this embodiment, a composition disclosed herein comprises about 3% of biguanide-containing compound and about 60% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 0.1% to about 7% polyhexamethylene biguanide and about 50% to about 70% isopropanol. In aspects of this embodiment, a composition disclosed herein comprises about 0.5% to about 6% polyhexamethylene biguanide and about 52% to about 68% isopropanol. In other aspects of this embodiment, a composition disclosed herein comprises about 1% to about 5% polyhexamethylene biguanide and about 55% to about 65% isopropanol. In yet other aspects of this embodiment, a composition disclosed herein comprises about 2% to about 4% polyhexamethylene biguanide and about 57% to about 63% isopropanol. In still other aspects of this embodiment, a composition disclosed herein comprises about 3% polyhexamethylene biguanide and about 60% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 0.1% to about 7% of biguanide-containing compound and about 40% to about 60% of one or more alcohols. In aspects of this embodiment, a composition disclosed herein comprises about 0.5% to about 6% of biguanide-containing compound and about 42% to about 58% of one or more alcohols. In other aspects of this embodiment, a composition disclosed herein comprises about 1% to about 5% of biguanide-containing compound and about 45% to about 55% of one or more alcohols. In yet other aspects of this embodiment, a composition disclosed herein comprises about 2% to about 4% of biguanide-containing compound and about 47% to about 53% of one or more alcohols. In still other aspects of this embodiment, a composition disclosed herein comprises about 3% of biguanide-containing compound and about 50% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 0.1% to about 7% polyhexamethylene biguanide and about 40% to about 60% isopropanol. In aspects of this embodiment, a composition disclosed herein comprises about 0.5% to about 6% polyhexamethylene biguanide and about 42% to about 58% isopropanol. In other aspects of this embodiment, a composition disclosed herein comprises about 1% to about 5% polyhexamethylene biguanide and about 45% to about 55% isopropanol. In yet other aspects of this embodiment, a composition disclosed herein comprises about 2% to about 4% polyhexamethylene biguanide and about 47% to about 53% isopropanol. In still other aspects of this embodiment, a composition disclosed herein comprises about 3% polyhexamethylene biguanide and about 50% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 15% of biguanide-containing compound and about 20% to about 85% of one or more alcohols. In aspects of this embodiment, a composition disclosed herein comprises about 3% to about 13% of biguanide-containing compound and about 25% to about 80% of one or more alcohols. In other aspects of this embodiment, a composition disclosed herein comprises about 4% to about 12% of biguanide-containing compound and about 30% to about 75% of one or more alcohols. In yet other aspects of this embodiment, a composition disclosed herein comprises about 5% to about 11% of biguanide-containing compound and about 35% to about 70% of one or more alcohols. In still other aspects of this embodiment, a composition disclosed herein comprises about 6% to about 10% of biguanide-containing compound and about 40% to about 65% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 15% polyhexamethylene biguanide and about 20% to about 85% isopropanol. In aspects of this embodiment, a composition disclosed herein comprises about 3% to about 13% polyhexamethylene biguanide and about 25% to about 80% isopropanol. In other aspects of this embodiment, a composition disclosed herein comprises about 4% to about 12% polyhexamethylene biguanide and about 30% to about 75% isopropanol. In yet other aspects of this embodiment, a composition disclosed herein comprises about 5% to about 11% polyhexamethylene biguanide and about 35% to about 70% isopropanol. In still other aspects of this embodiment, a composition disclosed herein comprises about 6% to about 10% polyhexamethylene biguanide and about 40% to about 60% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound and about 60% to about 80% of one or more alcohols. In aspects of this embodiment, a composition disclosed herein comprises about 3% to about 9% of biguanide-containing compound and about 62% to about 78% of one or more alcohols. In other aspects of this embodiment, a composition disclosed herein comprises about 4% to about 8% of biguanide-containing compound and about 65% to about 75% of one or more alcohols. In yet other aspects of this embodiment, a composition disclosed herein comprises about 5% to about 7% of biguanide-containing compound and about 67% to about 73% of one or more alcohols. In still other aspects of this embodiment, a composition disclosed herein comprises about 6% of biguanide-containing compound and about 70% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide and about 60% to about 80% isopropanol. In aspects of this embodiment, a composition disclosed herein comprises about 3% to about 9% polyhexamethylene biguanide and about 62% to about 78% isopropanol. In other aspects of this embodiment, a composition disclosed herein comprises about 4% to about 8% polyhexamethylene biguanide and about 65% to about 75% isopropanol. In yet other aspects of this embodiment, a composition disclosed herein comprises about 5% to about 7% polyhexamethylene biguanide and about 67% to about 73% isopropanol. In still other aspects of this embodiment, a composition disclosed herein comprises about 6% polyhexamethylene biguanide and about 70% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound and about 55% to about 75% of one or more alcohols. In aspects of this embodiment, a composition disclosed herein comprises about 3% to about 9% of biguanide-containing compound and about 57% to about 73% of one or more alcohols. In other aspects of this embodiment, a composition disclosed herein comprises about 4% to about 8% of biguanide-containing compound and about 60% to about 70% of one or more alcohols. In yet other aspects of this embodiment, a composition disclosed herein comprises about 5% to about 7% of biguanide-containing compound and about 62% to about 68% of one or more alcohols. In still other aspects of this embodiment, a composition disclosed herein comprises about 6% of biguanide-containing compound and about 65% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide and about 55% to about 75% isopropanol. In aspects of this embodiment, a composition disclosed herein comprises about 3% to about 9% polyhexamethylene biguanide and about 57% to about 73% isopropanol. In other aspects of this embodiment, a composition disclosed herein comprises about 4% to about 8% polyhexamethylene biguanide and about 60% to about 70% isopropanol. In yet other aspects of this embodiment, a composition disclosed herein comprises about 5% to about 7% polyhexamethylene biguanide and about 62% to about 68% isopropanol. In still other aspects of this embodiment, a composition disclosed herein comprises about 6% polyhexamethylene biguanide and about 65% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound and about 50% to about 70% of one or more alcohols. In aspects of this embodiment, a composition disclosed herein comprises about 3% to about 9% of biguanide-containing compound and about 52% to about 68% of one or more alcohols. In other aspects of this embodiment, a composition disclosed herein comprises about 4% to about 8% of biguanide-containing compound and about 55% to about 65% of one or more alcohols. In yet other aspects of this embodiment, a composition disclosed herein comprises about 5% to about 7% of biguanide-containing compound and about 57% to about 63% of one or more alcohols. In still other aspects of this embodiment, a composition disclosed herein comprises about 6% of biguanide-containing compound and about 60% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide and about 50% to about 70% isopropanol. In aspects of this embodiment, a composition disclosed herein comprises about 3% to about 9% polyhexamethylene biguanide and about 52% to about 68% isopropanol. In other aspects of this embodiment, a composition disclosed herein comprises about 4% to about 8% polyhexamethylene biguanide and about 55% to about 65% isopropanol. In yet other aspects of this embodiment, a composition disclosed herein comprises about 5% to about 7% polyhexamethylene biguanide and about 57% to about 63% isopropanol. In still other aspects of this embodiment, a composition disclosed herein comprises about 6% polyhexamethylene biguanide and about 60% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound and about 45% to about 65% of one or more alcohols. In aspects of this embodiment, a composition disclosed herein comprises about 3% to about 9% of biguanide-containing compound and about 47% to about 63% of one or more alcohols. In other aspects of this embodiment, a composition disclosed herein comprises about 4% to about 8% of biguanide-containing compound and about 50% to about 60% of one or more alcohols. In yet other aspects of this embodiment, a composition disclosed herein comprises about 5% to about 7% of biguanide-containing compound and about 52% to about 58% of one or more alcohols. In still other aspects of this embodiment, a composition disclosed herein comprises about 6% of biguanide-containing compound and about 55% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide and about 45% to about 65% isopropanol. In aspects of this embodiment, a composition disclosed herein comprises about 3% to about 9% polyhexamethylene biguanide and about 47% to about 63% isopropanol. In other aspects of this embodiment, a composition disclosed herein comprises about 4% to about 8% polyhexamethylene biguanide and about 50% to about 60% isopropanol. In yet other aspects of this embodiment, a composition disclosed herein comprises about 5% to about 7% polyhexamethylene biguanide and about 52% to about 58% isopropanol. In still other aspects of this embodiment, a composition disclosed herein comprises about 6% polyhexamethylene biguanide and about 55% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound and about 40% to about 60% of one or more alcohols. In aspects of this embodiment, a composition disclosed herein comprises about 3% to about 9% of biguanide-containing compound and about 42% to about 58% of one or more alcohols. In other aspects of this embodiment, a composition disclosed herein comprises about 4% to about 8% of biguanide-containing compound and about 45% to about 55% of one or more alcohols. In yet other aspects of this embodiment, a composition disclosed herein comprises about 5% to about 7% of biguanide-containing compound and about 47% to about 53% of one or more alcohols. In still other aspects of this embodiment, a composition disclosed herein comprises about 6% of biguanide-containing compound and about 50% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide and about 40% to about 60% isopropanol. In aspects of this embodiment, a composition disclosed herein comprises about 3% to about 9% polyhexamethylene biguanide and about 42% to about 58% isopropanol. In other aspects of this embodiment, a composition disclosed herein comprises about 4% to about 8% polyhexamethylene biguanide and about 45% to about 55% isopropanol. In yet other aspects of this embodiment, a composition disclosed herein comprises about 5% to about 7% polyhexamethylene biguanide and about 47% to about 53% isopropanol. In still other aspects of this embodiment, a composition disclosed herein comprises about 6% polyhexamethylene biguanide and about 50% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound and about 35% to about 55% of one or more alcohols. In aspects of this embodiment, a composition disclosed herein comprises about 3% to about 9% of biguanide-containing compound and about 37% to about 53% of one or more alcohols. In other aspects of this embodiment, a composition disclosed herein comprises about 4% to about 8% of biguanide-containing compound and about 40% to about 50% of one or more alcohols. In yet other aspects of this embodiment, a composition disclosed herein comprises about 5% to about 7% of biguanide-containing compound and about 42% to about 48% of one or more alcohols. In still other aspects of this embodiment, a composition disclosed herein comprises about 6% of biguanide-containing compound and about 45% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide and about 35% to about 55% isopropanol. In aspects of this embodiment, a composition disclosed herein comprises about 3% to about 9% polyhexamethylene biguanide and about 37% to about 53% isopropanol. In other aspects of this embodiment, a composition disclosed herein comprises about 4% to about 8% polyhexamethylene biguanide and about 40% to about 50% isopropanol. In yet other aspects of this embodiment, a composition disclosed herein comprises about 5% to about 7% polyhexamethylene biguanide and about 42% to about 48% isopropanol. In still other aspects of this embodiment, a composition disclosed herein comprises about 6% polyhexamethylene biguanide and about 45% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound and about 30% to about 50% of one or more alcohols. In aspects of this embodiment, a composition disclosed herein comprises about 3% to about 9% of biguanide-containing compound and about 32% to about 48% of one or more alcohols. In other aspects of this embodiment, a composition disclosed herein comprises about 4% to about 8% of biguanide-containing compound and about 35% to about 45% of one or more alcohols. In yet other aspects of this embodiment, a composition disclosed herein comprises about 5% to about 7% of biguanide-containing compound and about 37% to about 43% of one or more alcohols. In still other aspects of this embodiment, a composition disclosed herein comprises about 6% of biguanide-containing compound and about 40% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide and about 30% to about 50% isopropanol. In aspects of this embodiment, a composition disclosed herein comprises about 3% to about 9% polyhexamethylene biguanide and about 32% to about 48% isopropanol. In other aspects of this embodiment, a composition disclosed herein comprises about 4% to about 8% polyhexamethylene biguanide and about 35% to about 45% isopropanol. In yet other aspects of this embodiment, a composition disclosed herein comprises about 5% to about 7% polyhexamethylene biguanide and about 37% to about 43% isopropanol. In still other aspects of this embodiment, a composition disclosed herein comprises about 6% polyhexamethylene biguanide and about 40% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound and about 25% to about 45% of one or more alcohols. In aspects of this embodiment, a composition disclosed herein comprises about 3% to about 9% of biguanide-containing compound and about 27% to about 43% of one or more alcohols. In other aspects of this embodiment, a composition disclosed herein comprises about 4% to about 8% of biguanide-containing compound and about 30% to about 40% of one or more alcohols. In yet other aspects of this embodiment, a composition disclosed herein comprises about 5% to about 7% of biguanide-containing compound and about 32% to about 38% of one or more alcohols. In still other aspects of this embodiment, a composition disclosed herein comprises about 6% of biguanide-containing compound and about 35% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide and about 25% to about 45% isopropanol. In aspects of this embodiment, a composition disclosed herein comprises about 3% to about 9% polyhexamethylene biguanide and about 27% to about 43% isopropanol. In other aspects of this embodiment, a composition disclosed herein comprises about 4% to about 8% polyhexamethylene biguanide and about 30% to about 40% isopropanol. In yet other aspects of this embodiment, a composition disclosed herein comprises about 5% to about 7% polyhexamethylene biguanide and about 32% to about 38% isopropanol. In still other aspects of this embodiment, a composition disclosed herein comprises about 6% polyhexamethylene biguanide and about 35% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound and about 60% to about 80% of one or more alcohols. In aspects of this embodiment, a composition disclosed herein comprises about 5% to about 11% of biguanide-containing compound and about 62% to about 78% of one or more alcohols. In other aspects of this embodiment, a composition disclosed herein comprises about 6% to about 10% of biguanide-containing compound and about 65% to about 75% of one or more alcohols. In yet other aspects of this embodiment, a composition disclosed herein comprises about 7% to about 9% of biguanide-containing compound and about 67% to about 73% of one or more alcohols. In still other aspects of this embodiment, a composition disclosed herein comprises about 8% of biguanide-containing compound and about 70% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide and about 60% to about 80% isopropanol. In aspects of this embodiment, a composition disclosed herein comprises about 5% to about 11% polyhexamethylene biguanide and about 62% to about 78% isopropanol. In other aspects of this embodiment, a composition disclosed herein comprises about 6% to about 10% polyhexamethylene biguanide and about 65% to about 75% isopropanol. In yet other aspects of this embodiment, a composition disclosed herein comprises about 7% to about 9% polyhexamethylene biguanide and about 67% to about 73% isopropanol. In still other aspects of this embodiment, a composition disclosed herein comprises about 8% polyhexamethylene biguanide and about 70% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound and about 55% to about 75% of one or more alcohols. In aspects of this embodiment, a composition disclosed herein comprises about 5% to about 11% of biguanide-containing compound and about 57% to about 73% of one or more alcohols. In other aspects of this embodiment, a composition disclosed herein comprises about 6% to about 10% of biguanide-containing compound and about 60% to about 70% of one or more alcohols. In yet other aspects of this embodiment, a composition disclosed herein comprises about 7% to about 9% of biguanide-containing compound and about 62% to about 68% of one or more alcohols. In still other aspects of this embodiment, a composition disclosed herein comprises about 8% of biguanide-containing compound and about 65% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide and about 55% to about 75% isopropanol. In aspects of this embodiment, a composition disclosed herein comprises about 5% to about 11% polyhexamethylene biguanide and about 57% to about 73% isopropanol. In other aspects of this embodiment, a composition disclosed herein comprises about 6% to about 10% polyhexamethylene biguanide and about 60% to about 70% isopropanol. In yet other aspects of this embodiment, a composition disclosed herein comprises about 7% to about 9% polyhexamethylene biguanide and about 62% to about 68% isopropanol. In still other aspects of this embodiment, a composition disclosed herein comprises about 8% polyhexamethylene biguanide and about 65% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound and about 50% to about 70% of one or more alcohols. In aspects of this embodiment, a composition disclosed herein comprises about 5% to about 11% of biguanide-containing compound and about 52% to about 68% of one or more alcohols. In other aspects of this embodiment, a composition disclosed herein comprises about 6% to about 10% of biguanide-containing compound and about 55% to about 65% of one or more alcohols. In yet other aspects of this embodiment, a composition disclosed herein comprises about 7% to about 9% of biguanide-containing compound and about 57% to about 63% of one or more alcohols. In still other aspects of this embodiment, a composition disclosed herein comprises about 8% of biguanide-containing compound and about 60% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide and about 50% to about 70% isopropanol. In aspects of this embodiment, a composition disclosed herein comprises about 5% to about 11% polyhexamethylene biguanide and about 52% to about 68% isopropanol. In other aspects of this embodiment, a composition disclosed herein comprises about 6% to about 10% polyhexamethylene biguanide and about 55% to about 65% isopropanol. In yet other aspects of this embodiment, a composition disclosed herein comprises about 7% to about 9% polyhexamethylene biguanide and about 57% to about 63% isopropanol. In still other aspects of this embodiment, a composition disclosed herein comprises about 8% polyhexamethylene biguanide and about 60% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound and about 45% to about 65% of one or more alcohols. In aspects of this embodiment, a composition disclosed herein comprises about 5% to about 11% of biguanide-containing compound and about 47% to about 63% of one or more alcohols. In other aspects of this embodiment, a composition disclosed herein comprises about 6% to about 10% of biguanide-containing compound and about 50% to about 60% of one or more alcohols. In yet other aspects of this embodiment, a composition disclosed herein comprises about 7% to about 9% of biguanide-containing compound and about 52% to about 58% of one or more alcohols. In still other aspects of this embodiment, a composition disclosed herein comprises about 8% of biguanide-containing compound and about 55% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide and about 45% to about 65% isopropanol. In aspects of this embodiment, a composition disclosed herein comprises about 5% to about 11% polyhexamethylene biguanide and about 47% to about 63% isopropanol. In other aspects of this embodiment, a composition disclosed herein comprises about 6% to about 10% polyhexamethylene biguanide and about 50% to about 60% isopropanol. In yet other aspects of this embodiment, a composition disclosed herein comprises about 7% to about 9% polyhexamethylene biguanide and about 52% to about 58% isopropanol. In still other aspects of this embodiment, a composition disclosed herein comprises about 8% polyhexamethylene biguanide and about 55% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound and about 40% to about 60% of one or more alcohols. In aspects of this embodiment, a composition disclosed herein comprises about 5% to about 11% of biguanide-containing compound and about 42% to about 58% of one or more alcohols. In other aspects of this embodiment, a composition disclosed herein comprises about 6% to about 10% of biguanide-containing compound and about 45% to about 55% of one or more alcohols. In yet other aspects of this embodiment, a composition disclosed herein comprises about 7% to about 9% of biguanide-containing compound and about 47% to about 53% of one or more alcohols. In still other aspects of this embodiment, a composition disclosed herein comprises about 8% of biguanide-containing compound and about 50% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide and about 40% to about 60% isopropanol. In aspects of this embodiment, a composition disclosed herein comprises about 5% to about 11% polyhexamethylene biguanide and about 42% to about 58% isopropanol. In other aspects of this embodiment, a composition disclosed herein comprises about 6% to about 10% polyhexamethylene biguanide and about 45% to about 55% isopropanol. In yet other aspects of this embodiment, a composition disclosed herein comprises about 7% to about 9% polyhexamethylene biguanide and about 47% to about 53% isopropanol. In still other aspects of this embodiment, a composition disclosed herein comprises about 8% polyhexamethylene biguanide and about 50% isopropanol. In other aspects of this embodiment, the isopropanol can be replaced with a 5:1 to 1:5 isopropanol: ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound and about 35% to about 55% of one or more alcohols. In aspects of this embodiment, a composition disclosed herein comprises about 5% to about 11% of biguanide-containing compound and about 37% to about 53% of one or more alcohols. In other aspects of this embodiment, a composition disclosed herein comprises about 6% to about 10% of biguanide-containing compound and about 40% to about 50% of one or more alcohols. In yet other aspects of this embodiment, a composition disclosed herein comprises about 7% to about 9% of biguanide-containing compound and about 42% to about 48% of one or more alcohols. In still other aspects of this embodiment, a composition disclosed herein comprises about 8% of biguanide-containing compound and about 45% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide and about 35% to about 55% isopropanol. In aspects of this embodiment, a composition disclosed herein comprises about 5% to about 11% polyhexamethylene biguanide and about 37% to about 53% isopropanol. In other aspects of this embodiment, a composition disclosed herein comprises about 6% to about 10% polyhexamethylene biguanide and about 40% to about 50% isopropanol. In yet other aspects of this embodiment, a composition disclosed herein comprises about 7% to about 9% polyhexamethylene biguanide and about 42% to about 48% isopropanol. In still other aspects of this embodiment, a composition disclosed herein comprises about 8% polyhexamethylene biguanide and about 45% isopropanol. In other aspects of this embodiment, the isopropanol can be replaced with a 5:1 to 1:5 isopropanol: ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound and about 30% to about 50% of one or more alcohols. In aspects of this embodiment, a composition disclosed herein comprises about 5% to about 11% of biguanide-containing compound and about 32% to about 48% of one or more alcohols. In other aspects of this embodiment, a composition disclosed herein comprises about 6% to about 10% of biguanide-containing compound and about 35% to about 45% of one or more alcohols. In yet other aspects of this embodiment, a composition disclosed herein comprises about 7% to about 9% of biguanide-containing compound and about 37% to about 43% of one or more alcohols. In still other aspects of this embodiment, a composition disclosed herein comprises about 8% of biguanide-containing compound and about 40% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide and about 30% to about 50% isopropanol. In aspects of this embodiment, a composition disclosed herein comprises about 5% to about 11% polyhexamethylene biguanide and about 32% to about 48% isopropanol. In other aspects of this embodiment, a composition disclosed herein comprises about 6% to about 10% polyhexamethylene biguanide and about 35% to about 45% isopropanol. In yet other aspects of this embodiment, a composition disclosed herein comprises about 7% to about 9% polyhexamethylene biguanide and about 37% to about 43% isopropanol. In still other aspects of this embodiment, a composition disclosed herein comprises about 8% polyhexamethylene biguanide and about 40% isopropanol. In other aspects of this embodiment, the isopropanol can be replaced with a 5:1 to 1:5 isopropanol: ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound and about 25% to about 45% of one or more alcohols. In aspects of this embodiment, a composition disclosed herein comprises about 5% to about 11% of biguanide-containing compound and about 27% to about 43% of one or more alcohols. In other aspects of this embodiment, a composition disclosed herein comprises about 6% to about 10% of biguanide-containing compound and about 30% to about 40% of one or more alcohols. In yet other aspects of this embodiment, a composition disclosed herein comprises about 7% to about 9% of biguanide-containing compound and about 32% to about 38% of one or more alcohols. In still other aspects of this embodiment, a composition disclosed herein comprises about 8% of biguanide-containing compound and about 35% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide and about 25% to about 45% isopropanol. In aspects of this embodiment, a composition disclosed herein comprises about 5% to about 11% polyhexamethylene biguanide and about 27% to about 43% isopropanol. In other aspects of this embodiment, a composition disclosed herein comprises about 6% to about 10% polyhexamethylene biguanide and about 30% to about 40% isopropanol. In yet other aspects of this embodiment, a composition disclosed herein comprises about 7% to about 9% polyhexamethylene biguanide and about 32% to about 38% isopropanol. In still other aspects of this embodiment, a composition disclosed herein comprises about 8% polyhexamethylene biguanide and about 35% isopropanol. In other aspects of this embodiment, the isopropanol can be replaced with a 5:1 to 1:5 isopropanol: ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound and about 60% to about 80% of one or more alcohols. In aspects of this embodiment, a composition disclosed herein comprises about 7% to about 13% of biguanide-containing compound and about 62% to about 78% of one or more alcohols. In other aspects of this embodiment, a composition disclosed herein comprises about 8% to about 12% of biguanide-containing compound and about 65% to about 75% of one or more alcohols. In yet other aspects of this embodiment, a composition disclosed herein comprises about 9% to about 11% of biguanide-containing compound and about 67% to about 73% of one or more alcohols. In still other aspects of this embodiment, a composition disclosed herein comprises about 10% of biguanide-containing compound and about 70% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide and about 60% to about 80% isopropanol. In aspects of this embodiment, a composition disclosed herein comprises about 7% to about 13% polyhexamethylene biguanide and about 62% to about 78% isopropanol. In other aspects of this embodiment, a composition disclosed herein comprises about 8% to about 12% polyhexamethylene biguanide and about 65% to about 75% isopropanol. In yet other aspects of this embodiment, a composition disclosed herein comprises about 9% to about 11% polyhexamethylene biguanide and about 67% to about 73% isopropanol. In still other aspects of this embodiment, a composition disclosed herein comprises about 10% polyhexamethylene biguanide and about 70% isopropanol. In other aspects of this embodiment, the isopropanol can be replaced with a 5:1 to 1:5 isopropanol: ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound and about 55% to about 75% of one or more alcohols. In aspects of this embodiment, a composition disclosed herein comprises about 7% to about 13% of biguanide-containing compound and about 57% to about 73% of one or more alcohols. In other aspects of this embodiment, a composition disclosed herein comprises about 8% to about 12% of biguanide-containing compound and about 60% to about 70% of one or more alcohols. In yet other aspects of this embodiment, a composition disclosed herein comprises about 9% to about 11% of biguanide-containing compound and about 62% to about 68% of one or more alcohols. In still other aspects of this embodiment, a composition disclosed herein comprises about 10% of biguanide-containing compound and about 65% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide and about 55% to about 75% isopropanol. In aspects of this embodiment, a composition disclosed herein comprises about 7% to about 13% polyhexamethylene biguanide and about 57% to about 73% isopropanol. In other aspects of this embodiment, a composition disclosed herein comprises about 8% to about 12% polyhexamethylene biguanide and about 60% to about 70% isopropanol. In yet other aspects of this embodiment, a composition disclosed herein comprises about 9% to about 11% polyhexamethylene biguanide and about 62% to about 68% isopropanol. In still other aspects of this embodiment, a composition disclosed herein comprises about 10% polyhexamethylene biguanide and about 65% isopropanol. In other aspects of this embodiment, the isopropanol can be replaced with a 5:1 to 1:5 isopropanol: ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound and about 50% to about 70% of one or more alcohols. In aspects of this embodiment, a composition disclosed herein comprises about 7% to about 13% of biguanide-containing compound and about 52% to about 68% of one or more alcohols. In other aspects of this embodiment, a composition disclosed herein comprises about 8% to about 12% of biguanide-containing compound and about 55% to about 65% of one or more alcohols. In yet other aspects of this embodiment, a composition disclosed herein comprises about 9% to about 11% of biguanide-containing compound and about 57% to about 63% of one or more alcohols. In still other aspects of this embodiment, a composition disclosed herein comprises about 10% of biguanide-containing compound and about 60% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide and about 60% to about 70% isopropanol. In aspects of this embodiment, a composition disclosed herein comprises about 7% to about 13% polyhexamethylene biguanide and about 52% to about 68% isopropanol. In other aspects of this embodiment, a composition disclosed herein comprises about 8% to about 12% polyhexamethylene biguanide and about 55% to about 65% isopropanol. In yet other aspects of this embodiment, a composition disclosed herein comprises about 9% to about 11% polyhexamethylene biguanide and about 57% to about 63% isopropanol. In still other aspects of this embodiment, a composition disclosed herein comprises about 10% polyhexamethylene biguanide and about 60% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound and about 45% to about 65% of one or more alcohols. In aspects of this embodiment, a composition disclosed herein comprises about 7% to about 13% of biguanide-containing compound and about 47% to about 63% of one or more alcohols. In other aspects of this embodiment, a composition disclosed herein comprises about 8% to about 12% of biguanide-containing compound and about 50% to about 60% of one or more alcohols. In yet other aspects of this embodiment, a composition disclosed herein comprises about 9% to about 11% of biguanide-containing compound and about 52% to about 58% of one or more alcohols. In still other aspects of this embodiment, a composition disclosed herein comprises about 10% of biguanide-containing compound and about 55% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide and about 45% to about 65% isopropanol. In aspects of this embodiment, a composition disclosed herein comprises about 7% to about 13% polyhexamethylene biguanide and about 47% to about 63% isopropanol. In other aspects of this embodiment, a composition disclosed herein comprises about 8% to about 12% polyhexamethylene biguanide and about 50% to about 60% isopropanol. In yet other aspects of this embodiment, a composition disclosed herein comprises about 9% to about 11% polyhexamethylene biguanide and about 52% to about 58% isopropanol. In still other aspects of this embodiment, a composition disclosed herein comprises about 10% polyhexamethylene biguanide and about 55% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound and about 40% to about 60% of one or more alcohols. In aspects of this embodiment, a composition disclosed herein comprises about 7% to about 13% of biguanide-containing compound and about 42% to about 58% of one or more alcohols. In other aspects of this embodiment, a composition disclosed herein comprises about 8% to about 12% of biguanide-containing compound and about 45% to about 55% of one or more alcohols. In yet other aspects of this embodiment, a composition disclosed herein comprises about 9% to about 11% of biguanide-containing compound and about 47% to about 53% of one or more alcohols. In still other aspects of this embodiment, a composition disclosed herein comprises about 10% of biguanide-containing compound and about 50% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide and about 40% to about 60% isopropanol. In aspects of this embodiment, a composition disclosed herein comprises about 7% to about 13% polyhexamethylene biguanide and about 42% to about 58% isopropanol. In other aspects of this embodiment, a composition disclosed herein comprises about 8% to about 12% polyhexamethylene biguanide and about 45% to about 55% isopropanol. In yet other aspects of this embodiment, a composition disclosed herein comprises about 9% to about 11% polyhexamethylene biguanide and about 47% to about 53% isopropanol. In still other aspects of this embodiment, a composition disclosed herein comprises about 10% polyhexamethylene biguanide and about 50% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound and about 35% to about 55% of one or more alcohols. In aspects of this embodiment, a composition disclosed herein comprises about 7% to about 13% of biguanide-containing compound and about 37% to about 53% of one or more alcohols. In other aspects of this embodiment, a composition disclosed herein comprises about 8% to about 12% of biguanide-containing compound and about 40% to about 50% of one or more alcohols. In yet other aspects of this embodiment, a composition disclosed herein comprises about 9% to about 11% of biguanide-containing compound and about 42% to about 48% of one or more alcohols. In still other aspects of this embodiment, a composition disclosed herein comprises about 10% of biguanide-containing compound and about 45% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide and about 35% to about 55% isopropanol. In aspects of this embodiment, a composition disclosed herein comprises about 7% to about 13% polyhexamethylene biguanide and about 37% to about 53% isopropanol. In other aspects of this embodiment, a composition disclosed herein comprises about 8% to about 12% polyhexamethylene biguanide and about 40% to about 50% isopropanol. In yet other aspects of this embodiment, a composition disclosed herein comprises about 9% to about 11% polyhexamethylene biguanide and about 42% to about 48% isopropanol. In still other aspects of this embodiment, a composition disclosed herein comprises about 10% polyhexamethylene biguanide and about 45% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound and about 30% to about 50% of one or more alcohols. In aspects of this embodiment, a composition disclosed herein comprises about 7% to about 13% of biguanide-containing compound and about 32% to about 48% of one or more alcohols. In other aspects of this embodiment, a composition disclosed herein comprises about 8% to about 12% of biguanide-containing compound and about 35% to about 45% of one or more alcohols. In yet other aspects of this embodiment, a composition disclosed herein comprises about 9% to about 11% of biguanide-containing compound and about 37% to about 43% of one or more alcohols. In still other aspects of this embodiment, a composition disclosed herein comprises about 10% of biguanide-containing compound and about 40% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide and about 30% to about 50% isopropanol. In aspects of this embodiment, a composition disclosed herein comprises about 7% to about 13% polyhexamethylene biguanide and about 32% to about 48% isopropanol. In other aspects of this embodiment, a composition disclosed herein comprises about 8% to about 12% polyhexamethylene biguanide and about 35% to about 45% isopropanol. In yet other aspects of this embodiment, a composition disclosed herein comprises about 9% to about 11% polyhexamethylene biguanide and about 37% to about 43% isopropanol. In still other aspects of this embodiment, a composition disclosed herein comprises about 10% polyhexamethylene biguanide and about 40% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound and about 25% to about 45% of one or more alcohols. In aspects of this embodiment, a composition disclosed herein comprises about 7% to about 13% of biguanide-containing compound and about 27% to about 43% of one or more alcohols. In other aspects of this embodiment, a composition disclosed herein comprises about 8% to about 12% of biguanide-containing compound and about 30% to about 40% of one or more alcohols. In yet other aspects of this embodiment, a composition disclosed herein comprises about 9% to about 11% of biguanide-containing compound and about 32% to about 38% of one or more alcohols. In still other aspects of this embodiment, a composition disclosed herein comprises about 10% of biguanide-containing compound and about 35% of one or more alcohols. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide and about 25% to about 45% isopropanol. In aspects of this embodiment, a composition disclosed herein comprises about 7% to about 13% polyhexamethylene biguanide and about 27% to about 43% isopropanol. In other aspects of this embodiment, a composition disclosed herein comprises about 8% to about 12% polyhexamethylene biguanide and about 30% to about 40% isopropanol. In yet other aspects of this embodiment, a composition disclosed herein comprises about 9% to about 11% polyhexamethylene biguanide and about 32% to about 38% isopropanol. In still other aspects of this embodiment, a composition disclosed herein comprises about 10% polyhexamethylene biguanide and about 35% isopropanol. In other aspects of this embodiment, the isopropanol can be replaced with a 5:1 to 1:5 isopropanol:ethanol mixture. In yet other aspects of this embodiment, the compositions further comprise about 2% to about 7% of cetylpyridinium chloride. In still other aspects of this embodiment, the compositions are used to clean, disinfect and/or sterilize an endoscope, a heart-lung machine, or a hard surface as disclosed herein.

In an embodiment, a composition disclosed herein comprises about 6% to about 15% of biguanide-containing compound. In aspects of this embodiment, a composition disclosed herein comprises about 7% to about 13% of biguanide-containing compound. In other aspects of this embodiment, a composition disclosed herein comprises about 8% to about 12% of biguanide-containing compound. In yet other aspects of this embodiment, a composition disclosed herein comprises about 9% to about 11% of biguanide-containing compound. In still other aspects of this embodiment, a composition disclosed herein comprises about 10% of biguanide-containing compound. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 6% to about 15% polyhexamethylene biguanide. In aspects of this embodiment, a composition disclosed herein comprises about 7% to about 13% polyhexamethylene biguanide. In other aspects of this embodiment, a composition disclosed herein comprises about 8% to about 12% polyhexamethylene biguanide. In yet other aspects of this embodiment, a composition disclosed herein comprises about 9% to about 11% polyhexamethylene biguanide. In still other aspects of this embodiment, a composition disclosed herein comprises about 10% polyhexamethylene biguanide. In other aspects of this embodiment, the compositions are used to clean, disinfect and/or sterilize an endoscope, a heart-lung machine, or a hard surface as disclosed herein.

In an embodiment, a composition disclosed herein comprises about 3% to about 13% of biguanide-containing compound. In aspects of this embodiment, a composition disclosed herein comprises about 5% to about 11% of biguanide-containing compound. In other aspects of this embodiment, a composition disclosed herein comprises about 6% to about 10% of biguanide-containing compound. In yet other aspects of this embodiment, a composition disclosed herein comprises about 7% to about 9% of biguanide-containing compound. In still other aspects of this embodiment, a composition disclosed herein comprises about 8% of biguanide-containing compound. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 3% to about 13% polyhexamethylene biguanide. In aspects of this embodiment, a composition disclosed herein comprises about 5% to about 11% polyhexamethylene biguanide. In other aspects of this embodiment, a composition disclosed herein comprises about 6% to about 10% polyhexamethylene biguanide. In yet other aspects of this embodiment, a composition disclosed herein comprises about 7% to about 9% polyhexamethylene biguanide. In still other aspects of this embodiment, a composition disclosed herein comprises about 8% polyhexamethylene biguanide. In other aspects of this embodiment, the compositions are used to clean, disinfect and/or sterilize an endoscope, a heart-lung machine, or a hard surface as disclosed herein.

In an embodiment, a composition disclosed herein comprises about 1% to about 10% of biguanide-containing compound. In aspects of this embodiment, a composition disclosed herein comprises about 3% to about 9% of biguanide-containing compound. In other aspects of this embodiment, a composition disclosed herein comprises about 4% to about 8% of biguanide-containing compound. In yet other aspects of this embodiment, a composition disclosed herein comprises about 5% to about 7% of biguanide-containing compound. In still other aspects of this embodiment, a composition disclosed herein comprises about 6% of biguanide-containing compound. In other aspects of this embodiment, the compositions further comprise about 2% to about 7% of a quaternary ammonium surfactant. In yet other aspects of this embodiment, the compositions are used to clean, disinfect and/or sterilize a device or a hard surface as disclosed herein.

In an embodiment, a composition disclosed herein comprises about 1% to about 10% polyhexamethylene biguanide. In aspects of this embodiment, a composition disclosed herein comprises about 3% to about 9% polyhexamethylene biguanide. In other aspects of this embodiment, a composition disclosed herein comprises about 4% to about 8% polyhexamethylene biguanide. In yet other aspects of this embodiment, a composition disclosed herein comprises about 5% to about 7% polyhexamethylene biguanide. In still other aspects of this embodiment, a composition disclosed herein comprises about 6% polyhexamethylene biguanide. In other aspects of this embodiment, the compositions are used to clean, disinfect and/or sterilize an endoscope, a heart-lung machine, or a hard surface as disclosed herein.

Aspects of the present specification disclose a kit. In one embodiment, the kit can comprise a container including a composition disclosed herein. In another embodiment, a kit can comprise one or more containers, each container including an individual component or more than one individual component disclosed herein in combination. For example, a kit can comprise one container including hypochlorous acid or free available chlorine and a second container including one or more disinfectants. As another example, a kit can comprise one container including one or more alcohols and a second container including one or more disinfectants. As yet another example, a kit can comprise one container including isopropanol and a second container including polyhexamethylene biguanide. As still another example, a kit can comprise one container including a mixture of isopropanol and ethanol and a second container including polyhexamethylene biguanide. As a further example, a kit can comprise one container including isopropanol, a second container including ethanol and a third container including polyhexamethylene biguanide. As another example, a kit can comprise one container including isopropanol, a second container including polyhexamethylene biguanide and a third container including one or more cationic surfactants. The remainder of the components of a composition disclosed herein may be included in either the first or second container, or may be separately including in at least a third container. For example, a third container including a rinse solution disclosed herein can be included in the kit. Packaging of individual components into separate container can assist in prolonging the stability of the individual components, and thus shelf life of the product.

In another example, a kit can comprise one container including hypochlorous acid and/or free available chlorine, a second container including one or more disinfectants, and a third container including a rinse solution. As another example, a kit can comprise one container including one or more alcohols, a second container including one or more disinfectants, and a third container including a rinse solution. As yet another example, a kit can comprise one container including isopropanol, a second container including polyhexamethylene biguanide, and a third container including a rinse solution. As still another example, a kit can comprise one container including a mixture of isopropanol and ethanol, a second container including polyhexamethylene biguanide, and a third container including a rinse solution. As a further example, a kit can comprise one container including isopropanol, a second container including ethanol, a third container including polyhexamethylene biguanide, and a fourth container including a rinse solution. As another example, a kit can comprise one container including isopropanol, a second container including polyhexamethylene biguanide, a third container including one or more cationic surfactants, and a fourth container including a rinse solution.

In another embodiment, a kit can comprise one container including a composition disclosed herein and a second container including a rinse solution disclosed herein. For example, a kit can comprise one container including hypochlorous acid and/or free available chlorine and one or more disinfectants and a second container including a rinse solution. As another example, a kit can comprise one container including one or more alcohols and one or more disinfectants and a second container including a rinse solution. As yet another example, a kit can comprise one container including isopropanol and polyhexamethylene biguanide and a second container including a rinse solution. As still another example, a kit can comprise one container including a mixture of isopropanol and ethanol and polyhexamethylene biguanide and a second container including a rinse solution. As a further example, a kit can comprise one container including isopropanol, polyhexamethylene biguanide and one or more cationic surfactant and a second container including a rinse solution. The remainder of the components of a composition disclosed herein may be included in either the first container or may be separately including in at least a third container. Packaging of individual components into separate container can assist in prolonging the stability of the individual components, and thus shelf life of the product.

A kit disclosed herein can comprise a delivery or application system. The delivery or application system of the kit are useful for applying a composition disclosed herein, and/or individual components disclosed herein to a site of interest, such as, e.g., a surface of a device disclosed herein. A delivery or application system disclosed herein, includes, without limitation, one or more of an applicator brush, porous foam swab or pad, hollow tube, dipstick, or a combination thereof. In an embodiment, a kit comprises a single delivery or application system. In another embodiment, a kit comprises a plurality delivery or application systems. For example, in a 30-day supply kit, there can be 30 delivery or application systems, such that there is one delivery or application system per day for 30 days. Alternately, there can be 2, 10, 20, 30, 40, 50, 60, 90, 120, etc. delivery or application systems per kit. Within the kit, the delivery or application system may be packaged individually, or in sets of 2 or more. The delivery or application system can be packaged such that it remains sterile until use. In certain embodiments, a delivery or application system disclosed herein can be packaged in plastic sheaths. Further, to prevent contamination, delivery or application system disclosed herein is preferably single-use, disposable delivery or application system.

The kit can also comprise a set of instructions. The instructions may include information useful to the end user such as how to use a delivery or application system to apply a composition and/or individual components disclosed herein, and/or how often to apply a composition and/or individual components disclosed herein. In addition, such instructions may include information regarding how to mix the individual components disclosed herein to form a composition disclosed herein. Such instructions can indicate that mixing should be done at a certain time before application, such as, e.g., just prior to use. Instructions disclosed herein may also include information regarding how to apply the individual components disclosed herein directly to a site of interest, such as, e.g., a surface of a device disclosed herein, and in what order the individual components should be applied to such sites of interest.

The contents of the kit, including the container including a composition or component disclosed herein, the delivery or application system, and instructions, are enclosed in an outer casing. The outer casing can be a box, a sealed bag, a foil pouch, etc. In certain embodiments, the delivery system, container and instructions are enclosed in a box. In other embodiments of the kit, the container and instructions are contained in a first box, the delivery system is contained in a second box, and the first and second box are contained together in a third box.

Aspects of the present specification disclose a method to clean, disinfect and/or sterilize a device, including a medical device. In an aspect of this embodiment, a method disclosed herein comprises applying a composition disclosed herein to a device for a specified amount of time, wherein application results in the cleaning, disinfecting and/or sterilization of the device. In another aspect of this embodiment, a method disclosed herein further comprises rinsing the cleaned, disinfected and/or sterilized device with a rinse solution disclosed herein. Other aspects of the present specification disclose a composition disclosed herein for use to clean, disinfect and/or sterilize a device, including a medical device. Yet other aspects of the present specification disclose a use of a disclosed composition to clean, disinfect and/or sterilize a device, including a medical device.

Aspects of the present specification disclose a method to clean, disinfect and/or sterilize an endoscope. In an aspect of this embodiment, a method disclosed herein comprises applying a composition disclosed herein to an endoscope for a specified amount of time, wherein application results in the cleaning, disinfecting and/or sterilization of the endoscope. In another aspect of this embodiment, a method disclosed herein further comprises rinsing the cleaned, disinfected and/or sterilized endoscope with a rinse solution disclosed herein. Other aspects of the present specification disclose a composition disclosed herein for use to clean, disinfect and/or sterilize an endoscope. Yet other aspects of the present specification disclose a use of a disclosed composition to clean, disinfect and/or sterilize an endoscope.

A device, including a medical device is cleaned by removal of visible soil, such as, e.g., organic and inorganic material, from objects and surfaces and normally is accomplished manually or mechanically. Thorough cleaning is essential before disinfection and sterilization because inorganic and organic materials that remain on the surfaces of a medical device interferes with the effectiveness of these processes.

A device, including a medical device is disinfected by eliminating many or all pathogenic microorganisms, except bacterial spores. Disinfection is less lethal than sterilization because it destroys most recognized pathogenic microorganisms but not necessarily all microbial forms (e.g., bacterial spores). A medical device is sterilized by destroying or eliminating all forms of microorganisms. Decontamination of a medical device removes pathogenic microorganisms from a medical device so that it is safe to handle, use, or discard.

A medical device is an instrument, apparatus, material, or other article, whether used alone or in combination, including software necessary for its application, intended by the manufacturer to be used for human beings for diagnosis, prevention, monitoring treatment, or alleviation of disease; diagnosis, monitoring, treatment, or alleviation of or compensation for an injury or handicap; investigation, replacement, or modification of the anatomy or of a physiologic process; or control of conception, and that does not achieve its primary intended action in or on the human body by pharmacologic, immunologic, or metabolic means but might be assisted in its function by such means. A medical device includes, without limitation, a surgical instrument, a respiratory therapy instrument, an anesthesia instrument, a catheter, an implant, a probe, an endoscope, an arthroscope, a laparoscope, a blade, a cystoscope, a spirometer, a CPAP mask and tubing, dialysis instrument and accessories, a heart-lung machine and accessories, a heart-lung bypass machine and accessories, and a diaphragm fitting ring. Non-limiting examples of a probe includes an ultrasound probe and an esophageal manometry probe. Non-limiting examples of a catheter includes a cardiac catheter, an urinary catheter, an anorectal manometry catheter. Non-limiting examples of an endoscope includes a gastrointestinal endoscope, a bronchoscope, and a nasopharyngoscope. Non-limiting examples of a blade includes a laryngoscope blade.

Aspects of the present specification disclose a method to clean, disinfect and/or sterilize a hard surface area. In an aspect of this embodiment, a method disclosed herein comprises applying a composition disclosed herein to a hard surface area for a specified amount of time, wherein application results in the cleaning, disinfecting and/or sterilization of the hard surface area. In another aspect of this embodiment, a method disclosed herein further comprises rinsing the cleaned, disinfected and/or sterilized surface with a rinse solution disclosed herein. Other aspects of the present specification disclose a composition disclosed herein for use to clean, disinfect and/or sterilize a hard surface area. Yet other aspects of the present specification disclose a use of a disclosed composition to clean, disinfect and/or sterilize a hard surface area. A hard surface area can be a porous surface area or a non-porous surface area.

In another aspect of this embodiment, a method disclosed herein comprises applying one or more individual components disclosed herein to a hard surface area for a specified amount of time, wherein application results in the cleaning, disinfecting and/or sterilization of the hard surface area. In an aspect of this embodiment, the one or more individual components include a first component including hypochlorous acid or free available chlorine and a second component including one or more disinfectants. In another aspect, application of the one or more individual components occur in a specific order, such as. e.g., first applying a first component including hypochlorous acid or free available chlorine and then applying a second component including one or more disinfectants. A hard surface area can be a porous surface area or a non-porous surface area.

A hard surface area can include any items present in a residence or a commercial, industrial and/or agricultural facility, such as, e.g., a hospital, a laboratory, a restaurant, an educational center, a food-processing facility, a dairy-processing facility, an airport, an oil field system, a sport facility, a shipping dock, a freight transport center, or any other commercial or industrial setting. A surface area can include any type of transportation carrier, such as, e.g., a water vessel like a boat, barge or ship, an aircraft like an airplane or helicopter, a ground vehicle like a motorcycle, car, truck or train, A surface area may be made of any material including brass, copper, aluminum, stainless steel, carbon steel, rubber, plastic, glass, wood, painted surface, or any combination thereof. A surface area includes, without limitation, a table top, counter top, floor, wall, ceiling, window, bed, gurney, door, door handle, shower, bath, sink, faucet, toilet, toilet seat, drain, equipment, machinery, personal protective gear, personal biohazard gear, and the like. A surface area may comprise a medical, dental, pharmaceutical, veterinary or mortuary device. A surface area may comprise human skin.

A composition or component disclosed herein can be applied to a hard surface area according to a method disclosed herein as often as needed and/or desired. A composition disclosed herein can be applied to a hard surface area daily, every other day, every third of day, once a week, multiple times per week, once a month, multiple times per month, once a year or multiple times per year, as desired. A composition disclosed herein can be applied to a hard surface area multiple times per day, e.g., twice a day, three times a day, four time a day, five times a day, six times a day or as often as desired.

Aspects of the present specification disclose a method to clean, disinfect and/or sterilize a microbial infection in an individual. In an aspect of this embodiment, a method disclosed herein comprises applying a composition disclosed herein to an individual for a specified amount of time, wherein application results in the cleaning, disinfecting and/or sterilization of a microbial infection in the individual. Other aspects of the present specification disclose a composition disclosed herein for use to clean, disinfect and/or sterilize a microbial infection in an individual. Yet other aspects of the present specification disclose a use of a disclosed composition to clean, disinfect and/or sterilize a microbial infection in an individual. Still other aspects of the present specification disclose a composition disclosed herein for the manufacture of a medicament to clean, disinfect and/or sterilize a microbial infection in an individual.

A method and/or use disclosed herein cleans, disinfects and/or sterilizes a microbial infection. A microbial infection includes a viral infection, a bacterial infection and a fungal infection.

A method and/or use disclosed herein applies a composition disclosed herein to an individual. An individual refers to any animal including, without limitation, a fish, an amphibian, a bird and a mammal. A mammal includes a human, a horse, a cow, a sheep, a dog and a cat. As such, a method disclosed herein is for human use as well as veterinarian use.

In applications to an individual, a composition disclosed herein can be applied to a skin surface or can be internally administered. In one embodiment, a composition disclosed herein is applied topically to a skin region of an individual in order to clean, disinfect and/or sterilize the skin region. A skin region, includes, without limitation, the face, forehead, lips, scalp, neck, shoulder, arms, hands, thighs, legs, knees, feet, chest, breast, back, groin, buttocks, and the like.

In one embodiment, a composition disclosed herein is internally administered to an individual. Such routes of administration include enteral routes of administration and parenteral routes of administration.

A composition disclosed herein can be applied according to a method disclosed herein to a skin region. Application of a composition disclosed herein can be by rubbing, pouring, sprinkling, or spraying on, or otherwise applied to the human body. A composition disclosed herein can be applied by introducing the composition into or onto a solid support such as, e.g., a wipe, a towelette, a towel, a mitt, a glove, or a mask and then applying the composition to a skin region. A composition disclosed herein can be applied by using a delivery device, such as, e.g., an aerosol dispenser, a pump spray, a trigger spray, a squeeze bottle, a topical patch, a transdermal patch, or a dermal implant to apply the composition to a skin region.

A composition disclosed herein can be applied to an individual according to a method disclosed herein as often as needed and/or desired. A composition disclosed herein can be applied to an individual daily, every other day, every third of day, once a week, multiple times per week, once a month, multiple times per month, once a year or multiple times per year, as desired. A composition disclosed herein can be applied to an individual multiple times per day, e.g., twice a day, three times a day, four time a day, five times a day, six times a day or as often as desired.

A disclosed method and/or use applies a composition disclosed herein for specified amount of time. In one embodiment, a specified amount of time is a time sufficient to clean a medical device, a surface, or an individual. In another embodiment, a specified amount of time is a time sufficient to disinfect a medical device, a surface, or an individual. In yet another embodiment, a specified amount of time is a time sufficient to sterilize a medical device, a surface, or an individual.

In aspects of this embodiment, a composition disclosed herein is applied to a device, like a medical device, a surface, or an individual for, e.g., about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 70 minutes, about 80 minutes, about 90 minutes, about 100 minutes, about 110 minutes, or about 120 minutes. In other aspects of this embodiment, a composition disclosed herein is applied to a device, like a medical device, a surface, or an individual for, e.g., at least 1 minute, at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 60 minutes, at least 70 minutes, at least 80 minutes, at least 90 minutes, at least 100 minutes, at least 110 minutes, or at least 120 minutes. In yet other aspects of this embodiment, a composition disclosed herein is applied to device, like a medical device, a surface, or an individual for, e.g., at most 1 minute, at most 5 minutes, at most 10 minutes, at most 15 minutes, at most 20 minutes, at most 25 minutes, at most 30 minutes, at most 35 minutes, at most 40 minutes, at most 45 minutes, at most 50 minutes, at most 55 minutes, at most 60 minutes, at most 70 minutes, at most 80 minutes, at most 90 minutes, at most 100 minutes, at most 110 minutes, or at most 120 minutes.

In still other aspects of this embodiment, a composition disclosed herein is applied to a device, like a medical device, a surface, or an individual for, e.g., about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 1 minute to about 35 minutes, about 1 minute to about 40 minutes, about 1 minute to about 45 minutes, about 1 minute to about 50 minutes, about 1 minute to about 55 minutes, about 1 minute to about 60 minutes, about 5 minutes to about 10 minutes, about 5 minutes to about 15 minutes, about 5 minutes to about 20 minutes, about 5 minutes to about 25 minutes, about 5 minutes to about 30 minutes, about 5 minutes to about 35 minutes, about 5 minutes to about 40 minutes, about 5 minutes to about 45 minutes, about 5 minutes to about 50 minutes, about 5 minutes to about 55 minutes, about 5 minutes to about 60 minutes, about 5 minutes to about 70 minutes, about 5 minutes to about 80 minutes, about 5 minutes to about 90 minutes, about 5 minutes to about 100 minutes, about 5 minutes to about 110 minutes, about 5 minutes to about 120 minutes, about 10 minutes to about 15 minutes, about 10 minutes to about 20 minutes, about 10 minutes to about 25 minutes, about 10 minutes to about 30 minutes, about 10 minutes to about 35 minutes, about 10 minutes to about 40 minutes, about 10 minutes to about 45 minutes, about 10 minutes to about 50 minutes, about 10 minutes to about 55 minutes, about 10 minutes to about 60 minutes, about 10 minutes to about 70 minutes, about 10 minutes to about 80 minutes, about 10 minutes to about 90 minutes, about 10 minutes to about 100 minutes, about 10 minutes to about 110 minutes, about 10 minutes to about 120 minutes, about 15 minutes to about 20 minutes, about 15 minutes to about 25 minutes, about 15 minutes to about 30 minutes, about 15 minutes to about 35 minutes, about 15 minutes to about 40 minutes, about 15 minutes to about 45 minutes, about 15 minutes to about 50 minutes, about 15 minutes to about 55 minutes, about 15 minutes to about 60 minutes, about 15 minutes to about 70 minutes, about 15 minutes to about 80 minutes, about 15 minutes to about 90 minutes, about 15 minutes to about 100 minutes, about 15 minutes to about 110 minutes, about 15 minutes to about 120 minutes, about 20 minutes to about 25 minutes, about 20 minutes to about 30 minutes, about 20 minutes to about 35 minutes, about 20 minutes to about 40 minutes, about 20 minutes to about 45 minutes, about 20 minutes to about 50 minutes, about 20 minutes to about 55 minutes, about 20 minutes to about 60 minutes, about 20 minutes to about 70 minutes, about 20 minutes to about 80 minutes, about 20 minutes to about 90 minutes, about 20 minutes to about 100 minutes, about 20 minutes to about 110 minutes, about 20 minutes to about 120 minutes, about 25 minutes to about 30 minutes, about 25 minutes to about 35 minutes, about 25 minutes to about 40 minutes, about 25 minutes to about 45 minutes, about 25 minutes to about 50 minutes, about 25 minutes to about 55 minutes, about 25 minutes to about 60 minutes, about 25 minutes to about 70 minutes, about 25 minutes to about 80 minutes, about 25 minutes to about 90 minutes, about 25 minutes to about 100 minutes, about 25 minutes to about 110 minutes, about 25 minutes to about 120 minutes, about 30 minutes to about 35 minutes, about 30 minutes to about 40 minutes, about 30 minutes to about 45 minutes, about 30 minutes to about 50 minutes, about 30 minutes to about 55 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 35 minutes to about 40 minutes, about 35 minutes to about 45 minutes, about 35 minutes to about 50 minutes, about 35 minutes to about 55 minutes, about 35 minutes to about 60 minutes, about 35 minutes to about 70 minutes, about 35 minutes to about 80 minutes, about 35 minutes to about 90 minutes, about 35 minutes to about 100 minutes, about 35 minutes to about 110 minutes, about 35 minutes to about 120 minutes, about 40 minutes to about 45 minutes, about 40 minutes to about 50 minutes, about 40 minutes to about 55 minutes, about 40 minutes to about 60 minutes, about 40 minutes to about 70 minutes, about 40 minutes to about 80 minutes, about 40 minutes to about 90 minutes, about 40 minutes to about 100 minutes, about 40 minutes to about 110 minutes, about 40 minutes to about 120 minutes, about 45 minutes to about 50 minutes, about 45 minutes to about 55 minutes, about 45 minutes to about 60 minutes, about 45 minutes to about 70 minutes, about 45 minutes to about 80 minutes, about 45 minutes to about 90 minutes, about 45 minutes to about 100 minutes, about 45 minutes to about 110 minutes, about 45 minutes to about 120 minutes, about 50 minutes to about 55 minutes, about 50 minutes to about 60 minutes, about 50 minutes to about 70 minutes, about 50 minutes to about 80 minutes, about 50 minutes to about 90 minutes, about 50 minutes to about 100 minutes, about 50 minutes to about 110 minutes, about 50 minutes to about 120 minutes, about 55 minutes to about 60 minutes, about 55 minutes to about 70 minutes, about 55 minutes to about 80 minutes, about 55 minutes to about 90 minutes, about 55 minutes to about 100 minutes, about 55 minutes to about 110 minutes, about 55 minutes to about 120 minutes, about 60 minutes to about 70 minutes, about 60 minutes to about 80 minutes, about 60 minutes to about 90 minutes, about 60 minutes to about 100 minutes, about 60 minutes to about 110 minutes, about 60 minutes to about 120 minutes, about 70 minutes to about 80 minutes, about 70 minutes to about 90 minutes, about 70 minutes to about 100 minutes, about 70 minutes to about 110 minutes, about 70 minutes to about 120 minutes, about 80 minutes to about 90 minutes, about 80 minutes to about 100 minutes, about 80 minutes to about 110 minutes, about 80 minutes to about 120 minutes, about 90 minutes to about 100 minutes, about 90 minutes to about 110 minutes, about 90 minutes to about 120 minutes, about 100 minutes to about 110 minutes, about 100 minutes to about 120 minutes, or about 110 minutes to about 120 minutes.

A disclosed composition, method and/or use are less harsh on a medical device resulting in a longer lifetime use of a medical device. In aspects of this embodiment, a medical device can be cleaned, disinfected and/or sterilized, e.g., about 50 times, about 60 times, about 70 times, about 80 times, about 90 times, about 100 times, about 110 times, about 120 times, about 130 times, about 140 times, about 150 times, about 160 times, about 170 times, about 180 times, about 190 times, about 200 times, about 210 times, about 220 times, about 230 times, about 240 times, about 250 times, about 260 times, about 270 times, about 280 times, about 290 times, or about 300 times. In other aspects of this embodiment, a medical device can be cleaned, disinfected and/or sterilized, e.g., at least 50 times, at least 60 times, at least 70 times, at least 80 times, at least 90 times, at least 100 times, at least 110 times, at least 120 times, at least 130 times, at least 140 times, at least 150 times, at least 160 times, at least 170 times, at least 180 times, at least 190 times, at least 200 times, at least 210 times, at least 220 times, at least 230 times, at least 240 times, at least 250 times, at least 260 times, at least 270 times, at least 280 times, at least 290 times, or at least 300 times. In yet other aspects of this embodiment, a medical device can be cleaned, disinfected and/or sterilized, e.g., at most 50 times, at most 60 times, at most 70 times, at most 80 times, at most 90 times, at most 100 times, at most 110 times, at most 120 times, at most 130 times, at most 140 times, at most 150 times, at most 160 times, at most 170 times, at most 180 times, at most 190 times, at most 200 times, at most 210 times, at most 220 times, at most 230 times, at most 240 times, at most 250 times, at most 260 times, at most 270 times, at most 280 times, at most 290 times, or at most 300 times.

In still other aspects of this embodiment, a medical device can be cleaned, disinfected and/or sterilized, e.g., about 50 times to about 60 times, about 50 times to about 70 times, about 50 times to about 80 times, about 50 times to about 90 times, about 50 times to about 100 times, about 50 times to about 110 times, about 50 times to about 120 times, about 50 times to about 130 times, about 50 times to about 140 times, about 50 times to about 150 times, about 50 times to about 175 times, about 50 times to about 200 times, about 50 times to about 225 times, about 50 times to about 250 times, about 50 times to about 275 times, about 50 times to about 300 times, about 75 times to about 90 times, about 75 times to about 100 times, about 75 times to about 110 times, about 75 times to about 120 times, about 75 times to about 130 times, about 75 times to about 140 times, about 75 times to about 150 times, about 75 times to about 175 times, about 75 times to about 200 times, about 75 times to about 225 times, about 75 times to about 250 times, about 75 times to about 275 times, about 75 times to about 300 times, about 100 times to about 110 times, about 100 times to about 120 times, about 100 times to about 130 times, about 100 times to about 140 times, about 100 times to about 150 times, about 100 times to about 175 times, about 100 times to about 200 times, about 100 times to about 225 times, about 100 times to about 250 times, about 100 times to about 275 times, about 100 times to about 300 times, about 125 times to about 150 times, about 125 times to about 175 times, about 125 times to about 200 times, about 125 times to about 225 times, about 125 times to about 250 times, about 125 times to about 275 times, about 125 times to about 300 times, about 150 times to about 175 times, about 150 times to about 200 times, about 150 times to about 225 times, about 150 times to about 250 times, about 150 times to about 275 times, about 150 times to about 300 times, about 175 times to about 200 times, about 175 times to about 225 times, about 175 times to about 250 times, about 175 times to about 275 times, about 175 times to about 300 times, about 200 times to about 225 times, about 200 times to about 250 times, about 200 times to about 275 times, about 200 times to about 300 times, about 225 times to about 250 times, about 225 times to about 275 times, about 225 times to about 300 times, about 250 times to about 275 times, about 250 times to about 300 times, or about 275 times to about 300 times.

A method disclosed herein may further comprises a rinsing step using a rinse solution. Typically, the rinse solution is used to rinse a cleaned, disinfected and/or sterilized medical device or surface. The rinse solution is preferably a sterile solution. In one embodiment, a rinse solution disclosed herein comprises water. In another embodiment, a rinse solution disclosed herein comprises hypochlorous acid or free available chlorine and water. In another embodiment, a rinse solution disclosed herein does not comprises hypochlorous acid and/or free available chlorine. When present in a kit disclosed herein, the rinse solution is present in a separate container.

The amount of hypochlorous acid or free available chlorine present in a rinse solution disclosed herein is any amount that provides an antimicrobial effect, with the proviso that the total amount of hypochlorous acid or free available chlorine present is an amount below the threshold level that results in oxidation of a medical device of surface as disclosed herein. In aspects of this embodiment, the amount of hypochlorous acid or free available chlorine present in a rinse solution may be, e.g., about 5 ppm, about 10 ppm, about 20 ppm, about 30 ppm, about 40 ppm, about 50 ppm, about 60 ppm, about 70 ppm, about 80 ppm, about 90 ppm, about 100 ppm, about 110 ppm, or about 120 ppm. In other aspects of this embodiment, the amount of hypochlorous acid or free available chlorine present in a rinse solution may be, e.g., at most 5 ppm, at most 10 ppm, at most 20 ppm, at most 30 ppm, at most 40 ppm, at most 50 ppm, at most 60 ppm, at most 70 ppm, at most 80 ppm, at most 90 ppm, at most 100 ppm, at most 110 ppm, or at most 120 ppm. In yet other aspects of this embodiment, the amount of hypochlorous acid or free available chlorine present in a rinse solution may be, e.g., about 5 ppm to about 10 ppm, about 5 ppm to about 20 ppm, about 5 ppm to about 30 ppm, about 5 ppm to about 40 ppm, about 5 ppm to about 50 ppm, about 5 ppm to about 60 ppm, about 5 ppm to about 70 ppm, about 5 ppm to about 80 ppm, about 5 ppm to about 90 ppm, about 5 ppm to about 100 ppm, about 5 ppm to about 110 ppm, about 5 ppm to about 120 ppm, about 10 ppm to about 20 ppm, about 10 ppm to about 30 ppm, about 10 ppm to about 40 ppm, about 10 ppm to about 50 ppm, about 10 ppm to about 60 ppm, about 10 ppm to about 70 ppm, about 10 ppm to about 80 ppm, about 10 ppm to about 90 ppm, about 10 ppm to about 100 ppm, about 10 ppm to about 110 ppm, about 10 ppm to about 120 ppm, about 20 ppm to about 30 ppm, about 20 ppm to about 40 ppm, about 20 ppm to about 50 ppm, about 20 ppm to about 60 ppm, about 20 ppm to about 70 ppm, about 20 ppm to about 80 ppm, about 20 ppm to about 90 ppm, about 20 ppm to about 100 ppm, about 20 ppm to about 110 ppm, about 20 ppm to about 120 ppm, about 30 ppm to about 40 ppm, about 30 ppm to about 50 ppm, about 30 ppm to about 60 ppm, about 30 ppm to about 70 ppm, about 30 ppm to about 80 ppm, about 30 ppm to about 90 ppm, about 30 ppm to about 100 ppm, about 30 ppm to about 110 ppm, about 30 ppm to about 120 ppm, about 40 ppm to about 50 ppm, about 40 ppm to about 60 ppm, about 40 ppm to about 70 ppm, about 40 ppm to about 80 ppm, about 40 ppm to about 90 ppm, about 40 ppm to about 100 ppm, about 40 ppm to about 110 ppm, about 40 ppm to about 120 ppm, about 50 ppm to about 60 ppm, about 50 ppm to about 70 ppm, about 50 ppm to about 80 ppm, about 50 ppm to about 90 ppm, about 50 ppm to about 100 ppm, about 50 ppm to about 110 ppm, about 50 ppm to about 120 ppm, about 60 ppm to about 70 ppm, about 60 ppm to about 80 ppm, about 60 ppm to about 90 ppm, about 60 ppm to about 100 ppm, about 60 ppm to about 110 ppm, about 60 ppm to about 120 ppm, about 70 ppm to about 80 ppm, about 70 ppm to about 90 ppm, about 70 ppm to about 100 ppm, about 70 ppm to about 110 ppm, about 70 ppm to about 120 ppm, about 80 ppm to about 90 ppm, about 80 ppm to about 100 ppm, about 80 ppm to about 110 ppm, about 80 ppm to about 120 ppm, about 90 ppm to about 100 ppm, about 90 ppm to about 110 ppm, about 90 ppm to about 120 ppm, about 100 ppm to about 110 ppm, about 100 ppm to about 120 ppm, or about 110 ppm to about 120 ppm.

Aspects of the present specification can also be described as follows:

1. A composition comprising, consisting essentially of, or consisting of hypochlorous acid or free available chlorine and one or more disinfectants.
2. The composition according to embodiment 1, wherein the hypochlorous acid or free available chlorine is in an amount of about 0.00005%, about 0.00006%, about 0.00007%, about 0.000075%, about 0.00008%, about 0.00009%, about 0.0001%, about 0.0005%, about 0.001%, about 0.0015%, about 0.002%, about 0.0025%, about 0.003%, about 0.0035%, about 0.004%, about 0.0045%, about 0.005%, about 0.0055%, about 0.006%, about 0.007%, about 0.0075%, about 0.008%, about 0.009%, about 0.01%, about 0.02%, about 0.03%, about 0.04%, about 0.05%, about 0.06%, about 0.07%, about 0.075%, about 0.08%, about 0.09%, about 0.10%, about 0.11%, about 0.12%, about 0.13%, about 0.14%, or about 0.15% by weight of the composition or at least 0.00005%, at least 0.00006%, at least 0.00007%, at least 0.000075%, at least 0.00008%, at least 0.00009%, at least 0.0001%, at least 0.0005%, at least 0.001%, at least 0.0015%, at least 0.002%, at least 0.0025%, at least 0.003%, at least 0.0035%, at least 0.004%, at least 0.0045%, at least 0.005%, at least 0.0055%, at least 0.006%, at least 0.007%, at least 0.0075%, at least 0.008%, at least 0.009%, at least 0.01%, at least 0.02%, at least 0.03%, at least 0.04%, at least 0.05%, at least 0.06%, at least 0.07%, at least 0.075%, at least 0.08%, at least 0.09%, at least 0.10%, at least 0.11%, at least 0.12%, at least 0.13%, at least 0.14%, or at least 0.15% by weight of the composition or at most 0.00005%, at most 0.00006%, at most 0.00007%, at most 0.000075%, at most 0.00008%, at most 0.00009%, at most 0.0001%, at most 0.0005%, at most 0.001%, at most 0.0015%, at most 0.002%, at most 0.0025%, at most 0.003%, at most 0.0035%, at most 0.004%, at most 0.0045%, at most 0.005%, at most 0.0055%, at most 0.006%, at most 0.007%, at most 0.0075%, at most 0.008%, at most 0.009%, at most 0.01%, at most 0.02%, at most 0.03%, at most 0.04%, at most 0.05%, at most 0.06%, at most 0.07%, at most 0.075%, at most 0.08%, at most 0.09%, at most 0.10%, at most 0.11%, at most 0.12%, at most 0.13%, at most 0.14%, or at most 0.15% by weight of the composition or about 0.00075% to about 0.002%, about 0.00075% to about 0.003%, about 0.00075% to about 0.004%, about 0.00075% to about 0.005%, about 0.00075% to about 0.006%, about 0.00075% to about 0.007%, about 0.00075% to about 0.008%, about 0.00075% to about 0.009%, about 0.00075% to about 0.01%, about 0.001% to about 0.002%, about 0.001% to about 0.003%, about 0.001% to about 0.004%, about 0.001% to about 0.005%, about 0.001% to about 0.006%, about 0.001% to about 0.007%, about 0.001% to about 0.008%, about 0.001% to about 0.009%, about 0.001% to about 0.01%, about 0.002% to about 0.003%, about 0.002% to about 0.004%, about 0.002% to about 0.005%, about 0.002% to about 0.006%, about 0.002% to about 0.007%, about 0.002% to about 0.008%, about 0.002% to about 0.009%, about 0.002% to about 0.01% by weight of the composition
3. The composition according to embodiment 1, wherein the hypochlorous acid or free available chlorine is in an amount of 0.05 ppm, 0.10 ppm, 0.15 ppm, 0.20 ppm, 0.25 ppm, 0.30 ppm, 0.35 ppm, 0.40 ppm, 0.45 ppm, 0.50 ppm, 0.55 ppm, 0.60 ppm, 0.65 ppm, 0.70 ppm, 0.75 ppm, 0.80 ppm, 0.85 ppm, 0.90 ppm, 0.95 ppm, 1 ppm, 5 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm or at least 0.05 ppm, at least 0.10 ppm, at least 0.20 ppm, at least 0.30 ppm, at least 0.40 ppm, at least 0.50 ppm, at least 0.60 ppm, at least 0.70 ppm, at least 0.80 ppm, at least 0.90 ppm, at least 1 ppm, at least 10 ppm, at least 20 ppm, at least 30 ppm, at least 40 ppm, at least 50 ppm, at least 60 ppm, at least 70 ppm, at least 80 ppm, at least 90 ppm, at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, at least 1,000 ppm, at least 1,025 ppm, at least 1,050 ppm, at least 1075 ppm, at least 1,100 ppm, at least 1,125 ppm, at least 1,150 ppm, at least 1,175 ppm, at least 1,200 ppm, at least 1,225 ppm, at least 1,250 ppm, at least 1,275 ppm, at least 1,300 ppm, at least 1,325 ppm, at least 1,350 ppm, at least 1,375 ppm, at least 1,400 ppm, at least 1,425 ppm, at least 1,450 ppm, at least 1,475 ppm, or at least 1,500 ppm or at most 0.05 ppm, at most 0.10 ppm, at most 0.20 ppm, at most 0.30 ppm, at most 0.40 ppm, at most 0.50 ppm, at most 0.60 ppm, at most 0.70 ppm, at most 0.80 ppm, at most 0.90 ppm, at most 1 ppm, at most 10 ppm, at most 20 ppm, at most 30 ppm, at most 40 ppm, at most 50 ppm, at most 60 ppm, at most 70 ppm, at most 80 ppm, at most 90 ppm, at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, at most 1,000 ppm, at most 1,025 ppm, at most 1,050 ppm, at most 1075 ppm, at most 1,100 ppm, at most 1,125 ppm, at most 1,150 ppm, at most 1,175 ppm, at most 1,200 ppm, at most 1,225 ppm, at most 1,250 ppm, at most 1,275 ppm, at most 1,300 ppm, at most 1,325 ppm, at most 1,350 ppm, at most 1,375 ppm, at most 1,400 ppm, at most 1,425 ppm, at most 1,450 ppm, at most 1,475 ppm, or at most 1,500 ppm or about 0.5 ppm to about 20 ppm, about 0.5 ppm to about 25 ppm, about 0.5 ppm to about 30 ppm, about 0.5 ppm to about 35 ppm, about 0.5 ppm to about 40 ppm, about 0.5 ppm to about 45 ppm, about 0.5 ppm to about 50 ppm, about 0.5 ppm to about 55 ppm, about 0.5 ppm to about 60 ppm, about 0.5 ppm to about 65 ppm, about 0.5 ppm to about 70 ppm, about 0.5 ppm to about 75 ppm, about 0.5 ppm to about 80 ppm, about 0.5 ppm to about 85 ppm, about 0.5 ppm to about 90 ppm, about 0.5 ppm to about 95 ppm, about 0.5 ppm to about 100 ppm, about 0.75 ppm to about 20 ppm, about 0.75 ppm to about 25 ppm, about 0.75 ppm to about 30 ppm, about 0.75 ppm to about 35 ppm, about 0.75 ppm to about 40 ppm, about 0.75 ppm to about 45 ppm, about 0.75 ppm to about 50 ppm, about 0.75 ppm to about 55 ppm, about 0.75 ppm to about 60 ppm, about 0.75 ppm to about 65 ppm, about 0.75 ppm to about 70 ppm, about 0.75 ppm to about 75 ppm, about 0.75 ppm to about 80 ppm, about 0.75 ppm to about 85 ppm, about 0.75 ppm to about 90 ppm, about 0.75 ppm to about 95 ppm, about 0.75 ppm to about 100 ppm, about 1 ppm to about 20 ppm, about 1 ppm to about 25 ppm, about 1 ppm to about 30 ppm, about 1 ppm to about 35 ppm, about 1 ppm to about 40 ppm, about 1 ppm to about 45 ppm, about 1 ppm to about 50 ppm, about 1 ppm to about 55 ppm, about 1 ppm to about 60 ppm, about 1 ppm to about 65 ppm, about 1 ppm to about 70 ppm, about 1 ppm to about 75 ppm, about 1 ppm to about 80 ppm, about 1 ppm to about 85 ppm, about 1 ppm to about 90 ppm, about 1 ppm to about 95 ppm, about 1 ppm to about 100 ppm, about 5 ppm to about 20 ppm, about 5 ppm to about 25 ppm, about 5 ppm to about 30 ppm, about 5 ppm to about 35 ppm, about 5 ppm to about 40 ppm, about 5 ppm to about 45 ppm, about 5 ppm to about 50 ppm, about 5 ppm to about 55 ppm, about 5 ppm to about 60 ppm, about 5 ppm to about 65 ppm, about 5 ppm to about 70 ppm, about 5 ppm to about 75 ppm, about 5 ppm to about 80 ppm, about 5 ppm to about 85 ppm, about 5 ppm to about 90 ppm, about 5 ppm to about 95 ppm, about 5 ppm to about 100 ppm, about 10 ppm to about 20 ppm, about 10 ppm to about 25 ppm, about 10 ppm to about 30 ppm, about 10 ppm to about 35 ppm, about 10 ppm to about 40 ppm, about 10 ppm to about 45 ppm, about 10 ppm to about 50 ppm, about 10 ppm to about 55 ppm, about 10 ppm to about 60 ppm, about 10 ppm to about 65 ppm, about 10 ppm to about 70 ppm, about 10 ppm to about 75 ppm, about 10 ppm to about 80 ppm, about 10 ppm to about 85 ppm, about 10 ppm to about 90 ppm, about 10 ppm to about 95 ppm, or about 10 ppm to about 100 ppm or about 1 ppm to about 25 ppm, about 1 ppm to about 50 ppm, about 1 ppm to about 75 ppm, about 1 ppm to about 100 ppm, about 1 ppm to about 125 ppm, about 1 ppm to about 150 ppm, about 1 ppm to about 175 ppm, about 1 ppm to about 200 ppm, about 1 ppm to about 225 ppm, about 1 ppm to about 250 ppm, about 1 ppm to about 275 ppm, about 1 ppm to about 300 ppm, about 1 ppm to about 325 ppm, about 1 ppm to about 350 ppm, about 1 ppm to about 375 ppm, about 1 ppm to about 400 ppm, about 10 ppm to about 25 ppm, about 10 ppm to about 50 ppm, about 10 ppm to about 75 ppm, about 10 ppm to about 100 ppm, about 10 ppm to about 125 ppm, about 10 ppm to about 150 ppm, about 10 ppm to about 175 ppm, about 10 ppm to about 200 ppm, about 10 ppm to about 225 ppm, about 10 ppm to about 250 ppm, about 10 ppm to about 275 ppm, about 10 ppm to about 300 ppm, about 10 ppm to about 325 ppm, about 10 ppm to about 350 ppm, about 10 ppm to about 375 ppm, about 10 ppm to about 400 ppm, about 25 ppm to about 50 ppm, about 25 ppm to about 75 ppm, about 25 ppm to about 100 ppm, about 25 ppm to about 125 ppm, about 25 ppm to about 150 ppm, about 25 ppm to about 175 ppm, about 25 ppm to about 200 ppm, about 25 ppm to about 225 ppm, about 25 ppm to about 250 ppm, about 25 ppm to about 275 ppm, about 25 ppm to about 300 ppm, about 25 ppm to about 325 ppm, about 25 ppm to about 350 ppm, about 25 ppm to about 375 ppm, about 25 ppm to about 400 ppm, about 50 ppm to about 75 ppm, about 50 ppm to about 100 ppm, about 50 ppm to about 125 ppm, about 50 ppm to about 150 ppm, about 50 ppm to about 175 ppm, about 50 ppm to about 200 ppm, about 50 ppm to about 225 ppm, about 50 ppm to about 250 ppm, about 50 ppm to about 275 ppm, about 50 ppm to about 300 ppm, about 50 ppm to about 325 ppm, about 50 ppm to about 350 ppm, about 50 ppm to about 375 ppm, about 50 ppm to about 400 ppm, about 75 ppm to about 100 ppm, about 75 ppm to about 125 ppm, about 75 ppm to about 150 ppm, about 75 ppm to about 175 ppm, about 75 ppm to about 200 ppm, about 75 ppm to about 225 ppm, about 75 ppm to about 250 ppm, about 75 ppm to about 275 ppm, about 75 ppm to about 300 ppm, about 75 ppm to about 325 ppm, about 75 ppm to about 350 ppm, about 75 ppm to about 375 ppm, about 75 ppm to about 400 ppm, about 100 ppm to about 125 ppm, about 100 ppm to about 150 ppm, about 100 ppm to about 175 ppm, about 100 ppm to about 200 ppm, about 100 ppm to about 225 ppm, about 100 ppm to about 250 ppm, about 100 ppm to about 275 ppm, about 100 ppm to about 300 ppm, about 100 ppm to about 325 ppm, about 100 ppm to about 350 ppm, about 100 ppm to about 375 ppm, about 100 ppm to about 400 ppm, about 150 ppm to about 175 ppm, about 150 ppm to about 200 ppm, about 150 ppm to about 225 ppm, about 150 ppm to about 250 ppm, about 150 ppm to about 275 ppm, about 150 ppm to about 300 ppm, about 150 ppm to about 325 ppm, about 150 ppm to about 350 ppm, about 150 ppm to about 375 ppm, about 150 ppm to about 400 ppm, about 200 ppm to about 225 ppm, about 200 ppm to about 250 ppm, about 200 ppm to about 275 ppm, about 200 ppm to about 300 ppm, about 200 ppm to about 325 ppm, about 200 ppm to about 350 ppm, about 200 ppm to about 375 ppm, about 200 ppm to about 400 ppm, about 250 ppm to about 275 ppm, about 250 ppm to about 300 ppm, about 250 ppm to about 325 ppm, about 250 ppm to about 350 ppm, about 250 ppm to about 375 ppm, about 250 ppm to about 400 ppm, about 300 ppm to about 325 ppm, about 300 ppm to about 350 ppm, about 300 ppm to about 375 ppm, about 300 ppm to about 400 ppm, about 350 ppm to about 375 ppm, about 350 ppm to about 400 ppm, about 375 ppm to about 400 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 400 ppm to about 1,100 ppm, about 400 ppm to about 1,200 ppm, about 400 ppm to about 1,300 ppm, about 400 ppm to about 1,400 ppm, about 400 ppm to about 1,500 ppm, about 500 ppm to about 600 ppm, about 500 ppm to about 700 ppm, about 500 ppm to about 800 ppm, about 500 ppm to about 900 ppm, about 500 ppm to about 1,000 ppm, about 500 ppm to about 1,100 ppm, about 500 ppm to about 1,200 ppm, about 500 ppm to about 1,300 ppm, about 500 ppm to about 1,400 ppm, about 500 ppm to about 1,500 ppm, about 600 ppm to about 700 ppm, about 600 ppm to about 800 ppm, about 600 ppm to about 900 ppm, about 600 ppm to about 1,000 ppm, about 600 ppm to about 1,100 ppm, about 600 ppm to about 1,200 ppm, about 600 ppm to about 1,300 ppm, about 600 ppm to about 1,400 ppm, about 600 ppm to about 1,500 ppm, about 700 ppm to about 800 ppm, about 700 ppm to about 900 ppm, about 700 ppm to about 1,000 ppm, about 700 ppm to about 1,100 ppm, about 700 ppm to about 1,200 ppm, about 700 ppm to about 1,300 ppm, about 700 ppm to about 1,400 ppm, about 700 ppm to about 1,500 ppm, about 800 ppm to about 900 ppm, about 800 ppm to about 1,000 ppm, about 800 ppm to about 1,100 ppm, about 800 ppm to about 1,200 ppm, about 800 ppm to about 1,300 ppm, about 800 ppm to about 1,400 ppm, about 800 ppm to about 1,500 ppm, about 900 ppm to about 1,000 ppm, about 900 ppm to about 1,100 ppm, about 900 ppm to about 1,200 ppm, about 900 ppm to about 1,300 ppm, about 900 ppm to about 1,400 ppm, about 900 ppm to about 1,500 ppm, about 1,000 ppm to about 1,100 ppm, about 1,000 ppm to about 1,200 ppm, about 1,000 ppm to about 1,300 ppm, about 1,000 ppm to about 1,400 ppm, about 1,000 ppm to about 1,500 ppm, about 1,100 ppm to about 1,200 ppm, about 1,100 ppm to about 1,300 ppm, about 1,100 ppm to about 1,400 ppm, about 1,100 ppm to about 1,500 ppm, about 1,200 ppm to about 1,300 ppm, about 1,200 ppm to about 1,400 ppm, about 1,200 ppm to about 1,500 ppm, about 1,300 ppm to about 1,400 ppm, about 1,300 ppm to about 1,500 ppm, or about 1,400 ppm to about 1,500 ppm.

4. The composition according to any one of embodiments 1-3, wherein the one or more disinfectants are in an amount of about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition, or at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0% by weight of the composition, or at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition, or about 0.1% to about 0.5%, about 0.1% to about 0.75%, about 0.1% to about 1.0%, about 0.1% to about 1.5%, about 0.1% to about 2.0%, about 0.1% to about 2.5%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0% or about 5.0% to about 15.0% by weight of the composition.

5. The composition according to any one of embodiments 1-3, wherein the one or more disinfectants are in an amount of about 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, or 1,000 ppm, or at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, or at least 1,000 ppm, or at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, or at most 1,000 ppm, or about 100 ppm to about 200 ppm, about 100 ppm to about 300 ppm, about 100 ppm to about 400 ppm, about 100 ppm to about 500 ppm, about 100 ppm to about 600 ppm, about 100 ppm to about 700 ppm, about 100 ppm to about 800 ppm, about 100 ppm to about 900 ppm, about 100 ppm to about 1,000 ppm, about 200 ppm to about 300 ppm, about 200 ppm to about 400 ppm, about 200 ppm to about 500 ppm, about 200 ppm to about 600 ppm, about 200 ppm to about 700 ppm, about 200 ppm to about 800 ppm, about 200 ppm to about 900 ppm, about 200 ppm to about 1,000 ppm, about 300 ppm to about 400 ppm, about 300 ppm to about 500 ppm, about 300 ppm to about 600 ppm, about 300 ppm to about 700 ppm, about 300 ppm to about 800 ppm, about 300 ppm to about 900 ppm, about 300 ppm to about 1,000 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 500 ppm to about 600 ppm, about 500 ppm to about 700 ppm, about 500 ppm to about 800 ppm, about 500 ppm to about 900 ppm, about 500 ppm to about 1,000 ppm, about 600 ppm to about 700 ppm, about 600 ppm to about 800 ppm, about 600 ppm to about 900 ppm, about 600 ppm to about 1,000 ppm, about 700 ppm to about 800 ppm, about 700 ppm to about 900 ppm, about 700 ppm to about 1,000 ppm, about 800 ppm to about 900 ppm, about 800 ppm to about 1,000 ppm, or about 900 ppm to about 1,000 ppm.

6. The composition according to any one of embodiments 1-5, wherein the one or more disinfectants include one or more compounds containing a guanide moiety or functional group, one or more aldehyde-containing compounds, one or more organic peroxides, or any combination thereof.

7. The composition according to embodiment 6, wherein the one or more guanide-containing compounds comprise, consist essentially of, or consist of comprise, consist essentially of, or consist of a biguanide, a biguanide-containing compound, a biguanidine, a biguanidine-containing compound, a triguanide, a triguanide-containing compound, or any combination thereof.

8. The composition according to embodiment 7, wherein the one or more biguanide-containing compounds include a polyhexamethylene biguanide (PHMB), a polyaminopropyl biguanide (PAPB), a 1,1'-(1,6-Hexanediyl)bis{2-[N'-(2-ethylhexyl)carbamimidoyl]guanidine} (alexidine), a chlorhexidine, a chlorhexidine gluconate, or any combination thereof.

9. The composition according to embodiment 6, wherein the one or more aldehyde-containing compounds include one or more aldehydes, one or more dialdehydes, or any combination thereof.

10. The composition according to embodiment 9, wherein the one or more aldehydes includes one or more linear aldehydes, one or more branched aldehydes, one or more cyclic aldehydes, one or more aromatic aldehydes, or any combination thereof.

11. The composition according to embodiment 9 or 10, wherein the one or more aldehydes includes formaldehyde, acetaldehyde, propionaldehyde, butyraldehyde, or any combination thereof.

12. The composition according to embodiment 9, wherein the one or more dialdehydes includes one or more linear dialdehydes, one or more branched dialdehydes, one or more cyclic dialdehydes, one or more aromatic dialdehydes, or any combination thereof.

13. The composition according to embodiment 9 or 10, wherein the one or more dialdehydes includes oxaldehyde, malondialdehyde, glutaraldehyde, succinicdialdehyde, phthalaldehyde (ortho-phthalaldehyde), isophthalaldehyde (meta-phthalaldehyde), terephthalaldehyde (para-phthalaldehyde), or any combination thereof.

14. The composition according to embodiment 6, wherein the one or more organic peroxides include benzoyl peroxide, ethaneperoxoic acid (peracetic acid), or any combination thereof.

15. The composition according to any one of embodiments 6-14, wherein the one or more guanide-containing compounds, one or more aldehyde-containing compounds, and/or one or more organic peroxides are in an amount of about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 6.5%, about 7.0%, about 7.5%, about 8.0%, about 8.5%, about 9.0%, about 9.5%, about 10.0%. about 11%, about 12%, about 13%, about 14%, about 15%, about 20%, about 25%, or about 30% by weight of the composition, or at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, at least 10.0%, at least 11%, at least 12%, at least 13%, at least 14%, at least 15%, at least 20%, at least 25%, or at least 30% by weight of the composition, or at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0%, at most 10.0%, at most 11%, at most 12%, at most 13%, at most 14%, at most 15%, at most 20%, at most 25%, or at most 30% by weight of the composition, or about 0.1% to about 0.5%, about 0.1% to about 0.75%, about 0.1% to about 1.0%, about 0.1% to about 1.5%, about 0.1% to about 2.0%, about 0.1% to about 2.5%, about 0.1% to about 3.0%, about 0.1% to about 3.5%, about 0.1% to about 4.0%, about 0.1% to about 4.5%, about 0.1% to about 5.0%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.2% to about 3.0%, about 0.2% to about 3.5%, about 0.2% to about 4.0%, about 0.2% to about 4.5%, about 0.2% to about 5.0%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 1.0% to about 15.0%, about 1.0% to about 20.0%, about 1.0% to about 25.0%, about 1.0% to about 30.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 2.0% to about 15.0%, about 2.0% to about 20.0%, about 2.0% to about 25.0%, about 2.0% to about 30.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0%, about 5.0% to about 15.0%, about 5.0% to about 20.0%, about 5.0% to about 25.0%, about 5.0% to about 30.0%, about 6.0% to about 7.0%, about 6.0% to about 7.5%, about 6.0% to about 8.0%, about 6.0% to about 9.0%, about 6.0% to about 10.0%, about 6.0% to about 11.0%, about 6.0% to about 12.0%, about 6.0% to about 13.0%, about 6.0% to about 14.0%, about 6.0% to about 15.0%, about 6.0% to about 20.0%, about 6.0% to about 25.0%, about 6.0% to about 30.0%, about 7.0% to about 8.0%, about 7.0% to about 9.0%, about 7.0% to about 10.0%, about 7.0% to about 11.0%, about 7.0% to about 12.0%, about 7.0% to about 13.0%, about 7.0% to about 14.0%, about 7.0% to about 15.0%, about 7.0% to about 20.0%, about 7.0% to about 25.0%, about 7.0% to about 30.0%, about 8.0% to about 9.0%, about 8.0% to about 10.0%, about 8.0% to about 11.0%, about 8.0% to about 12.0%, about 8.0% to about 13.0%, about 8.0% to about 14.0%, about 8.0% to about 15.0%, about 8.0% to about 20.0%, about 8.0% to about 25.0%, about 8.0% to about 30.0%, about 9.0% to about 10.0%, about 9.0% to about 11.0%, about 9.0% to about 12.0%, about 9.0% to about 13.0%, about 9.0% to about 14.0%, about 9.0% to about 15.0%, about 9.0% to about 20.0%, about 9.0% to about 25.0%, about 9.0% to about 30.0%, about 10.0% to about 11.0%, about 10.0% to about 12.0%, about 10.0% to about 13.0%, about 10.0% to about 14.0%, about 10.0% to about 15.0%, about 10.0% to about 20.0%, about 10.0% to about 25.0%, about 10.0% to about 30.0%, about 15.0% to about 20.0%, about 15.0% to about 25.0%, about 15.0% to about 30.0%, about 20.0% to about 25.0%, about 20.0% to about 30.0%, or about 20.0% to about 30.0%, by weight of the composition.

16. The composition according to any one of embodiments 6-14, wherein the one or more aldehydes and/or one or more dialdehydes are in an amount of about 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, or 1,000 ppm, or at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, or at least 1,000 ppm, or at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, or at most 1,000 ppm, 17. The composition according to any one of embodiments 6-14, wherein the one or more aldehydes and/or one or more dialdehydes are in an amount of about 100 ppm to about 200 ppm, about 100 ppm to about 300 ppm, about 100 ppm to about 400 ppm, about 100 ppm to about 500 ppm, about 100 ppm to about 600 ppm, about 100 ppm to about 700 ppm, about 100 ppm to about 800 ppm, about 100 ppm to about 900 ppm, about 100 ppm to about 1,000 ppm, about 200 ppm to about 300 ppm, about 200 ppm to about 400 ppm, about 200 ppm to about 500 ppm, about 200 ppm to about 600 ppm, about 200 ppm to about 700 ppm, about 200 ppm to about 800 ppm, about 200 ppm to about 900 ppm, about 200 ppm to about 1,000 ppm, about 300 ppm to about 400 ppm, about 300 ppm to about 500 ppm, about 300 ppm to about 600 ppm, about 300 ppm to about 700 ppm, about 300 ppm to about 800 ppm, about 300 ppm to about 900 ppm, about 300 ppm to about 1,000 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 500 ppm to about 600 ppm, about 500 ppm to about 700 ppm, about 500 ppm to about 800 ppm, about 500 ppm to about 900 ppm, about 500 ppm to about 1,000 ppm, about 600 ppm to about 700 ppm, about 600 ppm to about 800 ppm, about 600 ppm to about 900 ppm, about 600 ppm to about 1,000 ppm, about 700 ppm to about 800 ppm, about 700 ppm to about 900 ppm, about 700 ppm to about 1,000 ppm, about 800 ppm to about 900 ppm, about 800 ppm to about 1,000 ppm, or about 900 ppm to about 1,000 ppm.

18. The composition according to any one of embodiments 1-17, further comprising, consisting essentially of, or consisting of one or more surfactants which act as foaming agents.

19. A composition comprising, consisting essentially of, or consisting of hypochlorous acid or free available chlorine and one or more surfactants which act as foaming agents.

20. The composition according to embodiment 19, wherein the hypochlorous acid or free available chlorine is in an amount of 0.00005%, 0.00006%, 0.00007%, 0.000075%, 0.00008%, 0.00009%, 0.0001%, 0.0005%, 0.001%, 0.0015%, 0.002%, 0.0025%, 0.003%, 0.0035%, 0.004%, 0.0045%, 0.005%, 0.0055%, 0.006%, 0.007%, 0.0075%, 0.008%, 0.009%, 0.01%, 0.02%, 0.03%, 0.04% or 0.05% by weight of the composition or at least 0.00005%, at least 0.00006%, at least 0.00007%, at least 0.000075%, at least 0.00008%, at least 0.00009%, at least 0.0001%, at least 0.0005%, at least 0.001%, at least 0.0015%, at least 0.002%, at least 0.0025%, at least 0.003%, at least 0.0035%, at least 0.004%, at least 0.0045%, at least 0.005%, at least 0.0055%, at least 0.006%, at least 0.007%, at least 0.0075%, at least 0.008%, at least 0.009%, at least 0.01%, at least 0.02%, at least 0.03%, at least 0.04% or at least 0.05% by weight of the composition or at most 0.00005%, at most 0.00006%, at most 0.00007%, at most 0.000075%, at most 0.00008%, at most 0.00009%, at most 0.0001%, at most 0.0005%, at most 0.001%, at most 0.0015%, at most 0.002%, at most 0.0025%, at most 0.003%, at most 0.0035%, at most 0.004%, at most 0.0045%, at most 0.005%, at most 0.0055%, at most 0.006%, at most 0.007%, at most 0.0075%, at most 0.008%, at most 0.009%, at most 0.01%, at most 0.02%, at most 0.03%, at most 0.04% or at most 0.05% by weight of the composition or about 0.00075% to about 0.002%, about 0.00075% to about 0.003%, about 0.00075% to about 0.004%, about 0.00075% to about 0.005%, about 0.00075% to about 0.006%, about 0.00075% to about 0.007%, about 0.00075% to about 0.008%, about 0.00075% to about 0.009%, about 0.00075% to about 0.01%, about 0.001% to about 0.002%, about 0.001% to about 0.003%, about 0.001% to about 0.004%, about 0.001% to about 0.005%, about 0.001% to about 0.006%, about 0.001% to about 0.007%, about 0.001% to about 0.008%, about 0.001% to about 0.009%, about 0.001% to about 0.01%, about 0.002% to about 0.003%, about 0.002% to about 0.004%, about 0.002% to about 0.005%, about 0.002% to about 0.006%, about 0.002% to about 0.007%, about 0.002% to about 0.008%, about 0.002% to about 0.009%, about 0.002% to about 0.01% by weight of the composition 21. The composition according to embodiment 19, wherein the hypochlorous acid or free available chlorine is in an amount of 0.05 ppm, 0.10 ppm, 0.15 ppm, 0.20 ppm, 0.25 ppm, 0.30 ppm, 0.35 ppm, 0.40 ppm, 0.45 ppm, 0.50 ppm, 0.55 ppm, 0.60 ppm, 0.65 ppm, 0.70 ppm, 0.75 ppm, 0.80 ppm, 0.85 ppm, 0.90 ppm, 0.95 ppm, 1 ppm, 5 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm or at least 0.05 ppm, at least 0.10 ppm, at least 0.20 ppm, at least 0.30 ppm, at least 0.40 ppm, at least 0.50 ppm, at least 0.60 ppm, at least 0.70 ppm, at least 0.80 ppm, at least 0.90 ppm, at least 1 ppm, at least 10 ppm, at least 20 ppm, at least 30 ppm, at least 40 ppm, at least 50 ppm, at least 60 ppm, at least 70 ppm, at least 80 ppm, at least 90 ppm, at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, at least 1,000 ppm, at least 1,025 ppm, at least 1,050 ppm, at least 1075 ppm, at least 1,100 ppm, at least 1,125 ppm, at least 1,150 ppm, at least 1,175 ppm, at least 1,200 ppm, at least 1,225 ppm, at least 1,250 ppm, at least 1,275 ppm, at least 1,300 ppm, at least 1,325 ppm, at least 1,350 ppm, at least 1,375 ppm, at least 1,400 ppm, at least 1,425 ppm, at least 1,450 ppm, at least 1,475 ppm, or at least 1,500 ppm or at most 0.05 ppm, at most 0.10 ppm, at most 0.20 ppm, at most 0.30 ppm, at most 0.40 ppm, at most 0.50 ppm, at most 0.60 ppm, at most 0.70 ppm, at most 0.80 ppm, at most 0.90 ppm, at most 1 ppm, at most 10 ppm, at most 20 ppm, at most 30 ppm, at most 40 ppm, at most 50 ppm, at most 60 ppm, at most 70 ppm, at most 80 ppm, at most 90 ppm, at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, at most 1,000 ppm, at most 1,025 ppm, at most 1,050 ppm, at most 1075 ppm, at most 1,100 ppm, at most 1,125 ppm, at most 1,150 ppm, at most 1,175 ppm, at most 1,200 ppm, at most 1,225 ppm, at most 1,250 ppm, at most 1,275 ppm, at most 1,300 ppm, at most 1,325 ppm, at most 1,350 ppm, at most 1,375 ppm, at most 1,400 ppm, at most 1,425 ppm, at most 1,450 ppm, at most 1,475 ppm, or at most 1,500 ppm or about 0.5 ppm to about 20 ppm, about 0.5 ppm to about 25 ppm, about 0.5 ppm to about 30 ppm, about 0.5 ppm to about 35 ppm, about 0.5 ppm to about 40 ppm, about 0.5 ppm to about 45 ppm, about 0.5 ppm to about 50 ppm, about 0.5 ppm to about 55 ppm, about 0.5 ppm to about 60 ppm, about 0.5 ppm to about 65 ppm, about 0.5 ppm to about 70 ppm, about 0.5 ppm to about 75 ppm, about 0.5 ppm to about 80 ppm, about 0.5 ppm to about 85 ppm, about 0.5 ppm to about 90 ppm, about 0.5 ppm to about 95 ppm, about 0.5 ppm to about 100 ppm, about 0.75 ppm to about 20 ppm, about 0.75 ppm to about 25 ppm, about 0.75 ppm to about 30 ppm, about 0.75 ppm to about 35 ppm, about 0.75 ppm to about 40 ppm, about 0.75 ppm to about 45 ppm, about 0.75 ppm to about 50 ppm, about 0.75 ppm to about 55 ppm, about 0.75 ppm to about 60 ppm, about 0.75 ppm to about 65 ppm, about 0.75 ppm to about 70 ppm, about 0.75 ppm to about 75 ppm, about 0.75 ppm to about 80 ppm, about 0.75 ppm to about 85 ppm, about 0.75 ppm to about 90 ppm, about 0.75 ppm to about 95 ppm, about 0.75 ppm to about 100 ppm, about 1 ppm to about 20 ppm, about 1 ppm to about 25 ppm, about 1 ppm to about 30 ppm, about 1 ppm to about 35 ppm, about 1 ppm to about 40 ppm, about 1 ppm to about 45 ppm, about 1 ppm to about 50 ppm, about 1 ppm to about 55 ppm, about 1 ppm to about 60 ppm, about 1 ppm to about 65 ppm, about 1 ppm to about 70 ppm, about 1 ppm to about 75 ppm, about 1 ppm to about 80 ppm, about 1 ppm to about 85 ppm, about 1 ppm to about 90 ppm, about 1 ppm to about 95 ppm, about 1 ppm to about 100 ppm, about 5 ppm to about 20 ppm, about 5 ppm to about 25 ppm, about 5 ppm to about 30 ppm, about 5 ppm to about 35 ppm, about 5 ppm to about 40 ppm, about 5 ppm to about 45 ppm, about 5 ppm to about 50 ppm, about 5 ppm to about 55 ppm, about 5 ppm to about 60 ppm, about 5 ppm to about 65 ppm, about 5 ppm to about 70 ppm, about 5 ppm to about 75 ppm, about 5 ppm to about 80 ppm, about 5 ppm to about 85 ppm, about 5 ppm to about 90 ppm, about 5 ppm to about 95 ppm, about 5 ppm to about 100 ppm, about 10 ppm to about 20 ppm, about 10 ppm to about 25 ppm, about 10 ppm to about 30 ppm, about 10 ppm to about 35 ppm, about 10 ppm to about 40 ppm, about 10 ppm to about 45 ppm, about 10 ppm to about 50 ppm, about 10 ppm to about 55 ppm, about 10 ppm to about 60 ppm, about 10 ppm to about 65 ppm, about 10 ppm to about 70 ppm, about 10 ppm to about 75 ppm, about 10 ppm to about 80 ppm, about 10 ppm to about 85 ppm, about 10 ppm to about 90 ppm, about 10 ppm to about 95 ppm, or about 10 ppm to about 100 ppm or about 1 ppm to about 25 ppm, about 1 ppm to about 50 ppm, about 1 ppm to about 75 ppm, about 1 ppm to about 100 ppm, about 1 ppm to about 125 ppm, about 1 ppm to about 150 ppm, about 1 ppm to about 175 ppm, about 1 ppm to about 200 ppm, about 1 ppm to about 225 ppm, about 1 ppm to about 250 ppm, about 1 ppm to about 275 ppm, about 1 ppm to about 300 ppm, about 1 ppm to about 325 ppm, about 1 ppm to about 350 ppm, about 1 ppm to about 375 ppm, about 1 ppm to about 400 ppm, about 10 ppm to about 25 ppm, about 10 ppm to about 50 ppm, about 10 ppm to about 75 ppm, about 10 ppm to about 100 ppm, about 10 ppm to about 125 ppm, about 10 ppm to about 150 ppm, about 10 ppm to about 175 ppm, about 10 ppm to about 200 ppm, about 10 ppm to about 225 ppm, about 10 ppm to about 250 ppm, about 10 ppm to about 275 ppm, about 10 ppm to about 300 ppm, about 10 ppm to about 325 ppm, about 10 ppm to about 350 ppm, about 10 ppm to about 375 ppm, about 10 ppm to about 400 ppm, about 25 ppm to about 50 ppm, about 25 ppm to about 75 ppm, about 25 ppm to about 100 ppm, about 25 ppm to about 125 ppm, about 25 ppm to about 150 ppm, about 25 ppm to about 175 ppm, about 25 ppm to about 200 ppm, about 25 ppm to about 225 ppm, about 25 ppm to about 250 ppm, about 25 ppm to about 275 ppm, about 25 ppm to about 300 ppm, about 25 ppm to about 325 ppm, about 25 ppm to about 350 ppm, about 25 ppm to about 375 ppm, about 25 ppm to about 400 ppm, about 50 ppm to about 75 ppm, about 50 ppm to about 100 ppm, about 50 ppm to about 125 ppm, about 50 ppm to about 150 ppm, about 50 ppm to about 175 ppm, about 50 ppm to about 200 ppm, about 50 ppm to about 225 ppm, about 50 ppm to about 250 ppm, about 50 ppm to about 275 ppm, about 50 ppm to about 300 ppm, about 50 ppm to about 325 ppm, about 50 ppm to about 350 ppm, about 50 ppm to about 375 ppm, about 50 ppm to about 400 ppm, about 75 ppm to about 100 ppm, about 75 ppm to about 125 ppm, about 75 ppm to about 150 ppm, about 75 ppm to about 175 ppm, about 75 ppm to about 200 ppm, about 75 ppm to about 225 ppm, about 75 ppm to about 250 ppm, about 75 ppm to about 275 ppm, about 75 ppm to about 300 ppm, about 75 ppm to about 325 ppm, about 75 ppm to about 350 ppm, about 75 ppm to about 375 ppm, about 75 ppm to about 400 ppm, about 100 ppm to about 125 ppm, about 100 ppm to about 150 ppm, about 100 ppm to about 175 ppm, about 100 ppm to about 200 ppm, about 100 ppm to about 225 ppm, about 100 ppm to about 250 ppm, about 100 ppm to about 275 ppm, about 100 ppm to about 300 ppm, about 100 ppm to about 325 ppm, about 100 ppm to about 350 ppm, about 100 ppm to about 375 ppm, about 100 ppm to about 400 ppm, about 150 ppm to about 175 ppm, about 150 ppm to about 200 ppm, about 150 ppm to about 225 ppm, about 150 ppm to about 250 ppm, about 150 ppm to about 275 ppm, about 150 ppm to about 300 ppm, about 150 ppm to about 325 ppm, about 150 ppm to about 350 ppm, about 150 ppm to about 375 ppm, about 150 ppm to about 400 ppm, about 200 ppm to about 225 ppm, about 200 ppm to about 250 ppm, about 200 ppm to about 275 ppm, about 200 ppm to about 300 ppm, about 200 ppm to about 325 ppm, about 200 ppm to about 350 ppm, about 200 ppm to about 375 ppm, about 200 ppm to about 400 ppm, about 250 ppm to about 275 ppm, about 250 ppm to about 300 ppm, about 250 ppm to about 325 ppm, about 250 ppm to about 350 ppm, about 250 ppm to about 375 ppm, about 250 ppm to about 400 ppm, about 300 ppm to about 325 ppm, about 300 ppm to about 350 ppm, about 300 ppm to about 375 ppm, about 300 ppm to about 400 ppm, about 350 ppm to about 375 ppm, about 350 ppm to about 400 ppm, about 375 ppm to about 400 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 400 ppm to about 1,100 ppm, about 400 ppm to about 1,200 ppm, about 400 ppm to about 1,300 ppm, about 400 ppm to about 1,400 ppm, about 400 ppm to about 1,500 ppm, about 500 ppm to about 600 ppm, about 500 ppm to about 700 ppm, about 500 ppm to about 800 ppm, about 500 ppm to about 900 ppm, about 500 ppm to about 1,000 ppm, about 500 ppm to about 1,100 ppm, about 500 ppm to about 1,200 ppm, about 500 ppm to about 1,300 ppm, about 500 ppm to about 1,400 ppm, about 500 ppm to about 1,500 ppm, about 600 ppm to about 700 ppm, about 600 ppm to about 800 ppm, about 600 ppm to about 900 ppm, about 600 ppm to about 1,000 ppm, about 600 ppm to about 1,100 ppm, about 600 ppm to about 1,200 ppm, about 600 ppm to about 1,300 ppm, about 600 ppm to about 1,400 ppm, about 600 ppm to about 1,500 ppm, about 700 ppm to about 800 ppm, about 700 ppm to about 900 ppm, about 700 ppm to about 1,000 ppm, about 700 ppm to about 1,100 ppm, about 700 ppm to about 1,200 ppm, about 700 ppm to about 1,300 ppm, about 700 ppm to about 1,400 ppm, about 700 ppm to about 1,500 ppm, about 800 ppm to about 900 ppm, about 800 ppm to about 1,000 ppm, about 800 ppm to about 1,100 ppm, about 800 ppm to about 1,200 ppm, about 800 ppm to about 1,300 ppm, about 800 ppm to about 1,400 ppm, about 800 ppm to about 1,500 ppm, about 900 ppm to about 1,000 ppm, about 900 ppm to about 1,100 ppm, about 900 ppm to about 1,200 ppm, about 900 ppm to about 1,300 ppm, about 900 ppm to about 1,400 ppm, about 900 ppm to about 1,500 ppm, about 1,000 ppm to about 1,100 ppm, about 1,000 ppm to about 1,200 ppm, about 1,000 ppm to about 1,300 ppm, about 1,000 ppm to about 1,400 ppm, about 1,000 ppm to about 1,500 ppm, about 1,100 ppm to about 1,200 ppm, about 1,100 ppm to about 1,300 ppm, about 1,100 ppm to about 1,400 ppm, about 1,100 ppm to about 1,500 ppm, about 1,200 ppm to about 1,300 ppm, about 1,200 ppm to about 1,400 ppm, about 1,200 ppm to about 1,500 ppm, about 1,300 ppm to about 1,400 ppm, about 1,300 ppm to about 1,500 ppm, or about 1,400 ppm to about 1,500 ppm.

22. The composition according to any one of embodiments 18-21, wherein the one or more surfactants include one or more ionic surfactants, one or more zwitterionic (amphoteric) surfactants, one or more non-ionic surfactants, one or more biosurfactants, or any combination thereof 23. The composition according to embodiment 22, wherein the one or more ionic surfactants include one or more anionic surfactants, one or more cationic surfactants, or any combination thereof.

24. The composition according to embodiment 23, wherein the one or more anionic surfactants include one or more alkyl sulfates, one or more alkyl ether sulfates, one or more docusates like dioctyl sodium sulfosuccinates, one or more sulfonate fluorosurfactants, one or more alkyldiphenyloxide, one or more alkyldiphenyloxide disulfonates, one or more potassium phosphate polyether esters, one or more alkyl benzene sulfonates, one or more alkyl aryl ether phosphates, one or more alkyl ether phosphates, one or more alkyl carboxylates, one or more carboxylate fluorosurfactants, sodium lauroyl sarcosinate, sodium hexyldiphenyl ether sulfonate (DOWFAX™ C6L), or any combination thereof.

25. The composition according to embodiment 24, wherein the one or more alkyl sulfates include ammonium lauryl sulfate, sodium lauryl sulfate (SDS), or any combination thereof.
26. The composition according to embodiment 24, wherein the one or more alkyl ether sulfates include sodium laureth sulfate, sodium myreth sulfate, or any combination thereof.
27. The composition according to embodiment 24, wherein the one or more docusates include dioctyl sodium sulfosuccinate.
28. The composition according to embodiment 24, wherein the one or more sulfonate fluorosurfactants include perfluorooctanesulfonate (PFOS), perfluorobutanesulfonate, or any combination thereof.
29. The composition according to embodiment 24, wherein the one or more alkyldiphenyloxide disulfonates include DOWFAX™ 2A1 (Disodium Lauryl Phenyl Ether Disulfonate), DOWFAX™ 3B2 (Disodium Decyl Phenyl Ether Disulfonate), DOWFAX™ C10L (Disodium Decyl Phenyl Ether Disulfonate), DOWFAX™ 2EP, DOWFAX™ 8390 (Disodium Cetyl Phenyl Ether Disulfonate), or any combination thereof.
30. The composition according to embodiment 24, wherein the one or more potassium phosphate polyether esters include TRITON™ H-55, TRITON™ H-66, or any combination thereof.
31. The composition according to embodiment 24, wherein the one or more alkyl carboxylates include fatty acid salts, sodium stearate, or any combination thereof.
32. The composition according to embodiment 24, wherein the one or more carboxylate fluorosurfactants include perfluorononanoate, perfluorooctanoate, or any combination thereof.
33. The composition according to embodiment 23, wherein the one or more cationic surfactants include one or more quaternary ammonium surfactants, pH-dependent primary amine surfactant, pH-dependent secondary amine surfactant, pH-dependent tertiary amine surfactant, or any combination thereof.
34. The composition according to embodiment 33, wherein the one or more quaternary ammonium surfactants include benzalkonium chloride (BAC), benzethonium chloride (BZT), benzododecinium bromide (or dimethyldodecylbenzylammonium bromide), bronidox, (or 5-bromo-5-nitro-1,3-dioxane), carbethopendecinium bromide, cetalkonium chloride (CKC), cetrimonium, cetrimide, cetylpyridinium chloride (CPC), cetyl trimethylammonium bromide (CTAB or cetrimonium bromide) and cetyl trimethylammonium chloride (CTAC or cetrimonium chloride), didecyldimethylammonium chloride (DDAC), dioctadecyldimethylammonium bromide (DODAB or dimethyldioctadecylammonium bromide), dioctadecyldimethylammonium chloride (DODAC or dimethyldioctadecylammonium chloride), docosyltrimethylammonium chloride (DCTAC or behentrimonium chloride), dofanium chloride, domiphen bromide, methylbenzethonium chloride, octenidine dihydrochloride, polidronium chloride, stearalkonium chloride (or dimethylbenzyloctadecylammonium), tetraethylammonium bromide, tetramethylammonium hydroxide (TMAH) and thonzonium bromide, or any combination thereof.
35. The composition according to embodiment 22, wherein the one or more Zwitterionic surfactants include one or more sultaines one or more betaines, one or more lecithins, 3-[(3-Cholamidopropyl)dimethylammonio]-1-propanesulfonate (CHAPS), or any combination thereof.
36. The composition according to embodiment 35, wherein the one or more sultaines include cocamidopropyl hydroxysultaine.
37. The composition according to embodiment 35, wherein the one or more betaines include cocamidopropyl betaine.
38. The composition according to embodiment 22, wherein the one or more non-ionic surfactants include one or more polyether nonionic surfactants, one or more polyhydroxyl nonionic surfactants, or any combination thereof.
39. The composition according to embodiment 22, wherein the one or more non-ionic surfactants include one or more alcohol ethoxylates, one or more alkylphenol ethoxylates, one or more phenol ethoxylates, one or more amide ethoxylates, one or more glyceride ethoxylates, one or more fatty acid ethoxylates, one or more fatty amine ethoxylates, or any combination thereof.
40. The composition according to embodiment 22, wherein the one or more non-ionic surfactants include one or more polyoxyethylene glycol sorbitan alkyl esters (or ethoxylated sorbital esters), one or more sorbital esters, one or more polyglycerol esters, one or more ethoxylated polyglycerol esters, one or more alkyl glucosides, one or more ethoxylated alkyl glucosides, one or more sucrose esters, one or more ethoxylated sucrose ester, one or more amine oxides, one or more ethoxylated alcohols, one or more ethoxylated aliphatic alcohols, one or more alkylamines, one or more ethoxylated alkylamines, one or more ethoxylated alkyl phenols, one or more alkyl polysaccharides, one or more ethoxylated alkyl polysaccharides, one or more ethoxylated fatty acids, one or more ethoxylated fatty alcohols, one or more ethoxylated fatty amines, one or more poloxamers (polyethylene-polypropylene copolymers), one or more linear secondary alcohol ethoxylates, one or more alkyl phenol polyglycol ethers, one or more polyethylene glycol alkyl aryl ethers, one or more polyoxyethylene glycol alkyl ethers, one or more polyoxyethylene glycol octylphenol ethers, one or more polyoxyethylene glycol alkylphenol ethers, one or more phenoxypolyethoxylethanols, one or more glucoside alkyl ethers, one or more maltoside alkyl ethers, one or more thioglucoside alkyl ethers, one or more digitonins, one or more glycerol alkyl esters, one or more alkyl aryl polyether sulfates, one or more alcohol sulfonates, one or more sorbitan alkyl esters, one or more glycerol alkyl esters, one or more cocamide ethanolamines, sucrose monolaurate, dodecyl dimethylamine oxide, sodium cholate, 2-dodecoxyethanol (LUBROL®-PX), or any combination thereof.
41. The composition according to embodiment 40, wherein the one or more polyoxyethylene glycol sorbitan alkyl esters (or ethoxylated sorbital esters) include polysorbate 20 sorbitan monooleate (TWEEN® 20), polysorbate 40 sorbitan monooleate (TWEEN® 40), polysorbate 60 sorbitan monooleate (TWEEN® 60), polysorbate 61 sorbitan monooleate (TWEEN® 61), polysorbate 65 sorbitan monooleate (TWEEN® 65), polysorbate 80 sorbitan monooleate (TWEEN® 80), polysorbate 81 sorbitan monooleate (TWEEN® 81), polysorbate 85 sorbitan monooleate (TWEEN® 85), or any combination thereof.
42. The composition according to embodiment 40, wherein the one or more sorbital esters include sorbitan monooleate, sorbitan monolaurate, sorbitan monopalmitate, sorbitan monostearate, sorbitan tristearate, or any combination thereof.
43. The composition according to embodiment 40, wherein the one or more polyglycerol esters include glycerol monooleate, glycerol monolaurate, glycerol monopalmitate, glycerol monostearate, glycerol trioleate, glycerol ricinoleate, glycerol tristearate, or any combination thereof.
44. The composition according to embodiment 40, wherein the one or more alkyl glucosides include arachidyl glucoside, $C_{12-20}$ alkyl glucoside, caprylyl/capryl glucoside, cetearyl glucoside, coco-glucoside, ethyl glucoside and lauryl glucoside, decyl glucoside, or any combination thereof.
45. The composition according to embodiment 40, wherein the one or more sucrose esters include sucrose monooleate, sucrose monolaurate, sucrose monopalmitate, sucrose monostearate, sucrose trioleate, sucrose ricinoleate, sucrose tristearate, sucrose diglycerides, sucrose triacetate, or any combination thereof.
46. The composition according to embodiment 40, wherein the one or more ethoxylated alkyl phenols include ethoxylated nonyl phenol, ethoxylated octyl phenol, or any combination thereof.
47. The composition according to embodiment 40, wherein the one or more ethoxylated fatty acids include ethoxylated castor oil.
48. The composition according to embodiment 40, wherein the one or more ethoxylated fatty alcohols include ethoxylated ceto-oleyl alcohol, ethoxylated ceto-stearyl alcohol, ethoxylated decyl alcohol, ethoxylated dodecyl alcohol, ethoxylated tridecyl alcohol, or any combination thereof.
49. The composition according to embodiment 40, wherein the one or more poloxamers (polyethylene-polypropylene copolymers) include Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), or any combination thereof.
50. The composition according to embodiment 40, wherein the one or more linear secondary alcohol ethoxylates include TERGITOL™ 15-S-5, TERGITOL™ 15-S-7, TERGITOL™ 15-S-9, TERGITOL™ 15-S-12, TERGITOL™ 15-S-15, TERGITOL™ 15-S-20, TERGITOL™ 15-S-30, TERGITOL™ 15-S-40, or any combination thereof.
51. The composition according to embodiment 40, wherein the one or more polyoxyethylene glycol alkyl ethers include octaethylene glycol monododecyl ether, pentaethylene glycol monododecyl ether, BRIJ® 30, BRIJ® 35, or any combination thereof.
52. The composition according to embodiment 40, wherein the one or more polyoxyethylene glycol octylphenol ethers include polyoxyethylene (4-5) p-t-octyl phenol (TRITON® X-45), polyoxyethylene octyl phenyl ether (TRITON® X-100), or any combination thereof.
53. The composition according to embodiment 40, wherein the one or more polyoxyethylene glycol alkylphenol ethers include Nonoxynol-9.
54. The composition according to embodiment 40, wherein the one or more phenoxypolyethoxylethanols include nonylphenoxypolyethoxylethanol, octylphenoxypolyethoxylethanol (IGEPAL® CA-630 or NONIDET™ P-40), or any combination thereof.
55. The composition according to embodiment 40, wherein the one or more glucoside alkyl ethers include octyl glucopyranoside.
56. The composition according to embodiment 40, wherein the one or more maltoside alkyl ethers include dodecyl maltopyranoside.
57. The composition according to embodiment 40, wherein the one or more thioglucoside alkyl ethers include heptyl thioglucopyranoside.
58. The composition according to embodiment 40, wherein the one or more glycerol alkyl esters include glyceryl laurate.
59. The composition according to embodiment 40, wherein the one or more cocamide ethanolamines include cocamide monoethanolamine, cocamide diethanolamine, or any combination thereof.
60. The composition according to embodiment 22, wherein the one or more biosurfactants include one or more bio-based anionic surfactants, one or more bio-based nonionic surfactants, or any combination thereof.
61. The composition according to embodiment 60, wherein the one or more bio-based anionic surfactants include STEPONOL® AM 30-KE, an ammonium lauryl sulfate, and STEPONOL® EHS, a sodium 2-ethyl hexyl sulfate, or any combination thereof.
62. The composition according to embodiment 60, wherein the one or more bio-based nonionic surfactants include STEPOSOL® MET-10U, a metathesis-derived, nonionic surfactant that is an unsaturated, short chain amide.
63. The composition according to any one of embodiments 18-62, wherein the one or more surfactants are in an amount of aspects of, e.g., about 0.001%, about 0.005%, about 0.0075%, about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition, or at least 0.001%, at least 0.005%, at least 0.0075%, at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0% by weight of the composition, or at most 0.001%, at most 0.005%, at most 0.0075%, at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition, or about 0.001% to about 0.005%, about 0.001% to about 0.0075%, about 0.001% to about 0.01%, about 0.001% to about 0.025%, about 0.001% to about 0.05%, about 0.001% to about 0.075%, about 0.001% to about 0.1%, about 0.001% to about 0.25%, about 0.001% to about 0.75%, about 0.001% to about 1.0%, about 0.005% to about 0.0075%, about 0.005% to about 0.01%, about 0.005% to about 0.025%, about 0.005% to about 0.05%, about 0.005% to about 0.075%, about 0.005% to about 0.1%, about 0.005% to about 0.25%, about 0.005% to about 0.75%, about 0.005% to about 1.0%, about 0.01% to about 0.05%, about 0.01% to about 0.075%, about 0.01% to about 0.1%, about 0.01% to about 0.25%, about 0.01% to about 0.5%, about 0.01% to about 0.75%, about 0.01% to about 1.0%, about 0.01% to about 1.5%, about 0.01% to about 2.0%, about 0.01% to about 2.5%, about 0.05% to about 0.075%, about 0.05% to about 0.1%, about 0.05% to about 0.25%, about 0.05% to about 0.5%, about 0.05% to about 0.75%, about 0.05% to about 1.0%, about 0.05% to about 1.5%, about 0.05% to about 2.0%, about 0.05% to about 2.5%, about 0.1% to about 0.5%, about 0.1% to about 0.75%, about 0.1% to about 1.0%, about 0.1% to about 1.5%, about 0.1% to about 2.0%, about 0.1% to about 2.5%, about 0.1% to about 3.0%, about 0.1% to about 4.0%, about 0.1% to about 5.0%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.2% to about 3.0%, about 0.2% to about 4.0%, about 0.2% to about 5.0%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0%, about 5.0% to about 15.0%, about 6.0% to about 7.0%, about 6.0% to about 7.5%, about 6.0% to about 8.0%, about 6.0% to about 9.0%, about 6.0% to about 10.0%, about 6.0% to about 11.0%, about 6.0% to about 12.0%, about 6.0% to about 13.0%, about 6.0% to about 14.0% or about 6.0% to about 15.0% by weight of the composition.

63. A composition comprising, consisting essentially of, or consisting of one or more guanide-containing compounds and one or more alcohols.

64. The composition according to embodiment 63, wherein the one or more guanide-containing compounds comprise, consist essentially of, or consist of comprise, consist essentially of, or consist of a biguanide, a biguanide-containing compound, a biguanidine, a biguanidine-containing compound, a triguanide, a triguanide-containing compound, or any combination thereof.

65. The composition according to embodiment 64, wherein the one or more biguanide-containing compounds include a polyhexamethylene biguanide (PHMB), a polyaminopropyl biguanide (PAPB), a 1,1'-(1,6-Hexanediyl)bis{2-[N'-(2-ethylhexyl)carbamimidoyl]guanidine} (alexidine), a chlorhexidine, a chlorhexidine gluconate, or any combination thereof.

66. The composition according to any one of embodiments 63-65, wherein the one or more alcohols is methanol, ethanol, propanol, isopropanol, butanol, pentanol, and 1-hexadecanol.

67. The composition according to any one of embodiments 63-66, wherein the one or more guanide-containing compounds are in an amount of about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 6.5%, about 7.0%, about 7.5%, about 8.0%, about 8.5%, about 9.0%, about 9.5%, about 10.0%. about 11%, about 12%, about 13%, about 14%, about 15%, about 20%, about 25%, or about 30% by weight of the composition, or at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, at least 10.0%, at least 11%, at least 12%, at least 13%, at least 14%, at least 15%, at least 20%, at least 25%, or at least 30% by weight of the composition, or at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0%, at most 10.0%, at most 11%, at most 12%, at most 13%, at most 14%, at most 15%, at most 20%, at most 25%, or at most 30% by weight of the composition, or about 0.1% to about 0.5%, about 0.1% to about 0.75%, about 0.1% to about 1.0%, about 0.1% to about 1.5%, about 0.1% to about 2.0%, about 0.1% to about 2.5%, about 0.1% to about 3.0%, about 0.1% to about 3.5%, about 0.1% to about 4.0%, about 0.1% to about 4.5%, about 0.1% to about 5.0%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.2% to about 3.0%, about 0.2% to about 3.5%, about 0.2% to about 4.0%, about 0.2% to about 4.5%, about 0.2% to about 5.0%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 1.0% to about 15.0%, about 1.0% to about 20.0%, about 1.0% to about 25.0%, about 1.0% to about 30.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 2.0% to about 15.0%, about 2.0% to about 20.0%, about 2.0% to about 25.0%, about 2.0% to about 30.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0%, about 5.0% to about 15.0%, about 5.0% to about 20.0%, about 5.0% to about 25.0%, about 5.0% to about 30.0%, about 6.0% to about 7.0%, about 6.0% to about 7.5%, about 6.0% to about 8.0%, about 6.0% to about 9.0%, about 6.0% to about 10.0%, about 6.0% to about 11.0%, about 6.0% to about 12.0%, about 6.0% to about 13.0%, about 6.0% to about 14.0%, about 6.0% to about 15.0%, about 6.0% to about 20.0%, about 6.0% to about 25.0%, about 6.0% to about 30.0%, about 7.0% to about 8.0%, about 7.0% to about 9.0%, about 7.0% to about 10.0%, about 7.0% to about 11.0%, about 7.0% to about 12.0%, about 7.0% to about 13.0%, about 7.0% to about 14.0%, about 7.0% to about 15.0%, about 7.0% to about 20.0%, about 7.0% to about 25.0%, about 7.0% to about 30.0%, about 8.0% to about 9.0%, about 8.0% to about 10.0%, about 8.0% to about 11.0%, about 8.0% to about 12.0%, about 8.0% to about 13.0%, about 8.0% to about 14.0%, about 8.0% to about 15.0%, about 8.0% to about 20.0%, about 8.0% to about 25.0%, about 8.0% to about 30.0%, about 9.0% to about 10.0%, about 9.0% to about 11.0%, about 9.0% to about 12.0%, about 9.0% to about 13.0%, about 9.0% to about 14.0%, about 9.0% to about 15.0%, about 9.0% to about 20.0%, about 9.0% to about 25.0%, about 9.0% to about 30.0%, about 10.0% to about 11.0%, about 10.0% to about 12.0%, about 10.0% to about 13.0%, about 10.0% to about 14.0%, about 10.0% to about 15.0%, about 10.0% to about 20.0%, about 10.0% to about 25.0%, about 10.0% to about 30.0%, about 15.0% to about 20.0%, about 15.0% to about 25.0%, about 15.0% to about 30.0%, about 20.0% to about 25.0%, about 20.0% to about 30.0%, or about 20.0% to about 30.0%, by weight of the composition.

68. The composition according to any one of embodiments 63-67, wherein the one or more alcohols are in an amount of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99%, by weight of the composition, or at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%, by weight of the composition, or at most 5%, at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95%, at most 96%, at most 97%, at most 98%, or at most 99%, by weight of the composition, or about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 5% to about 95%, about 5% to about 97%, about 5% to about 99%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 10% to about 97%, about 10% to about 99%, about 20% to about 30%, about 20% to about 40%, about 20% to about 50%, about 20% to about 60%, about 20% to about 70%, about 20% to about 80%, about 20% to about 90%, about 20% to about 95%, about 20% to about 97%, about 20% to about 99%, about 30% to about 40%, about 30% to about 50%, about 30% to about 60%, about 30% to about 70%, about 30% to about 80%, about 30% to about 90%, about 30% to about 95%, about 30% to about 97%, about 30% to about 99%, about 35% to about 40%, about 35% to about 50%, about 35% to about 60%, about 35% to about 70%, about 35% to about 80%, about 35% to about 90%, about 35% to about 95%, about 35% to about 97%, about 35% to about 99%, about 40% to about 50%, about 40% to about 60%, about 40% to about 70%, about 40% to about 80%, about 40% to about 90%, about 40% to about 95%, about 40% to about 97%, about 40% to about 99%, about 45% to about 50%, about 45% to about 60%, about 45% to about 70%, about 45% to about 80%, about 45% to about 90%, about 45% to about 95%, about 45% to about 97%, about 45% to about 99%, about 50% to about 60%, about 50% to about 70%, about 50% to about 80%, about 50% to about 90%, about 50% to about 95%, about 50% to about 97%, about 50% to about 99%, about 60% to about 70%, about 60% to about 80%, about 60% to about 90%, about 60% to about 95%, about 60% to about 97%, about 60% to about 99%, about 70% to about 80%, about 70% to about 90%, about 70% to about 95%, about 70% to about 97%, about 70% to about 99%, about 80% to about 90%, about 80% to about 95%, about 80% to about 97%, about 80% to about 99%, about 90% to about 95%, about 90% to about 97%, about 90% to about 99%, by weight of the composition.

69. A composition comprising, consisting essentially of, or consisting of one or more guanide-containing compounds.

70. The composition according to embodiment 69, wherein the one or more guanide-containing compounds comprise, consist essentially of, or consist of comprise, consist essentially of, or consist of a biguanide, a biguanide-containing compound, a biguanidine, a biguanidine-containing compound, a triguanide, a triguanide-containing compound, or any combination thereof.

71. The composition according to embodiment 70, wherein the one or more biguanide-containing compounds include a polyhexamethylene biguanide (PHMB), a polyaminopropyl biguanide (PAPB), a 1,1'-(1,6-Hexanediyl)bis{2-[N'-(2-ethylhexyl)carbamimidoyl]guanidine} (alexidine), a chlorhexidine, a chlorhexidine gluconate, or any combination thereof.

72. The composition according to any one of embodiments 69-71, wherein the one or more alcohols is methanol, ethanol, propanol, isopropanol, butanol, pentanol, and 1-hexadecanol.

73. The composition according to any one of embodiments 69-72, wherein the one or more guanide-containing compounds are in an amount of about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 6.5%, about 7.0%, about 7.5%, about 8.0%, about 8.5%, about 9.0%, about 9.5%, about 10.0%. about 11%, about 12%, about 13%, about 14%, about 15%, about 20%, about 25%, or about 30% by weight of the composition, or at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, at least 10.0%, at least 11%, at least 12%, at least 13%, at least 14%, at least 15%, at least 20%, at least 25%, or at least 30% by weight of the composition, or at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0%, at most 10.0%, at most 11%, at most 12%, at most 13%, at most 14%, at most 15%, at most 20%, at most 25%, or at most 30% by weight of the composition, or about 0.1% to about 0.5%, about 0.1% to about 0.75%, about 0.1% to about 1.0%, about 0.1% to about 1.5%, about 0.1% to about 2.0%, about 0.1% to about 2.5%, about 0.1% to about 3.0%, about 0.1% to about 3.5%, about 0.1% to about 4.0%, about 0.1% to about 4.5%, about 0.1% to about 5.0%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.2% to about 3.0%, about 0.2% to about 3.5%, about 0.2% to about 4.0%, about 0.2% to about 4.5%, about 0.2% to about 5.0%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 1.0% to about 15.0%, about 1.0% to about 20.0%, about 1.0% to about 25.0%, about 1.0% to about 30.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 2.0% to about 15.0%, about 2.0% to about 20.0%, about 2.0% to about 25.0%, about 2.0% to about 30.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0%, about 5.0% to about 15.0%, about 5.0% to about 20.0%, about 5.0% to about 25.0%, about 5.0% to about 30.0%, about 6.0% to about 7.0%, about 6.0% to about 7.5%, about 6.0% to about 8.0%, about 6.0% to about 9.0%, about 6.0% to about 10.0%, about 6.0% to about 11.0%, about 6.0% to about 12.0%, about 6.0% to about 13.0%, about 6.0% to about 14.0%, about 6.0% to about 15.0%, about 6.0% to about 20.0%, about 6.0% to about 25.0%, about 6.0% to about 30.0%, about 7.0% to about 8.0%, about 7.0% to about 9.0%, about 7.0% to about 10.0%, about 7.0% to about 11.0%, about 7.0% to about 12.0%, about 7.0% to about 13.0%, about 7.0% to about 14.0%, about 7.0% to about 15.0%, about 7.0% to about 20.0%, about 7.0% to about 25.0%, about 7.0% to about 30.0%, about 8.0% to about 9.0%, about 8.0% to about 10.0%, about 8.0% to about 11.0%, about 8.0% to about 12.0%, about 8.0% to about 13.0%, about 8.0% to about 14.0%, about 8.0% to about 15.0%, about 8.0% to about 20.0%, about 8.0% to about 25.0%, about 8.0% to about 30.0%, about 9.0% to about 10.0%, about 9.0% to about 11.0%, about 9.0% to about 12.0%, about 9.0% to about 13.0%, about 9.0% to about 14.0%, about 9.0% to about 15.0%, about 9.0% to about 20.0%, about 9.0% to about 25.0%, about 9.0% to about 30.0%, about 10.0% to about 11.0%, about 10.0% to about 12.0%, about 10.0% to about 13.0%, about 10.0% to about 14.0%, about 10.0% to about 15.0%, about 10.0% to about 20.0%, about 10.0% to about 25.0%, about 10.0% to about 30.0%, about 15.0% to about 20.0%, about 15.0% to about 25.0%, about 15.0% to about 30.0%, about 20.0% to about 25.0%, about 20.0% to about 30.0%, or about 20.0% to about 30.0%, by weight of the composition.

74. The composition according to any one of embodiments 1-73, further comprising, consisting essentially of, or consisting of one or more carriers.

75. The composition according to embodiment 74, wherein the one or more carrier includes an aqueous carrier, a semi-solid carrier, a solid carrier, or any combination thereof.

76. The composition according to embodiment 74 or 75, wherein the one or more carriers includes water, a vegetable oil, a mineral oil, an ester oil, an ether, one or more alcohols, a fatty alcohol, an isoparaffin, a hydrocarbon oil, a polyol, a wax, or any combination thereof.

77. The composition according to embodiment 76, wherein the ester oil includes octal palmitate, isopropyl myristate or isopropyl palmitate.

78. The composition according to embodiment 76, wherein the ether includes dicapryl ether or dimethyl isosorbide.

79. The composition according to embodiment 76, wherein the alcohol includes ethanol or isopropanol.

80. The composition according to embodiment 76, wherein the fatty alcohol includes cetyl alcohol, cetearyl alcohol, stearyl alcohol or behenyl alcohol.

81. The composition according to embodiment 76, wherein the isoparaffin includes isooctane, isododecane (IDD) or isohexadecane.

82. The composition according to embodiment 76, wherein the hydrocarbon oil includes mineral oil, petrolatum, isoeicosane or a polyolefin.

83. The composition according to embodiment 76, wherein the polyol includes propylene glycol, glycerin, butylene glycol, pentylene glycol, hexylene glycol, or caprylyl glycol.

84. The composition according to embodiment 76, wherein the wax includes beeswax, carnauba, ozokerite, microcrystalline wax, polyethylene wax, or a botanical wax.

85. The composition according to any one of embodiments 74-84, wherein the one or more carriers are in an amount of at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% by weight of the composition or at most 25%, at most 30%, at most 35%, at most 40%, at most 45%, at most 50%, at most 55%, at most 60%, at most 65%, at most 70%, at most 75%, at most 80%, at most 85%, at most 90%, at most 95%, at most 96%, at most 97%, at most 98% or at most 99% by weight of the composition or about 25% to about 50%, about 25% to about 75%, about 25% to about 90%, about 25% to about 95%, about 25% to about 96%, about 25% to about 97%, about 25% to about 98%, about 25% to about 99%, about 50% to about 75%, about 50% to about 90%, about 50% to about 95%, about 50% to about 96%, about 50% to about 97%, about 50% to about 98%, about 50% to about 99%, about 75% to about 80%, about 75% to about 85%, about 75% to about 90%, about 75% to about 95%, about 75% to about 96%, about 75% to about 97%, about 75% to about 98%, about 75% to about 99%, about 80% to about 85%, about 80% to about 90%, about 80% to about 95%, about 80% to about 96%, about 80% to about 97%, about 80% to about 98%, about 80% to about 99%, about 85% to about 90%, about 85% to about 95%, about 85% to about 96%, about 85% to about 97%, about 85% to about 98%, about 85% to about 99%, about 90% to about 95%, about 90% to about 96%, about 90% to about 97%, about 90% to about 98%, about 90% to about 99%, or about 95% to about 99%, by weight of the composition.

86. The composition according to any one of embodiments 1-85, further comprising, consisting essentially of, or consisting of one or more additional ingredients.
87. The composition according to embodiment 86, wherein the one or more additional ingredient includes a preservative, a chelating agent, or any combination thereof.
88. The composition according to any one of embodiments 1-87, having a pH of about 2 to about 5, about 2 to about 5.5, about 2 to about 6, about 2 to about 6.5, about 2 to about 7, about 2 to about 7.5, about 2 to about 8, about 2 to about 8.5, about 2 to about 9, about 2.5 to about 5, about 2.5 to about 5.5, about 2.5 to about 6, about 2.5 to about 6.5, about 2.5 to about 7, about 2.5 to about 7.5, about 2.5 to about 8, about 2.5 to about 8.5, about 2.5 to about 9, about 3 to about 5, about 3 to about 5.5, about 3 to about 6, about 3 to about 6.5, about 3 to about 7, about 3 to about 7.5, about 3 to about 8, about 3 to about 8.5, about 3 to about 9, about 3.5 to about 5, about 3.5 to about 5.5, about 3.5 to about 6, about 3.5 to about 6.5, about 3.5 to about 7, about 3.5 to about 7.5, about 3.5 to about 8, about 3.5 to about 8.5, about 3.5 to about 9, about 4 to about 5, about 4 to about 5.5, about 4 to about 6, about 4 to about 6.5, about 4 to about 7, about 4 to about 7.5, about 4 to about 8, about 4 to about 8.5, about 4 to about 9, about 4.5 to about 5, about 4.5 to about 5.5, about 4.5 to about 6, about 4.5 to about 6.5, about 4.5 to about 7, about 4.5 to about 7.5, about 4.5 to about 8, about 4.5 to about 8.5, about 4.5 to about 9, about 5 to about 5.5, about 5 to about 6, about 5 to about 6.5, about 5 to about 7, about 5 to about 7.5, about 5 to about 8, about 5 to about 8.5, about 5 to about 9, about 5.5 to about 6, about 5.5 to about 6.5, about 5.5 to about 7, about 5.5 to about 7.5, about 5.5 to about 8, about 5.5 to about 8.5, about 5.5 to about 9, about 6 to about 6.5, about 6 to about 7, about 6 to about 7.5, about 6 to about 8, about 6 to about 8.5, about 6 to about 9, about 6.5 to about 7, about 6.5 to about 7.5, about 6.5 to about 8, about 6.5 to about 8.5, about 6.5 to about 9, about 7 to about 7.5, about 7 to about 8, about 7 to about 8.5, about 7 to about 9, about 7.5 to about 8, about 7.5 to about 8.5, about 7.5 to about 9, about 8 to about 8.5, about 8 to about 9, or about 8.5 to about 9.
89. The composition according to any one of embodiments 1-87, having a pH of about 6 to about 8, about 6.7 to about 7.7, about 6.8 to about 7.6, about 6.9 to about 7.5, about 7.0 to about 7.4, about 7.1 to about 7.3, or about 7.2.
90. The composition according to any one of embodiments 1-87, having a pH of about 5.0 to about 6.5, about 5.2 to about 6.2, about 5.3 to about 6.1, about 5.4 to about 6.0, about 5.5 to about 5.9, about 5.6 to about 5.8, or about 5.7.
91. The composition according to any one of embodiments 1-87, having a pH of about 5.3 to about 6.8, about 5.5 to about 6.5, about 5.6 to about 6.4, about 5.7 to about 6.3, about 5.8 to about 6.2, about 5.9 to about 6.1, or about 6.0.
92. The composition according to any one of embodiments 1-91, having a stability of about 1 day, about 2 days, 3 days, 4 days, 5 days, 6, days, 7 days, 8 days, 9 days, 10 days, 11 days, 12 days, 13 days, 14 days or 15 days or at least 1 day, at least 2 days, at least 3 days, at least 4 days, at least 5 days, at least 6, days, at least 7 days, at least 8 days, at least 9 days, at least 10 days, at least 11 days, at least 12 days, at least 13 days, at least 14 days or at least 15 days or at most 1 day, at most 2 days, at most 3 days, at most 4 days, at most 5 days, at most 6 days, at most 7 days, at most 8 days, at most 9 days, at most 10 days, at most 11 days, at most 12 days, at most 13 days, at most 14 days or at most 15 days or about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 1 day to about 12 days, about 1 day to about 13 days, about 1 day to about 14 days, about 1 day to about 15 days, about 2 days to about 3 days, about 2 days to about 4 days, about 2 days to about 5 days, about 2 days to about 6 days, about 2 days to about 7 days, about 2 days to about 8 days, about 2 days to about 9 days, about 2 days to about 10 days, about 2 days to about 11 days, about 2 days to about 12 days, about 2 days to about 13 days, about 2 days to about 14 days, about 2 days to about 15 days, about 3 days to about 4 days, about 3 days to about 5 days, about 3 days to about 6 days, about 3 days to about 7 days, about 3 days to about 8 days, about 3 days to about 9 days, about 3 days to about 10 days, about 3 days to about 11 days, about 3 days to about 12 days, about 3 days to about 13 days, about 3 days to about 14 days, about 3 days to about 15 days, about 4 days to about 5 days, about 4 days to about 6 days, about 4 days to about 7 days, about 4 days to about 8 days, about 4 days to about 9 days, about 4 days to about 10 days, about 4 days to about 11 days, about 4 days to about 12 days, about 4 days to about 13 days, about 4 days to about 14 days, about 4 days to about 15 days, about 5 days to about 6 days, about 5 days to about 7 days, about 5 days to about 8 days, about 5 days to about 9 days, about 5 days to about 10 days, about 5 days to about 11 days, about 5 days to about 12 days, about 5 days to about 13 days, about 5 days to about 14 days, about 5 days to about 15 days, about 6 days to about 7 days, about 6 days to about 8 days, about 6 days to about 9 days, about 6 days to about 10 days, about 6 days to about 11 days, about 6 days to about 12 days, about 6 days to about 13 days, about 6 days to about 14 days, about 6 days to about 15 days, about 7 days to about 8 days, about 7 days to about 9 days, about 7 days to about 10 days, about 7 days to about 11 days, about 7 days to about 12 days, about 7 days to about 13 days, about 7 days to about 14 days, about 7 days to about 15 days, about 8 days to about 9 days, about 8 days to about 10 days, about 8 days to about 11 days, about 8 days to about 12 days, about 8 days to about 13 days, about 8 days to about 14 days, about 8 days to about 15 days, about 9 days to about 10 days, about 9 days to about 11 days, about 9 days to about 12 days, about 9 days to about 13 days, about 9 days to about 14 days, about 9 days to about 15 days, about 10 days to about 11 days, about 10 days to about 12 days, about 10 days to about 13 days, about 10 days to about 14 days, about 10 days to about 15 days, about 11 days to about 12 days, about 11 days to about 13 days, about 11 days to about 14 days, about 11 days to about 15 days, about 12 days to about 13 days, about 12 days to about 14 days, about 12 days to about 15 days, about 13 days to about 14 days, about 13 days to about 15 days, or about 14 days to about 15 days.
93. The composition according to any one of embodiments 1-91, having a stability of about 1 week, about 2 weeks, 3 weeks, 4 weeks, 5 weeks, 6, weeks, 7 weeks, 8 weeks, 9 weeks, 10 weeks, 11 weeks, 12 weeks, 13 weeks, 14 weeks or 15 weeks or at least 1 week, at least 2 weeks, at least 3 weeks, at least 4 weeks, at least 5 weeks, at least 6, weeks, at least 7 weeks, at least 8 weeks, at least 9 weeks, at least 10 weeks, at least 11 weeks, at least 12 weeks, at least 13 weeks, at least 14 weeks or at least 15 weeks or at most 1 week, at most 2 weeks, at most 3 weeks, at most 4 weeks, at most 5 weeks, at most 6, weeks, at most 7 weeks, at most 8 weeks, at most 9 weeks, at most 10 weeks, at most 11 weeks, at most 12 weeks, at most 13 weeks, at most 14 weeks or at most 15 weeks or about 1 week to about 2 weeks, about 1 week to about 3 weeks, about 1 week to about 4 weeks, about 1 week to about 5 weeks, about 1 week to about 6 weeks, about 1 week to about 7 weeks, about 1 week to about 8 weeks, about 1 week to about 9 weeks, about 1 week to about 10 weeks, about 1 week to about 11 weeks, about 1 week to about 12 weeks, about 1 week to about 13 weeks, about 1 week to about 14 weeks, about 1 week to about 15 weeks, about 2 weeks to about 3 weeks, about 2 weeks to about 4 weeks, about 2 weeks to about 5 weeks, about 2 weeks to about 6 weeks, about 2 weeks to about 7 weeks, about 2 weeks to about 8 weeks, about 2 weeks to about 9 weeks, about 2 weeks to about 10 weeks, about 2 weeks to about 11 weeks, about 2 weeks to about 12 weeks, about 2 weeks to about 13 weeks, about 2 weeks to about 14 weeks, about 2 weeks to about 15 weeks, about 3 weeks to about 4 weeks, about 3 weeks to about 5 weeks, about 3 weeks to about 6 weeks, about 3 weeks to about 7 weeks, about 3 weeks to about 8 weeks, about 3 weeks to about 9 weeks, about 3 weeks to about 10 weeks, about 3 weeks to about 11 weeks, about 3 weeks to about 12 weeks, about 3 weeks to about 13 weeks, about 3 weeks to about 14 weeks, about 3 weeks to about 15 weeks, about 4 weeks to about 5 weeks, about 4 weeks to about 6 weeks, about 4 weeks to about 7 weeks, about 4 weeks to about 8 weeks, about 4 weeks to about 9 weeks, about 4 weeks to about 10 weeks, about 4 weeks to about 11 weeks, about 4 weeks to about 12 weeks, about 4 weeks to about 13 weeks, about 4 weeks to about 14 weeks, about 4 weeks to about 15 weeks, about 5 weeks to about 6 weeks, about 5 weeks to about 7 weeks, about 5 weeks to about 8 weeks, about 5 weeks to about 9 weeks, about 5 weeks to about 10 weeks, about 5 weeks to about 11 weeks, about 5 weeks to about 12 weeks, about 5 weeks to about 13 weeks, about 5 weeks to about 14 weeks, about 5 weeks to about 15 weeks, about 6 weeks to about 7 weeks, about 6 weeks to about 8 weeks, about 6 weeks to about 9 weeks, about 6 weeks to about 10 weeks, about 6 weeks to about 11 weeks, about 6 weeks to about 12 weeks, about 6 weeks to about 13 weeks, about 6 weeks to about 14 weeks, about 6 weeks to about 15 weeks, about 7 weeks to about 8 weeks, about 7 weeks to about 9 weeks, about 7 weeks to about 10 weeks, about 7 weeks to about 11 weeks, about 7 weeks to about 12 weeks, about 7 weeks to about 13 weeks, about 7 weeks to about 14 weeks, about 7 weeks to about 15 weeks, about 8 weeks to about 9 weeks, about 8 weeks to about 10 weeks, about 8 weeks to about 11 weeks, about 8 weeks to about 12 weeks, about 8 weeks to about 13 weeks, about 8 weeks to about 14 weeks, about 8 weeks to about 15 weeks, about 9 weeks to about 10 weeks, about 9 weeks to about 11 weeks, about 9 weeks to about 12 weeks, about 9 weeks to about 13 weeks, about 9 weeks to about 14 weeks, about 9 weeks to about 15 weeks, about 10 weeks to about 11 weeks, about 10 weeks to about 12 weeks, about 10 weeks to about 13 weeks, about 10 weeks to about 14 weeks, about 10 weeks to about 15 weeks, about 11 weeks to about 12 weeks, about 11 weeks to about 13 weeks, about 11 weeks to about 14 weeks, about 11 weeks to about 15 weeks, about 12 weeks to about 13 weeks, about 12 weeks to about 14 weeks, about 12 weeks to about 15 weeks, about 13 weeks to about 14 weeks, about 13 weeks to about 15 weeks, or about 14 weeks to about 15 weeks.

94. The composition according to any one of embodiments 1-91, having a stability of about 1 month, about 2 months, 3 months, 4 months, 5 months, 6, months, 7 months, 8 months, 9 months, 10 months, 11 months, 12 months, 13 months, 14 months or 15 months or at least 1 month, at least 2 months, at least 3 months, at least 4 months, at least 5 months, at least 6, months, at least 7 months, at least 8 months, at least 9 months, at least 10 months, at least 11 months, at least 12 months, at least 13 months, at least 14 months or at least 15 months or at most 1 month, at most 2 months, at most 3 months, at most 4 months, at most 5 months, at most 6, months, at most 7 months, at most 8 months, at most 9 months, at most 10 months, at most 11 months, at most 12 months, at most 13 months, at most 14 months or at most 15 months or about 1 month to about 2 months, about 1 month to about 3 months, about 1 month to about 4 months, about 1 month to about 5 months, about 1 month to about 6 months, about 1 month to about 7 months, about 1 month to about 8 months, about 1 month to about 9 months, about 1 month to about 10 months, about 1 month to about 11 months, about 1 month to about 12 months, about 1 month to about 13 months, about 1 month to about 14 months, about 1 month to about 15 months, about 2 months to about 3 months, about 2 months to about 4 months, about 2 months to about 5 months, about 2 months to about 6 months, about 2 months to about 7 months, about 2 months to about 8 months, about 2 months to about 9 months, about 2 months to about 10 months, about 2 months to about 11 months, about 2 months to about 12 months, about 2 months to about 13 months, about 2 months to about 14 months, about 2 months to about 15 months, about 3 months to about 4 months, about 3 months to about 5 months, about 3 months to about 6 months, about 3 months to about 7 months, about 3 months to about 8 months, about 3 months to about 9 months, about 3 months to about 10 months, about 3 months to about 11 months, about 3 months to about 12 months, about 3 months to about 13 months, about 3 months to about 14 months, about 3 months to about 15 months, about 4 months to about 5 months, about 4 months to about 6 months, about 4 months to about 7 months, about 4 months to about 8 months, about 4 months to about 9 months, about 4 months to about 10 months, about 4 months to about 11 months, about 4 months to about 12 months, about 4 months to about 13 months, about 4 months to about 14 months, about 4 months to about 15 months, about 5 months to about 6 months, about 5 months to about 7 months, about 5 months to about 8 months, about 5 months to about 9 months, about 5 months to about 10 months, about 5 months to about 11 months, about 5 months to about 12 months, about 5 months to about 13 months, about 5 months to about 14 months, about 5 months to about 15 months, about 6 months to about 7 months, about 6 months to about 8 months, about 6 months to about 9 months, about 6 months to about 10 months, about 6 months to about 11 months, about 6 months to about 12 months, about 6 months to about 13 months, about 6 months to about 14 months, about 6 months to about 15 months, about 7 months to about 8 months, about 7 months to about 9 months, about 7 months to about 10 months, about 7 months to about 11 months, about 7 months to about 12 months, about 7 months to about 13 months, about 7 months to about 14 months, about 7 months to about 15 months, about 8 months to about 9 months, about 8 months to about 10 months, about 8 months to about 11 months, about 8 months to about 12 months, about 8 months to about 13 months, about 8 months to about 14 months, about 8 months to about 15 months, about 9 months to about 10 months, about 9 months to about 11 months, about 9 months to about 12 months, about 9 months to about 13 months, about 9 months to about 14 months, about 9 months to about 15 months, about 10 months to about 11 months, about 10 months to about 12 months, about 10 months to about 13 months, about 10 months to about 14 months, about 10 months to about 15 months, about 11 months to about 12 months, about 11 months to about 13 months, about 11 months to about 14 months, about 11 months to about 15 months, about 12 months to about 13 months, about 12 months to about 14 months, about 12 months to about 15 months, about 13 months to about 14 months, about 13 months to about 15 months, or about 14 months to about 15 months.

95. The composition according to any one of embodiments 1-91, having a stability of about 1 year, about 2 years, about 3 years, about 4 years, or about 5 years or at least 1 year, at least 2 years, at least 3 years, at least 4 years, or at least 5 years or at most 1 year, at most 2 years, at most 3 years, at most 4 years, or at most 5 years or about 1 year to about 2 years, about 1 year to about 3 years, about 1 year to about 4 years, about 1 year to about 5 years, about 2 years to about 3 years, about 2 years to about 4 years, about 2 years to about 5 years, about 3 years to about 4 years, about 3 years to about 5 years, or about 4 years to about 5 years.

96. The composition according to any one of embodiments 1-95, wherein the composition does not comprise, consist essentially of, or consist of ozone.

97. The composition according to any one of embodiments 1-96, wherein the composition does not comprise, consist essentially of, or consist of hydrogen peroxide.

98. The composition according to any one of embodiments 1-97, wherein the composition does not comprise, consist essentially of, or consist of hypochlorous acid or free available chlorine.

99. The composition according to any one of embodiments 1-98, wherein the composition does not comprise, consist essentially of, or consist of a surfactant.

100. The composition according to any one of embodiments 1-99, wherein the composition does not comprise, consist essentially of, or consist of a surfactant.

101. The composition according to any one of embodiments 1-100, wherein the composition does not comprise, consist essentially of, or consist of a guanide-containing compound.

102. The composition according to any one of embodiments 1-101, wherein the composition does not comprise, consist essentially of, or consist of an aldehyde-containing compounds.

103. The composition according to any one of embodiments 1-102, formulated as a single phase formulation or a biphasic formulation.

104. The composition according to any one of embodiments 1-103, formulated as a liquid composition, a colloidal composition, a semi-solid composition, or a solid composition.

105. The composition according to any one of embodiments 1-104, formulated as a liquid aerosol, a foam, an emulsion, a gel, a sol, or a solid sol.

106. The composition according to any one of embodiments 1-105, formulated as a spray, a liquid aerosol, a wash, a lotion, a cream, a soap, a dry powder, a vapor or a suspension.

107. A kit comprising, consisting essentially of, or consisting of a composition as defined in any one of embodiments 1-106.

108. The kit according to Embodiment 107, further comprising, consisting essentially of, or consisting of one or more delivery or application systems, and/or instructions, and/or a container.

109. A kit comprising, consisting essentially of, or consisting of a first component including hypochlorous acid or free available chlorine and a second component including one or more disinfectants.

110. A kit comprising, consisting essentially of, or consisting of a first component including one or more alcohols and a second component including one or more disinfectants.

111. A kit comprising, consisting essentially of, or consisting of a first component including isopropyl alcohol and a second component including polyhexamethylene biguanide.

112. The kit according to any one of Embodiments 109-111, further comprising, consisting essentially of, or consisting of a third component including one or more cationic surfactants, and/or a fourth component including a rinse solution and/or one or more delivery or application systems, and/or instructions, and/or a container.

113. The kit according to embodiment 109 or 112, wherein the hypochlorous acid or free available chlorine is in an amount of about 0.00005%, about 0.00006%, about 0.00007%, about 0.000075%, about 0.00008%, about 0.00009%, about 0.0001%, about 0.0005%, about 0.001%, about 0.0015%, about 0.002%, about 0.0025%, about 0.003%, about 0.0035%, about 0.004%, about 0.0045%, about 0.005%, about 0.0055%, about 0.006%, about 0.007%, about 0.0075%, about 0.008%, about 0.009%, about 0.01%, about 0.02%, about 0.03%, about 0.04%, about 0.05%, about 0.06%, about 0.07%, about 0.075%, about 0.08%, about 0.09%, about 0.10%, about 0.11%, about 0.12%, about 0.13%, about 0.14%, or about 0.15% by weight of the composition or at least 0.00005%, at least 0.00006%, at least 0.00007%, at least 0.000075%, at least 0.00008%, at least 0.00009%, at least 0.0001%, at least 0.0005%, at least 0.001%, at least 0.0015%, at least 0.002%, at least 0.0025%, at least 0.003%, at least 0.0035%, at least 0.004%, at least 0.0045%, at least 0.005%, at least 0.0055%, at least 0.006%, at least 0.007%, at least 0.0075%, at least 0.008%, at least 0.009%, at least 0.01%, at least 0.02%, at least 0.03%, at least 0.04%, at least 0.05%, at least 0.06%, at least 0.07%, at least 0.075%, at least 0.08%, at least 0.09%, at least 0.10%, at least 0.11%, at least 0.12%, at least 0.13%, at least 0.14%, or at least 0.15% by weight of the composition or at most 0.00005%, at most 0.00006%, at most 0.00007%, at most 0.000075%, at most 0.00008%, at most 0.00009%, at most 0.0001%, at most 0.0005%, at most 0.001%, at most 0.0015%, at most 0.002%, at most 0.0025%, at most 0.003%, at most 0.0035%, at most 0.004%, at most 0.0045%, at most 0.005%, at most 0.0055%, at most 0.006%, at most 0.007%, at most 0.0075%, at most 0.008%, at most 0.009%, at most 0.01%, at most 0.02%, at most 0.03%, at most 0.04%, at most 0.05%, at most 0.06%, at most 0.07%, at most 0.075%, at most 0.08%, at most 0.09%, at most 0.10%, at most 0.11%, at most 0.12%, at most 0.13%, at most 0.14%, or at most 0.15% by weight of the composition or about 0.00075% to about 0.002%, about 0.00075% to about 0.003%, about 0.00075% to about 0.004%, about 0.00075% to about 0.005%, about 0.00075% to about 0.006%, about 0.00075% to about 0.007%, about 0.00075% to about 0.008%, about 0.00075% to about 0.009%, about 0.00075% to about 0.01%, about 0.001% to about 0.002%, about 0.001% to about 0.003%, about 0.001% to about 0.004%, about 0.001% to about 0.005%, about 0.001% to about 0.006%, about 0.001% to about 0.007%, about 0.001% to about 0.008%, about 0.001% to about 0.009%, about 0.001% to about 0.01%, about 0.002% to about 0.003%, about 0.002% to about 0.004%, about 0.002% to about 0.005%, about 0.002% to about 0.006%, about 0.002% to about 0.007%, about 0.002% to about 0.008%, about 0.002% to about 0.009%, about 0.002% to about 0.01% by weight of the composition 114. The kit according to embodiment 109 or 112, wherein the hypochlorous acid or free available chlorine is in an amount of 0.05 ppm, 0.10 ppm, 0.15 ppm, 0.20 ppm, 0.25 ppm, 0.30 ppm, 0.35 ppm, 0.40 ppm, 0.45 ppm, 0.50 ppm, 0.55 ppm, 0.60 ppm, 0.65 ppm, 0.70 ppm, 0.75 ppm, 0.80 ppm, 0.85 ppm, 0.90 ppm, 0.95 ppm, 1 ppm, 5 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, 1,000 ppm, 1,025 ppm, 1,050 ppm, 1075 ppm, 1,100 ppm, 1,125 ppm, 1,150 ppm, 1,175 ppm, 1,200 ppm, 1,225 ppm, 1,250 ppm, 1,275 ppm, 1,300 ppm, 1,325 ppm, 1,350 ppm, 1,375 ppm, 1,400 ppm, 1,425 ppm, 1,450 ppm, 1,475 ppm, or 1,500 ppm or at least 0.05 ppm, at least 0.10 ppm, at least 0.20 ppm, at least 0.30 ppm, at least 0.40 ppm, at least 0.50 ppm, at least 0.60 ppm, at least 0.70 ppm, at least 0.80 ppm, at least 0.90 ppm, at least 1 ppm, at least 10 ppm, at least 20 ppm, at least 30 ppm, at least 40 ppm, at least 50 ppm, at least 60 ppm, at least 70 ppm, at least 80 ppm, at least 90 ppm, at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, at least 1,000 ppm, at least 1,025 ppm, at least 1,050 ppm, at least 1075 ppm, at least 1,100 ppm, at least 1,125 ppm, at least 1,150 ppm, at least 1,175 ppm, at least 1,200 ppm, at least 1,225 ppm, at least 1,250 ppm, at least 1,275 ppm, at least 1,300 ppm, at least 1,325 ppm, at least 1,350 ppm, at least 1,375 ppm, at least 1,400 ppm, at least 1,425 ppm, at least 1,450 ppm, at least 1,475 ppm, or at least 1,500 ppm or at most 0.05 ppm, at most 0.10 ppm, at most 0.20 ppm, at most 0.30 ppm, at most 0.40 ppm, at most 0.50 ppm, at most 0.60 ppm, at most 0.70 ppm, at most 0.80 ppm, at most 0.90 ppm, at most 1 ppm, at most 10 ppm, at most 20 ppm, at most 30 ppm, at most 40 ppm, at most 50 ppm, at most 60 ppm, at most 70 ppm, at most 80 ppm, at most 90 ppm, at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, at most 1,000 ppm, at most 1,025 ppm, at most 1,050 ppm, at most 1075 ppm, at most 1,100 ppm, at most 1,125 ppm, at most 1,150 ppm, at most 1,175 ppm, at most 1,200 ppm, at most 1,225 ppm, at most 1,250 ppm, at most 1,275 ppm, at most 1,300 ppm, at most 1,325 ppm, at most 1,350 ppm, at most 1,375 ppm, at most 1,400 ppm, at most 1,425 ppm, at most 1,450 ppm, at most 1,475 ppm, or at most 1,500 ppm or about 0.5 ppm to about 20 ppm, about 0.5 ppm to about 25 ppm, about 0.5 ppm to about 30 ppm, about 0.5 ppm to about 35 ppm, about 0.5 ppm to about 40 ppm, about 0.5 ppm to about 45 ppm, about 0.5 ppm to about 50 ppm, about 0.5 ppm to about 55 ppm, about 0.5 ppm to about 60 ppm, about 0.5 ppm to about 65 ppm, about 0.5 ppm to about 70 ppm, about 0.5 ppm to about 75 ppm, about 0.5 ppm to about 80 ppm, about 0.5 ppm to about 85 ppm, about 0.5 ppm to about 90 ppm, about 0.5 ppm to about 95 ppm, about 0.5 ppm to about 100 ppm, about 0.75 ppm to about 20 ppm, about 0.75 ppm to about 25 ppm, about 0.75 ppm to about 30 ppm, about 0.75 ppm to about 35 ppm, about 0.75 ppm to about 40 ppm, about 0.75 ppm to about 45 ppm, about 0.75 ppm to about 50 ppm, about 0.75 ppm to about 55 ppm, about 0.75 ppm to about 60 ppm, about 0.75 ppm to about 65 ppm, about 0.75 ppm to about 70 ppm, about 0.75 ppm to about 75 ppm, about 0.75 ppm to about 80 ppm, about 0.75 ppm to about 85 ppm, about 0.75 ppm to about 90 ppm, about 0.75 ppm to about 95 ppm, about 0.75 ppm to about 100 ppm, about 1 ppm to about 20 ppm, about 1 ppm to about 25 ppm, about 1 ppm to about 30 ppm, about 1 ppm to about 35 ppm, about 1 ppm to about 40 ppm, about 1 ppm to about 45 ppm, about 1 ppm to about 50 ppm, about 1 ppm to about 55 ppm, about 1 ppm to about 60 ppm, about 1 ppm to about 65 ppm, about 1 ppm to about 70 ppm, about 1 ppm to about 75 ppm, about 1 ppm to about 80 ppm, about 1 ppm to about 85 ppm, about 1 ppm to about 90 ppm, about 1 ppm to about 95 ppm, about 1 ppm to about 100 ppm, about 5 ppm to about 20 ppm, about 5 ppm to about 25 ppm, about 5 ppm to about 30 ppm, about 5 ppm to about 35 ppm, about 5 ppm to about 40 ppm, about 5 ppm to about 45 ppm, about 5 ppm to about 50 ppm, about 5 ppm to about 55 ppm, about 5 ppm to about 60 ppm, about 5 ppm to about 65 ppm, about 5 ppm to about 70 ppm, about 5 ppm to about 75 ppm, about 5 ppm to about 80 ppm, about 5 ppm to about 85 ppm, about 5 ppm to about 90 ppm, about 5 ppm to about 95 ppm, about 5 ppm to about 100 ppm, about 10 ppm to about 20 ppm, about 10 ppm to about 25 ppm, about 10 ppm to about 30 ppm, about 10 ppm to about 35 ppm, about 10 ppm to about 40 ppm, about 10 ppm to about 45 ppm, about 10 ppm to about 50 ppm, about 10 ppm to about 55 ppm, about 10 ppm to about 60 ppm, about 10 ppm to about 65 ppm, about 10 ppm to about 70 ppm, about 10 ppm to about 75 ppm, about 10 ppm to about 80 ppm, about 10 ppm to about 85 ppm, about 10 ppm to about 90 ppm, about 10 ppm to about 95 ppm, or about 10 ppm to about 100 ppm or about 1 ppm to about 25 ppm, about 1 ppm to about 50 ppm, about 1 ppm to about 75 ppm, about 1 ppm to about 100 ppm, about 1 ppm to about 125 ppm, about 1 ppm to about 150 ppm, about 1 ppm to about 175 ppm, about 1 ppm to about 200 ppm, about 1 ppm to about 225 ppm, about 1 ppm to about 250 ppm, about 1 ppm to about 275 ppm, about 1 ppm to about 300 ppm, about 1 ppm to about 325 ppm, about 1 ppm to about 350 ppm, about 1 ppm to about 375 ppm, about 1 ppm to about 400 ppm, about 10 ppm to about 25 ppm, about 10 ppm to about 50 ppm, about 10 ppm to about 75 ppm, about 10 ppm to about 100 ppm, about 10 ppm to about 125 ppm, about 10 ppm to about 150 ppm, about 10 ppm to about 175 ppm, about 10 ppm to about 200 ppm, about 10 ppm to about 225 ppm, about 10 ppm to about 250 ppm, about 10 ppm to about 275 ppm, about 10 ppm to about 300 ppm, about 10 ppm to about 325 ppm, about 10 ppm to about 350 ppm, about 10 ppm to about 375 ppm, about 10 ppm to about 400 ppm, about 25 ppm to about 50 ppm, about 25 ppm to about 75 ppm, about 25 ppm to about 100 ppm, about 25 ppm to about 125 ppm, about 25 ppm to about 150 ppm, about 25 ppm to about 175 ppm, about 25 ppm to about 200 ppm, about 25 ppm to about 225 ppm, about 25 ppm to about 250 ppm, about 25 ppm to about 275 ppm, about 25 ppm to about 300 ppm, about 25 ppm to about 325 ppm, about 25 ppm to about 350 ppm, about 25 ppm to about 375 ppm, about 25 ppm to about 400 ppm, about 50 ppm to about 75 ppm, about 50 ppm to about 100 ppm, about 50 ppm to about 125 ppm, about 50 ppm to about 150 ppm, about 50 ppm to about 175 ppm, about 50 ppm to about 200 ppm, about 50 ppm to about 225 ppm, about 50 ppm to about 250 ppm, about 50 ppm to about 275 ppm, about 50 ppm to about 300 ppm, about 50 ppm to about 325 ppm, about 50 ppm to about 350 ppm, about 50 ppm to about 375 ppm, about 50 ppm to about 400 ppm, about 75 ppm to about 100 ppm, about 75 ppm to about 125 ppm, about 75 ppm to about 150 ppm, about 75 ppm to about 175 ppm, about 75 ppm to about 200 ppm, about 75 ppm to about 225 ppm, about 75 ppm to about 250 ppm, about 75 ppm to about 275 ppm, about 75 ppm to about 300 ppm, about 75 ppm to about 325 ppm, about 75 ppm to about 350 ppm, about 75 ppm to about 375 ppm, about 75 ppm to about 400 ppm, about 100 ppm to about 125 ppm, about 100 ppm to about 150 ppm, about 100 ppm to about 175 ppm, about 100 ppm to about 200 ppm, about 100 ppm to about 225 ppm, about 100 ppm to about 250 ppm, about 100 ppm to about 275 ppm, about 100 ppm to about 300 ppm, about 100 ppm to about 325 ppm, about 100 ppm to about 350 ppm, about 100 ppm to about 375 ppm, about 100 ppm to about 400 ppm, about 150 ppm to about 175 ppm, about 150 ppm to about 200 ppm, about 150 ppm to about 225 ppm, about 150 ppm to about 250 ppm, about 150 ppm to about 275 ppm, about 150 ppm to about 300 ppm, about 150 ppm to about 325 ppm, about 150 ppm to about 350 ppm, about 150 ppm to about 375 ppm, about 150 ppm to about 400 ppm, about 200 ppm to about 225 ppm, about 200 ppm to about 250 ppm, about 200 ppm to about 275 ppm, about 200 ppm to about 300 ppm, about 200 ppm to about 325 ppm, about 200 ppm to about 350 ppm, about 200 ppm to about 375 ppm, about 200 ppm to about 400 ppm, about 250 ppm to about 275 ppm, about 250 ppm to about 300 ppm, about 250 ppm to about 325 ppm, about 250 ppm to about 350 ppm, about 250 ppm to about 375 ppm, about 250 ppm to about 400 ppm, about 300 ppm to about 325 ppm, about 300 ppm to about 350 ppm, about 300 ppm to about 375 ppm, about 300 ppm to about 400 ppm, about 350 ppm to about 375 ppm, about 350 ppm to about 400 ppm, about 375 ppm to about 400 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 400 ppm to about 1,100 ppm, about 400 ppm to about 1,200 ppm, about 400 ppm to about 1,300 ppm, about 400 ppm to about 1,400 ppm, about 400 ppm to about 1,500 ppm, about 500 ppm to about 600 ppm, about 500 ppm to about 700 ppm, about 500 ppm to about 800 ppm, about 500 ppm to about 900 ppm, about 500 ppm to about 1,000 ppm, about 500 ppm to about 1,100 ppm, about 500 ppm to about 1,200 ppm, about 500 ppm to about 1,300 ppm, about 500 ppm to about 1,400 ppm, about 500 ppm to about 1,500 ppm, about 600 ppm to about 700 ppm, about 600 ppm to about 800 ppm, about 600 ppm to about 900 ppm, about 600 ppm to about 1,000 ppm, about 600 ppm to about 1,100 ppm, about 600 ppm to about 1,200 ppm, about 600 ppm to about 1,300 ppm, about 600 ppm to about 1,400 ppm, about 600 ppm to about 1,500 ppm, about 700 ppm to about 800 ppm, about 700 ppm to about 900 ppm, about 700 ppm to about 1,000 ppm, about 700 ppm to about 1,100 ppm, about 700 ppm to about 1,200 ppm, about 700 ppm to about 1,300 ppm, about 700 ppm to about 1,400 ppm, about 700 ppm to about 1,500 ppm, about 800 ppm to about 900 ppm, about 800 ppm to about 1,000 ppm, about 800 ppm to about 1,100 ppm, about 800 ppm to about 1,200 ppm, about 800 ppm to about 1,300 ppm, about 800 ppm to about 1,400 ppm, about 800 ppm to about 1,500 ppm, about 900 ppm to about 1,000 ppm, about 900 ppm to about 1,100 ppm, about 900 ppm to about 1,200 ppm, about 900 ppm to about 1,300 ppm, about 900 ppm to about 1,400 ppm, about 900 ppm to about 1,500 ppm, about 1,000 ppm to about 1,100 ppm, about 1,000 ppm to about 1,200 ppm, about 1,000 ppm to about 1,300 ppm, about 1,000 ppm to about 1,400 ppm, about 1,000 ppm to about 1,500 ppm, about 1,100 ppm to about 1,200 ppm, about 1,100 ppm to about 1,300 ppm, about 1,100 ppm to about 1,400 ppm, about 1,100 ppm to about 1,500 ppm, about 1,200 ppm to about 1,300 ppm, about 1,200 ppm to about 1,400 ppm, about 1,200 ppm to about 1,500 ppm, about 1,300 ppm to about 1,400 ppm, about 1,300 ppm to about 1,500 ppm, or about 1,400 ppm to about 1,500 ppm.

115. The kit according to any one of embodiments 109, 110 or 112-114, wherein the one or more disinfectants are in an amount of about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition, or at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0% by weight of the composition, or at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition, or about 0.1% to about 0.5%, about 0.1% to about 0.75%, about 0.1% to about 1.0%, about 0.1% to about 1.5%, about 0.1% to about 2.0%, about 0.1% to about 2.5%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0% or about 5.0% to about 15.0% by weight of the composition.

116. The kit according to any one of embodiments 109, 110 or 112-114, wherein the one or more disinfectants are in an amount of about 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, or 1,000 ppm, or at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, or at least 1,000 ppm, or at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, or at most 1,000 ppm, or about 100 ppm to about 200 ppm, about 100 ppm to about 300 ppm, about 100 ppm to about 400 ppm, about 100 ppm to about 500 ppm, about 100 ppm to about 600 ppm, about 100 ppm to about 700 ppm, about 100 ppm to about 800 ppm, about 100 ppm to about 900 ppm, about 100 ppm to about 1,000 ppm, about 200 ppm to about 300 ppm, about 200 ppm to about 400 ppm, about 200 ppm to about 500 ppm, about 200 ppm to about 600 ppm, about 200 ppm to about 700 ppm, about 200 ppm to about 800 ppm, about 200 ppm to about 900 ppm, about 200 ppm to about 1,000 ppm, about 300 ppm to about 400 ppm, about 300 ppm to about 500 ppm, about 300 ppm to about 600 ppm, about 300 ppm to about 700 ppm, about 300 ppm to about 800 ppm, about 300 ppm to about 900 ppm, about 300 ppm to about 1,000 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 500 ppm to about 600 ppm, about 500 ppm to about 700 ppm, about 500 ppm to about 800 ppm, about 500 ppm to about 900 ppm, about 500 ppm to about 1,000 ppm, about 600 ppm to about 700 ppm, about 600 ppm to about 800 ppm, about 600 ppm to about 900 ppm, about 600 ppm to about 1,000 ppm, about 700 ppm to about 800 ppm, about 700 ppm to about 900 ppm, about 700 ppm to about 1,000 ppm, about 800 ppm to about 900 ppm, about 800 ppm to about 1,000 ppm, or about 900 ppm to about 1,000 ppm.

117. The kit according to any one of embodiments 109, 110 or 112-116, wherein the one or more disinfectants include one or more compounds containing a guanide moiety or functional group, one or more aldehyde-containing compounds, one or more organic peroxides, or any combination thereof.

118. The kit according to embodiment 117, wherein the one or more guanide-containing compounds comprise, consist essentially of, or consist of comprise, consist essentially of, or consist of a biguanide, a biguanide-containing compound, a biguanidine, a biguanidine-containing compound, a triguanide, a triguanide-containing compound, or any combination thereof.

119. The kit according to embodiment 118, wherein the one or more biguanide-containing compounds include a polyhexamethylene biguanide (PHMB), a polyaminopropyl biguanide (PAPB), a 1,1'-(1,6-Hexanediyl)bis{2-[N'-(2-ethylhexyl)carbamimidoyl]guanidine} (alexidine), a chlorhexidine, a chlorhexidine gluconate, or any combination thereof.

120. The kit according to embodiment 117, wherein the one or more aldehyde-containing compounds include one or more aldehydes, one or more dialdehydes, or any combination thereof.

121. The kit according to embodiment 120, wherein the one or more aldehydes includes one or more linear aldehydes, one or more branched aldehydes, one or more cyclic aldehydes, one or more aromatic aldehydes, or any combination thereof.

122. The kit according to embodiment 120 or 121, wherein the one or more aldehydes includes formaldehyde, acetaldehyde, propionaldehyde, butyraldehyde, or any combination thereof.

123. The kit according to embodiment 120, wherein the one or more dialdehydes includes one or more linear dialdehydes, one or more branched dialdehydes, one or more cyclic dialdehydes, one or more aromatic dialdehydes, or any combination thereof.

124. The kit according to embodiment 120 or 121, wherein the one or more dialdehydes includes oxaldehyde, malondialdehyde, glutaraldehyde, succinicdialdehyde, phthalaldehyde (ortho-phthalaldehyde), isophthalaldehyde (meta-phthalaldehyde), terephthalaldehyde (para-phthalaldehyde), or any combination thereof.

125. The kit according to embodiment 117, wherein the one or more organic peroxides include benzoyl peroxide, ethaneperoxoic acid (peracetic acid), or any combination thereof.

126. The kit according to any one of embodiments 117-125, wherein the one or more guanide-containing compounds, one or more aldehyde-containing compounds, and/or one or more organic peroxides are in an amount of about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 6.5%, about 7.0%, about 7.5%, about 8.0%, about 8.5%, about 9.0%, about 9.5%, about 10.0%. about 11%, about 12%, about 13%, about 14%, about 15%, about 20%, about 25%, or about 30% by weight of the composition, or at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, at least 10.0%, at least 11%, at least 12%, at least 13%, at least 14%, at least 15%, at least 20%, at least 25%, or at least 30% by weight of the composition, or at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0%, at most 10.0%, at most 11%, at most 12%, at most 13%, at most 14%, at most 15%, at most 20%, at most 25%, or at most 30% by weight of the composition, or about 0.1% to about 0.5%, about 0.1% to about 0.75%, about 0.1% to about 1.0%, about 0.1% to about 1.5%, about 0.1% to about 2.0%, about 0.1% to about 2.5%, about 0.1% to about 3.0%, about 0.1% to about 3.5%, about 0.1% to about 4.0%, about 0.1% to about 4.5%, about 0.1% to about 5.0%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.2% to about 3.0%, about 0.2% to about 3.5%, about 0.2% to about 4.0%, about 0.2% to about 4.5%, about 0.2% to about 5.0%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 1.0% to about 15.0%, about 1.0% to about 20.0%, about 1.0% to about 25.0%, about 1.0% to about 30.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 2.0% to about 15.0%, about 2.0% to about 20.0%, about 2.0% to about 25.0%, about 2.0% to about 30.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0%, about 5.0% to about 15.0%, about 5.0% to about 20.0%, about 5.0% to about 25.0%, about 5.0% to about 30.0%, about 6.0% to about 7.0%, about 6.0% to about 7.5%, about 6.0% to about 8.0%, about 6.0% to about 9.0%, about 6.0% to about 10.0%, about 6.0% to about 11.0%, about 6.0% to about 12.0%, about 6.0% to about 13.0%, about 6.0% to about 14.0%, about 6.0% to about 15.0%, about 6.0% to about 20.0%, about 6.0% to about 25.0%, about 6.0% to about 30.0%, about 7.0% to about 8.0%, about 7.0% to about 9.0%, about 7.0% to about 10.0%, about 7.0% to about 11.0%, about 7.0% to about 12.0%, about 7.0% to about 13.0%, about 7.0% to about 14.0%, about 7.0% to about 15.0%, about 7.0% to about 20.0%, about 7.0% to about 25.0%, about 7.0% to about 30.0%, about 8.0% to about 9.0%, about 8.0% to about 10.0%, about 8.0% to about 11.0%, about 8.0% to about 12.0%, about 8.0% to about 13.0%, about 8.0% to about 14.0%, about 8.0% to about 15.0%, about 8.0% to about 20.0%, about 8.0% to about 25.0%, about 8.0% to about 30.0%, about 9.0% to about 10.0%, about 9.0% to about 11.0%, about 9.0% to about 12.0%, about 9.0% to about 13.0%, about 9.0% to about 14.0%, about 9.0% to about 15.0%, about 9.0% to about 20.0%, about 9.0% to about 25.0%, about 9.0% to about 30.0%, about 10.0% to about 11.0%, about 10.0% to about 12.0%, about 10.0% to about 13.0%, about 10.0% to about 14.0%, about 10.0% to about 15.0%, about 10.0% to about 20.0%, about 10.0% to about 25.0%, about 10.0% to about 30.0%, about 15.0% to about 20.0%, about 15.0% to about 25.0%, about 15.0% to about 30.0%, about 20.0% to about 25.0%, about 20.0% to about 30.0%, or about 20.0% to about 30.0%, by weight of the composition.

127. The kit according to any one of embodiments 117-125, wherein the one or more aldehydes and/or one or more dialdehydes are in an amount of about 100 ppm, 125 ppm, 150 ppm, 175 ppm, 200 ppm, 225 ppm, 250 ppm, 275 ppm, 300 ppm, 325 ppm, 350 ppm, 375 ppm, 400 ppm, 425 ppm, 450 ppm, 475 ppm, 500 ppm, 525 ppm, 550 ppm, 575 ppm, 600 ppm, 625 ppm, 650 ppm, 675 ppm, 700 ppm, 725 ppm, 750 ppm, 775 ppm, 800 ppm, 825 ppm, 850 ppm, 875 ppm, 900 ppm, 925 ppm, 950 ppm, 975 ppm, or 1,000 ppm, or at least 100 ppm, at least 125 ppm, at least 150 ppm, at least 175 ppm, at least 200 ppm, at least 225 ppm, at least 250 ppm, at least 275 ppm, at least 300 ppm, at least 325 ppm, at least 350 ppm, at least 375 ppm, at least 400 ppm, at least 425 ppm, at least 450 ppm, at least 475 ppm, at least 500 ppm, at least 525 ppm, at least 550 ppm, at least 575 ppm, at least 600 ppm, at least 625 ppm, at least 650 ppm, at least 675 ppm, at least 700 ppm, at least 725 ppm, at least 750 ppm, at least 775 ppm, at least 800 ppm, at least 825 ppm, at least 850 ppm, at least 875 ppm, at least 900 ppm, at least 925 ppm, at least 950 ppm, at least 975 ppm, or at least 1,000 ppm, or at most 100 ppm, at most 125 ppm, at most 150 ppm, at most 175 ppm, at most 200 ppm, at most 225 ppm, at most 250 ppm, at most 275 ppm, at most 300 ppm, at most 325 ppm, at most 350 ppm, at most 375 ppm, at most 400 ppm, at most 425 ppm, at most 450 ppm, at most 475 ppm, at most 500 ppm, at most 525 ppm, at most 550 ppm, at most 575 ppm, at most 600 ppm, at most 625 ppm, at most 650 ppm, at most 675 ppm, at most 700 ppm, at most 725 ppm, at most 750 ppm, at most 775 ppm, at most 800 ppm, at most 825 ppm, at most 850 ppm, at most 875 ppm, at most 900 ppm, at most 925 ppm, at most 950 ppm, at most 975 ppm, or at most 1,000 ppm.

128. The kit according to any one of embodiments 117-125, wherein the one or more aldehydes and/or one or more dialdehydes are in an amount of about 100 ppm to about 200 ppm, about 100 ppm to about 300 ppm, about 100 ppm to about 400 ppm, about 100 ppm to about 500 ppm, about 100 ppm to about 600 ppm, about 100 ppm to about 700 ppm, about 100 ppm to about 800 ppm, about 100 ppm to about 900 ppm, about 100 ppm to about 1,000 ppm, about 200 ppm to about 300 ppm, about 200 ppm to about 400 ppm, about 200 ppm to about 500 ppm, about 200 ppm to about 600 ppm, about 200 ppm to about 700 ppm, about 200 ppm to about 800 ppm, about 200 ppm to about 900 ppm, about 200 ppm to about 1,000 ppm, about 300 ppm to about 400 ppm, about 300 ppm to about 500 ppm, about 300 ppm to about 600 ppm, about 300 ppm to about 700 ppm, about 300 ppm to about 800 ppm, about 300 ppm to about 900 ppm, about 300 ppm to about 1,000 ppm, about 400 ppm to about 500 ppm, about 400 ppm to about 600 ppm, about 400 ppm to about 700 ppm, about 400 ppm to about 800 ppm, about 400 ppm to about 900 ppm, about 400 ppm to about 1,000 ppm, about 500 ppm to about 600 ppm, about 500 ppm to about 700 ppm, about 500 ppm to about 800 ppm, about 500 ppm to about 900 ppm, about 500 ppm to about 1,000 ppm, about 600 ppm to about 700 ppm, about 600 ppm to about 800 ppm, about 600 ppm to about 900 ppm, about 600 ppm to about 1,000 ppm, about 700 ppm to about 800 ppm, about 700 ppm to about 900 ppm, about 700 ppm to about 1,000 ppm, about 800 ppm to about 900 ppm, about 800 ppm to about 1,000 ppm, or about 900 ppm to about 1,000 ppm.

129. The kit according to any one of embodiments 109, 110 or 112-128, wherein the one or more alcohols is methanol, ethanol, propanol, isopropanol, butanol, pentanol, and 1-hexadecanol.

130. The kit according to any one of embodiments 109, 110 or 112-129, wherein the one or more alcohols are in an amount of about 40%, about 45%, about 50%, about 55%, about 60%, about 65%, about 70%, about 75%, about 80%, about 85%, about 90%, about 95%, about 96%, about 97%, about 98%, or about 99%, by weight of the composition, or at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%, by weight of the composition, or at most 40%, at most 45%, at most 50%, at most 55%, at most 60%, at most 65%, at most 70%, at most 75%, at most 80%, at most 85%, at most 90%, at most 95%, at most 96%, at most 97%, at most 98%, or at most 99%, by weight of the composition, about 40% to about 50%, about 40% to about 60%, about 40% to about 70%, about 40% to about 80%, about 40% to about 90%, about 40% to about 95%, about 40% to about 97%, about 40% to about 99%, about 50% to about 60%, about 50% to about 70%, about 50% to about 80%, about 50% to about 90%, about 50% to about 95%, about 50% to about 97%, about 50% to about 99%, about 60% to about 70%, about 60% to about 80%, about 60% to about 90%, about 60% to about 95%, about 60% to about 97%, about 60% to about 99%, about 70% to about 80%, about 70% to about 90%, about 70% to about 95%, about 70% to about 97%, about 70% to about 99%, about 80% to about 90%, about 80% to about 95%, about 80% to about 97%, about 80% to about 99%, about 90% to about 95%, about 90% to about 97%, about 90% to about 99%, by weight of the composition.

131. The kit according to any one of embodiments 112-130, wherein the one or more cationic surfactants include one or more quaternary ammonium surfactants, pH-dependent primary amine surfactant, pH-dependent secondary amine surfactant, pH-dependent tertiary amine surfactant, or any combination thereof.

132. The kit according to embodiment 131, wherein the one or more quaternary ammonium surfactants include benzalkonium chloride (BAC), benzethonium chloride (BZT), benzododecinium bromide (or dimethyldodecylbenzylammonium bromide), bronidox, (or 5-bromo-5-nitro-1,3-dioxane), carbethopendecinium bromide, cetalkonium chloride (CKC), cetrimonium, cetrimide, cetylpyridinium chloride (CPC), cetyl trimethylammonium bromide (CTAB or cetrimonium bromide) and cetyl trimethylammonium chloride (CTAC or cetrimonium chloride), didecyldimethylammonium chloride (DDAC), dioctadecyldimethylammonium bromide (DODAB or dimethyldioctadecylammonium bromide), dioctadecyldimethylammonium chloride (DODAC or dimethyldioctadecylammonium chloride), docosyltrimethylammonium chloride (DCTAC or behentrimonium chloride), dofanium chloride, domiphen bromide, methylbenzethonium chloride, octenidine dihydrochloride, polidronium chloride, stearalkonium chloride (or dimethylbenzyloctadecylammonium), tetraethylammonium bromide, tetramethylammonium hydroxide (TMAH) and thonzonium bromide, or any combination thereof.

133. The kit according to any one of embodiments 112-132, wherein the one or more cationic surfactants are in an amount of aspects of, e.g., about 0.001%, about 0.005%, about 0.0075%, about 0.01%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, about 5.0%, about 6.0%, about 7.0%, about 7.5%, about 8.0%, about 9.0% or about 10.0% by weight of the composition, or at least 0.001%, at least 0.005%, at least 0.0075%, at least 0.01%, at least 0.05%, at least 0.075%, at least 0.1%, at least 0.25%, at least 0.5%, at least 0.75%, at least 1.0%, at least 1.5%, at least 2.0%, at least 2.5%, at least 3.0%, at least 4.0%, at least 5.0%, at least 6.0%, at least 7.0%, at least 7.5%, at least 8.0%, at least 9.0%, or at least 10.0% by weight of the composition, or at most 0.001%, at most 0.005%, at most 0.0075%, at most 0.01%, at most 0.05%, at most 0.075%, at most 0.1%, at most 0.25%, at most 0.5%, at most 0.75%, at most 1.0%, at most 1.5%, at most 2.0%, at most 2.5%, at most 3.0%, at most 4.0%, at most 5.0%, at most 6.0%, at most 7.5%, at most 8.0%, at most 9.0% or at most 10.0% by weight of the composition, or about 0.001% to about 0.005%, about 0.001% to about 0.0075%, about 0.001% to about 0.01%, about 0.001% to about 0.025%, about 0.001% to about 0.05%, about 0.001% to about 0.075%, about 0.001% to about 0.1%, about 0.001% to about 0.25%, about 0.001% to about 0.75%, about 0.001% to about 1.0%, about 0.005% to about 0.0075%, about 0.005% to about 0.01%, about 0.005% to about 0.025%, about 0.005% to about 0.05%, about 0.005% to about 0.075%, about 0.005% to about 0.1%, about 0.005% to about 0.25%, about 0.005% to about 0.75%, about 0.005% to about 1.0%, about 0.01% to about 0.05%, about 0.01% to about 0.075%, about 0.01% to about 0.1%, about 0.01% to about 0.25%, about 0.01% to about 0.5%, about 0.01% to about 0.75%, about 0.01% to about 1.0%, about 0.01% to about 1.5%, about 0.01% to about 2.0%, about 0.01% to about 2.5%, about 0.05% to about 0.075%, about 0.05% to about 0.1%, about 0.05% to about 0.25%, about 0.05% to about 0.5%, about 0.05% to about 0.75%, about 0.05% to about 1.0%, about 0.05% to about 1.5%, about 0.05% to about 2.0%, about 0.05% to about 2.5%, about 0.1% to about 0.5%, about 0.1% to about 0.75%, about 0.1% to about 1.0%, about 0.1% to about 1.5%, about 0.1% to about 2.0%, about 0.1% to about 2.5%, about 0.1% to about 3.0%, about 0.1% to about 4.0%, about 0.1% to about 5.0%, about 0.2% to about 0.5%, about 0.2% to about 0.75%, about 0.2% to about 1.0%, about 0.2% to about 1.5%, about 0.2% to about 2.0%, about 0.2% to about 2.5%, about 0.2% to about 3.0%, about 0.2% to about 4.0%, about 0.2% to about 5.0%, about 0.5% to about 1.0%, about 0.5% to about 1.5%, about 0.5% to about 2.0%, about 0.5% to about 2.5%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10.0%, about 1.0% to about 2.5%, about 1.0% to about 3.0%, about 1.0% to about 4.0%, about 1.0% to about 5.0%, about 1.0% to about 6.0%, about 1.0% to about 7.0%, about 1.0% to about 7.5%, about 1.0% to about 8.0%, about 1.0% to about 9.0%, about 1.0% to about 10.0%, about 2.0% to about 2.5%, about 2.0% to about 3.0%, about 2.0% to about 4.0%, about 2.0% to about 5.0%, about 2.0% to about 6.0%, about 2.0% to about 7.0%, about 2.0% to about 7.5%, about 2.0% to about 8.0%, about 2.0% to about 9.0%, about 2.0% to about 10.0%, about 5.0% to about 6.0%, about 5.0% to about 7.0%, about 5.0% to about 7.5%, about 5.0% to about 8.0%, about 5.0% to about 9.0%, about 5.0% to about 10.0%, about 5.0% to about 11.0%, about 5.0% to about 12.0%, about 5.0% to about 13.0%, about 5.0% to about 14.0% or about 5.0% to about 15.0% by weight of the composition.

134. A method to clean, disinfect and/or sterilize a device, the method comprising, consisting essentially of, or consisting of applying a composition as defined in any one of embodiments 1-108 or applying the components as defined in any one of embodiments 109-133, to a device, wherein application of the composition cleans, disinfects and/or sterilizes the device.

135. A composition as defined in any one of embodiments 1-108 or the components as defined in any one of embodiments 109-133 for use in cleaning, disinfecting and/or sterilizing a device.

136. Use of a composition as defined in any one of embodiments 1-108 or use of the components as defined in any one of embodiments 109-133 to clean, disinfect and/or sterilize a device.

137. A method to clean, disinfect and/or sterilize a surface area, the method comprising, consisting essentially of, or consisting of applying a composition as defined in any one of embodiments 1-108 or applying the components as defined in any one of embodiments 109-133, to a device, wherein application of the composition cleans, disinfects and/or sterilizes the device.

138. A composition as defined in any one of embodiments 1-108 or the components as defined in any one of embodiments 109-133 for use in cleaning, disinfecting and/or sterilizing a surface area.

139. Use of a composition as defined in any one of embodiments 1-108 or use of the components as defined in any one of embodiments 109-133 to clean, disinfect and/or sterilize a surface area.

140. The method of embodiment 137, or the use of embodiment 138 or 139, wherein the surface area is a porous surface area or a non-porous surface area.

141. The method of embodiment 137 or 140, or the use of any one of embodiments 138-140, wherein the surface area comprises a table top, countertop, floor, wall, ceiling, window, door, door handle, shower, bath, sink, faucet, toilet, toilet seat, drain, equipment, machinery, personal protective gear, personal biohazard gear, a medical device, dental device, pharmaceutical device, veterinary device, mortuary device or human skin.

142. The method of embodiment 141, or the use of embodiment 141, wherein the medical device is a surgical instrument, a respiratory therapy instrument, an anesthesia instrument, a catheter, an implant, a probe, an endoscope, an arthroscope, a laparoscope, a blade, a cystoscope, a spirometer, a CPAP mask and tubing, dialysis instrument and accessories, a heart-lung machine and accessories, a heart-lung bypass machine and accessories, and a diaphragm fitting ring.

143. A method to clean, disinfect and/or sterilize a microbial infection in an individual, the method comprising, consisting essentially of, or consisting of applying a composition as defined in any one of embodiments 1-108 or applying the components as defined in any one of embodiments 109-133 to the individual, wherein application of the composition cleans, disinfects and/or sterilizes the device.

144. A composition as defined in any one of embodiments 1-108 or the components as defined in any one of embodiments 109-133 for use in cleaning, disinfecting and/or sterilizing a microbial infection in an individual.

145. Use of a composition as defined in any one of embodiments 1-108 or use of the components as defined in any one of embodiments 109-133 to clean, disinfect and/or sterilize a microbial infection in an individual.

146. The method of embodiment 143, or the use of embodiment 144 or 145, wherein application of the composition is applied topically or administered enterally or parenterally.

147. The method of any one of embodiments 137, 140, 141, 143 or 146, or the use of any one of embodiments 138-141 or 144-146, wherein the composition is applied daily, every other day, every third of day, once a week, multiple times per week, once a month, multiple times per month, once a year or multiple times per year, as desired.

148. The method of any one of embodiments 137, 140, 141, 143, 146 or 147, or the use of any one of embodiments 138-141 or 144-147, wherein the composition is applied multiple times per day.

149. The method of any one of embodiments 134, 137, or 143, or the use of any one of embodiments 135, 136, 138, 139, 144 or 145, wherein the composition is applied to a device, like a medical device, a surface, or an individual for, e.g., about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 70 minutes, about 80 minutes, about 90 minutes, about 100 minutes, about 110 minutes, or about 120 minutes; or is applied to a device, like a medical device, a surface, or an individual for, e.g., at least 1 minute, at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 60 minutes, at least 70 minutes, at least 80 minutes, at least 90 minutes, at least 100 minutes, at least 110 minutes, or at least 120 minutes. In yet other aspects of this embodiment, a composition disclosed herein is applied to device, like a medical device, a surface, or an individual for, e.g., at most 1 minute, at most 5 minutes, at most 10 minutes, at most 15 minutes, at most 20 minutes, at most 25 minutes, at most 30 minutes, at most 35 minutes, at most 40 minutes, at most 45 minutes, at most 50 minutes, at most 55 minutes, at most 60 minutes, at most 70 minutes, at most 80 minutes, at most 90 minutes, at most 100 minutes, at most 110 minutes, or at most 120 minutes; or is applied to a device, like a medical device, a surface, or an individual for, e.g., about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 1 minute to about 35 minutes, about 1 minute to about 40 minutes, about 1 minute to about 45 minutes, about 1 minute to about 50 minutes, about 1 minute to about 55 minutes, about 1 minute to about 60 minutes, about 5 minutes to about 10 minutes, about 5 minutes to about 15 minutes, about 5 minutes to about 20 minutes, about 5 minutes to about 25 minutes, about 5 minutes to about 30 minutes, about 5 minutes to about 35 minutes, about 5 minutes to about 40 minutes, about 5 minutes to about 45 minutes, about 5 minutes to about 50 minutes, about 5 minutes to about 55 minutes, about 5 minutes to about 60 minutes, about 5 minutes to about 70 minutes, about 5 minutes to about 80 minutes, about 5 minutes to about 90 minutes, about 5 minutes to about 100 minutes, about 5 minutes to about 110 minutes, about 5 minutes to about 120 minutes, about 10 minutes to about 15 minutes, about 10 minutes to about 20 minutes, about 10 minutes to about 25 minutes, about 10 minutes to about 30 minutes, about 10 minutes to about 35 minutes, about 10 minutes to about 40 minutes, about 10 minutes to about 45 minutes, about 10 minutes to about 50 minutes, about 10 minutes to about 55 minutes, about 10 minutes to about 60 minutes, about 10 minutes to about 70 minutes, about 10 minutes to about 80 minutes, about 10 minutes to about 90 minutes, about 10 minutes to about 100 minutes, about 10 minutes to about 110 minutes, about 10 minutes to about 120 minutes, about 15 minutes to about 20 minutes, about 15 minutes to about 25 minutes, about 15 minutes to about 30 minutes, about 15 minutes to about 35 minutes, about 15 minutes to about 40 minutes, about 15 minutes to about 45 minutes, about 15 minutes to about 50 minutes, about 15 minutes to about 55 minutes, about 15 minutes to about 60 minutes, about 15 minutes to about 70 minutes, about 15 minutes to about 80 minutes, about 15 minutes to about 90 minutes, about 15 minutes to about 100 minutes, about 15 minutes to about 110 minutes, about 15 minutes to about 120 minutes, about 20 minutes to about 25 minutes, about 20 minutes to about 30 minutes, about 20 minutes to about 35 minutes, about 20 minutes to about 40 minutes, about 20 minutes to about 45 minutes, about 20 minutes to about 50 minutes, about 20 minutes to about 55 minutes, about 20 minutes to about 60 minutes, about 20 minutes to about 70 minutes, about 20 minutes to about 80 minutes, about 20 minutes to about 90 minutes, about 20 minutes to about 100 minutes, about 20 minutes to about 110 minutes, about 20 minutes to about 120 minutes, about 25 minutes to about 30 minutes, about 25 minutes to about 35 minutes, about 25 minutes to about 40 minutes, about 25 minutes to about 45 minutes, about 25 minutes to about 50 minutes, about 25 minutes to about 55 minutes, about 25 minutes to about 60 minutes, about 25 minutes to about 70 minutes, about 25 minutes to about 80 minutes, about 25 minutes to about 90 minutes, about 25 minutes to about 100 minutes, about 25 minutes to about 110 minutes, about 25 minutes to about 120 minutes, about 30 minutes to about 35 minutes, about 30 minutes to about 40 minutes, about 30 minutes to about 45 minutes, about 30 minutes to about 50 minutes, about 30 minutes to about 55 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 35 minutes to about 40 minutes, about 35 minutes to about 45 minutes, about 35 minutes to about 50 minutes, about 35 minutes to about 55 minutes, about 35 minutes to about 60 minutes, about 35 minutes to about 70 minutes, about 35 minutes to about 80 minutes, about 35 minutes to about 90 minutes, about 35 minutes to about 100 minutes, about 35 minutes to about 110 minutes, about 35 minutes to about 120 minutes, about 40 minutes to about 45 minutes, about 40 minutes to about 50 minutes, about 40 minutes to about 55 minutes, about 40 minutes to about 60 minutes, about 40 minutes to about 70 minutes, about 40 minutes to about 80 minutes, about 40 minutes to about 90 minutes, about 40 minutes to about 100 minutes, about 40 minutes to about 110 minutes, about 40 minutes to about 120 minutes, about 45 minutes to about 50 minutes, about 45 minutes to about 55 minutes, about 45 minutes to about 60 minutes, about 45 minutes to about 70 minutes, about 45 minutes to about 80 minutes, about 45 minutes to about 90 minutes, about 45 minutes to about 100 minutes, about 45 minutes to about 110 minutes, about 45 minutes to about 120 minutes, about 50 minutes to about 55 minutes, about 50 minutes to about 60 minutes, about 50 minutes to about 70 minutes, about 50 minutes to about 80 minutes, about 50 minutes to about 90 minutes, about 50 minutes to about 100 minutes, about 50 minutes to about 110 minutes, about 50 minutes to about 120 minutes, about 55 minutes to about 60 minutes, about 55 minutes to about 70 minutes, about 55 minutes to about 80 minutes, about 55 minutes to about 90 minutes, about 55 minutes to about 100 minutes, about 55 minutes to about 110 minutes, about 55 minutes to about 120 minutes, about 60 minutes to about 70 minutes, about 60 minutes to about 80 minutes, about 60 minutes to about 90 minutes, about 60 minutes to about 100 minutes, about 60 minutes to about 110 minutes, about 60 minutes to about 120 minutes, about 70 minutes to about 80 minutes, about 70 minutes to about 90 minutes, about 70 minutes to about 100 minutes, about 70 minutes to about 110 minutes, about 70 minutes to about 120 minutes, about 80 minutes to about 90 minutes, about 80 minutes to about 100 minutes, about 80 minutes to about 110 minutes, about 80 minutes to about 120 minutes, about 90 minutes to about 100 minutes, about 90 minutes to about 110 minutes, about 90 minutes to about 120 minutes, about 100 minutes to about 110 minutes, about 100 minutes to about 120 minutes, or about 110 minutes to about 120 minutes.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compositions, methods and uses disclosed herein.

Example 1

Compositions

This example illustrates how to formulate a composition disclosed herein. The components listed below were mixed at ambient temperature using a high shear mixer until the mixture was uniform. The pH of the mixture was adjusted as shown. For hypochlorous acid amounts, unless indicated otherwise, the amount is the final concentration after mixing with other components.

TABLE 1

Composition Formulations

| Component | F1 | F2 | F3 | F4 | F5 | F6 |
|---|---|---|---|---|---|---|
| Hypochlorous Acid | 84 ppm | 84 ppm | 84 ppm | 97 ppm | 97 ppm | 97 ppm |
| Polyhexamethylene biguanide | — | — | — | 0.25% | 0.5% | 1.0% |
| Isopropyl Alcohol | — | — | — | — | — | — |
| Glutaraldehyde | 0.1% | 0.25% | 0.5% | — | — | — |
| Water | q.s. | q.s. | q.s. | q.s. | q.s. | q.s. |
| pH | 5.8 | 6.2 | 6.25 | 6.85 | 6.5 | 6.7 |

TABLE 2

Composition Formulations

| Component | F7 | F8 | F9 | F10 | F11 | F12 |
|---|---|---|---|---|---|---|
| Hypochlorous Acid | 97 ppm | 97 ppm | 97 ppm | 97 ppm | 97 ppm | 97 ppm |
| Polyhexamethylene biguanide | — | — | — | — | — | — |
| Isopropyl Alcohol | — | — | — | — | — | — |
| Glutaraldehyde | 0.5% | 0.5% | 0.5% | 0.25% | 0.25% | 0.25% |
| Sodium Lauryl Sulfate | 2% | 2% | 2% | 2% | 2% | 2% |
| Water | q.s. | q.s. | q.s. | q.s. | q.s. | q.s. |
| pH | 3 | 4 | 5 | 3.5 | 4.5 | 5.5 |

TABLE 3

Composition Formulations

| Component | F13 | F14 | F15 | F16 | F17 | F18 |
|---|---|---|---|---|---|---|
| Hypochlorous Acid | 66 ppm | 76 ppm | 80 ppm | 82 ppm | 73 ppm | 75 ppm |
| Polyhexamethylene biguanide | — | — | — | — | — | — |
| Isopropyl Alcohol | — | — | — | — | — | — |
| Glutaraldehyde | 0.5% | 0.5% | 0.5% | 0.25% | 0.25% | 0.25% |
| Water | q.s. | q.s. | q.s. | q.s. | q.s. | q.s. |
| pH | 3 | 4 | 5 | 3.5 | 4.5 | 5.5 |

TABLE 4

Composition Formulations

| Component | F19 | F20 | F21 | F22 | F23 | F24 |
|---|---|---|---|---|---|---|
| Hypochlorous Acid | 22 ppm | 18 ppm | 16 ppm | 11 ppm | — | — |
| Polyhexamethylene Biguanide | 1.25% | 1.5% | 1.75% | 2.0% | 2.0% | 3.0% |
| Isopropyl Alcohol | — | — | — | — | 70% | 70% |
| Glutaraldehyde | — | — | — | — | — | — |
| Water | q.s. | q.s. | q.s. | q.s. | q.s. | q.s. |
| pH | 5.75 | 6.6 | 6.4 | 6.9 | ND | ND |

ND, Not Determined.

TABLE 5

Composition Formulations

| Component | F25 | F26 | F27 | F28 | F29 | F30 |
|---|---|---|---|---|---|---|
| Hypochlorous Acid | — | — | — | — | — | — |
| Polyhexamethylene Biguanide | 4.0% | 6.0% | 8.0% | 10% | 0.25% | 0.5% |
| Isopropyl Alcohol | 70% | 70% | 70% | 70% | 70% | 70% |
| Glutaraldehyde | — | — | — | — | — | — |
| Water | q.s. | q.s. | q.s. | q.s. | q.s. | q.s. |
| pH | ND | 6.3 | 6.4 | 6.4 | ND | ND |

ND, Not Determined.

TABLE 6

Composition Formulations

| Component | F31 | F32 | F33 | F34 | F35 | F36 |
|---|---|---|---|---|---|---|
| Hypochlorous Acid | — | — | — | — | — | — |
| Polyhexamethylene Biguanide | 0.75% | 1.0% | 1.25% | 1.5% | 1.75% | 2.0% |
| Isopropyl Alcohol | 70% | 70% | 70% | 70% | 70% | 70% |
| Glutaraldehyde | — | — | — | — | — | — |
| Water | q.s. | q.s. | q.s. | q.s. | q.s. | q.s. |
| pH | ND | ND | ND | ND | ND | ND |

ND, Not Determined.

TABLE 7

Composition Formulations

| Component | F37 | F38 | F39 | F40 | F41 | F42 |
|---|---|---|---|---|---|---|
| Hypochlorous Acid | 96 ppm | 94 ppm | 92 ppm | 90 ppm | 98 ppm | 96 ppm |
| Polyhexamethylene Biguanide | 4.0% | 6.0% | 8.0% | 10.0% | 2.0% | 4.0% |
| Isopropyl Alcohol | — | — | — | — | — | — |
| Glutaraldehyde | — | — | — | — | — | — |
| Water | q.s. | q.s. | q.s. | q.s. | q.s. | q.s. |
| pH | ND | ND | ND | ND | ND | ND |

ND, Not Determined.

TABLE 8

Composition Formulations

| Component | F43 | F44 | F45 | F46 | F47 | F48 |
|---|---|---|---|---|---|---|
| Hypochlorous Acid | 94 ppm | 92 ppm | 90 ppm | 46 ppm | 58 ppm | — |
| Polyhexamethylene Biguanide | 6.0% | 8.0% | 10.0% | 0.25% | 0.25% | 0.25% |
| Isopropyl Alcohol | — | — | — | — | — | 40% |
| Glutaraldehyde | — | — | — | — | — | — |
| Water | q.s. | q.s. | q.s. | q.s. | q.s. | q.s. |
| pH | ND | ND | ND | 6.8 | 6.5 | 5.4 |

ND, Not Determined.

TABLE 9

Composition Formulations

| Component | F49 | F50 | F51 | F52 | F53 | F54 |
|---|---|---|---|---|---|---|
| Hypochlorous Acid | — | — | — | — | 83 ppm | 56 ppm |
| Polyhexamethylene Biguanide | 0.25% | 0.01% | 0.001% | 0.05% | — | 0.01% |

TABLE 9-continued

Composition Formulations

| Component | F49 | F50 | F51 | F52 | F53 | F54 |
|---|---|---|---|---|---|---|
| Isopropyl Alcohol | 20% | 70% | 70% | 70% | — | — |
| Glutaraldehyde | — | — | — | — | — | — |
| Water | q.s. | q.s. | q.s. | q.s. | q.s. | q.s. |
| pH | 5.5 | 5.8 | 5.8 | 6.0 | 6.6 | 7.4 |

TABLE 10

Composition Formulations

| Component | F55 | F56 | F57 | F58 | F59 | F60 |
|---|---|---|---|---|---|---|
| Hypochlorous Acid | — | — | — | — | — | — |
| Polyhexamethylene Biguanide | 8.0% | 9.5% | 5.0% | 10.0% | 10.0% | 10.0% |
| Isopropyl Alcohol | 70% | 70% | 70% | 65% | 60% | 50% |
| Glutaraldehyde | 2.0% | — | — | — | — | — |
| ortho-Phthalaldehyde | — | 0.5% | — | — | — | — |
| Benzalkonium Chloride | — | — | 5.0% | 5.0% | — | — |
| Water | q.s. | q.s. | q.s. | q.s. | q.s. | q.s. |
| pH | 4.0 | 3.9 | 7.7 | 7.3 | 6.0 | 6.0 |

TABLE 11

Composition Formulations

| Component | F61 | F62 | F63 | F64 | F65 | F66 |
|---|---|---|---|---|---|---|
| Hypochlorous Acid | — | — | — | — | — | — |
| Polyhexamethylene Biguanide | 10.0% | 10.0% | 10.0% | 10.0% | 1% | 2% |
| Isopropyl Alcohol | — | — | 25.0% | 33.33% | 50% | 50% |
| Ethanol | — | 50.0% | 25.0% | 16.67% | — | — |
| Glutaraldehyde | — | — | — | — | — | — |
| Water | q.s. | q.s. | q.s. | q.s. | q.s. | q.s. |
| pH | ND | 6.15 | 6.38 | 6.29 | 6.01 | 6.19 |

ND, Not Determined.

TABLE 12

Composition Formulations

| Component | F67 | F68 | F69 | F70 | F71 | F97 |
|---|---|---|---|---|---|---|
| Hypochlorous Acid | — | — | — | — | — | 530 ppm* |
| Polyhexamethylene Biguanide | 4.0% | 6.0% | 8.0% | 10.0% | 10.0% | 500 ppm |
| Isopropyl Alcohol | 50.0% | — | 50.0% | 40% | 30.0% | — |
| Ethanol | — | 50.0% | — | — | — | — |
| Cetylpyridinium Chloride | — | — | — | — | — | — |
| Glutaraldehyde | — | — | — | — | — | — |
| Water | q.s. | q.s. | q.s. | q.s. | q.s. | q.s. |
| pH | 6.29 | 6.20 | 6.40 | 6.34 | 6.23 | 2.8 |

*HOCl concentration prior to mixing.

TABLE 13

Formulations for Composition

| Component | F98 | F99 | F111 | F113 | F114 | F136 |
|---|---|---|---|---|---|---|
| Hypochlorous Acid | — | — | — | 107 ppm* | 281 ppm* | — |
| Polyhexamethylene Biguanide | 1% | 1% | 0.12% | 1200 ppm | 1200 ppm | 10% |
| Isopropyl Alcohol | 50% | 20% | 15% | — | — | 45% |
| Ethanol | — | — | — | — | — | — |
| Cetylpyridinium Chloride | — | — | — | — | — | 5.0% |
| Glutaraldehyde | — | — | — | — | — | — |
| Water | q.s. | q.s. | q.s. | q.s | q.s. | q.s. |
| pH | 6.8 | 6.3 | 7.60 | 5.37 | 3.7 | 8.29 |

*HOCl concentration prior to mixing.

TABLE 14

Composition Formulations

| Component | F137 | F159 | F160 | F161 | F162 | F164 |
|---|---|---|---|---|---|---|
| Hypochlorous Acid | — | — | — | — | — | — |
| Polyhexamethylene Biguanide | 6.0% | 5.0% | 10% | 10% | — | — |
| Isopropyl Alcohol | 50.0% | 5.0% | 5.0% | 5.0% | 5.0% | 50.0% |
| Ethanol | — | — | — | — | — | — |
| Cetylpyridinium Chloride | 4.0% | 5.0% | — | — | 10% | 10% |
| Glutaraldehyde | — | — | — | — | — | — |
| TRITON ® CG-110 | — | 2.0% | 2.0% | — | — | 2.0% |
| Water | q.s. | q.s. | q.s. | q.s. | q.s. | q.s. |
| pH | 7.8 | 7.3 | 7.0 | 7.3 | 6.2 | 5.6 |

TABLE 15

Composition Formulations

| Component | F165 | F166 | F167 |
|---|---|---|---|
| Hypochlorous Acid | — | — | — |
| Polyhexamethylene Biguanide | — | — | 10% |
| Isopropyl Alcohol | 50% | — | — |
| Ethanol | — | — | — |
| Cetylpyridinium Chloride | 6.0% | 10% | — |
| Glutaraldehyde | — | — | — |
| TRITON ® CG-110 | 2% | 2% | 2% |
| Poloxamer-407 | — | 2% | 2% |
| Water | q.s. | q.s. | q.s. |
| pH | 6.1 | ND | ND |

ND, Not Determined

Example 2

Spore Viability Assays Using *Bacillus subtilis*

This example illustrates how to conduct a spore viability assay using compositions disclosed herein.

To prepare stock cultures of pathogenic spores, 10 mL nutrient broth was inoculated using a stock culture of *Bacillus subtilis* (ATCC #19659) and incubated on an orbital shaker for 24±2 hours at approximately 150 rpm at 36±1° C. This culture was used to inoculate Tryptic Soy Agar (TSA) plates. Each plate was inoculated with 500 μL of broth culture and the inoculum spread with a sterile L spreader. In addition, the purity of this culture was verified by streaking on TSA plates and incubating plates at 36±1° C. for 24±2 hours. Each plate was wrapped with parafilm. inverted and incubated for 12-14 days at 36±1° C. Following incubation, spores were harvested by adding 10 mL cold sterile water to each plate, the growth removed from the plates using a spreader, and the resulting suspensions were transferred into 15 mL sterile conical tubes. The suspensions were centrifuged at 5,000 rpm (4,500×g) for approximately 10 minutes at room temperature. After removal of the supernatant, the spore pellet was washed by re-suspending pellet with 10 mL cold sterile water and centrifuged at 5,000 rpm (4,500×g) for approximately 10 minutes. This washing step was repeated two more times. The spore pellet was re-suspended with 10 mL sterile water and the spore suspension was stored at 2-5° C. until needed. The spore suspension was stained using stain and the spores examined under the microscope to assess quality of the spores. A minimum of five fields were examined and the ratio of the spores to vegetative cells (or sporangia) was determined. Percentage of spores versus vegetative cells were about 95% spores. Spore titer was determined by preparing serial dilutions, plating the dilutions on TSA plates, incubating plates for 24±2 hours at 36±1° C., and counting the number of colonies formed to determine the titer. The test culture was standardized by using phosphate buffer to achieve a final test culture microbe population of $1.0 \times 10^6$ cfu/mL.

Assay samples were set up with or without serum, such as, e.g., Tryptic Soy Broth (TSB) or Bovine Serum (BS). The purpose of the serum was to better simulate the organic load of blood and other tissue which tends to deactivate an antimicrobial agent. In general, assays were conducted by first incubating a pathogen spore sample with a composition disclosed herein for a specified treatment time period, optionally with serum, and then culturing the sample on growth medium to assess spore viability.

In one series of experiments, assays where the samples were treated with serum were set up to contain 100 µL of pathogen spore suspension (containing about $1 \times 10^6$ cfu/mL), 50 µL of serum, and 850 µL of a composition described in Example 1. For assays where the samples were not treated with serum, samples contained 100 µL of pathogen spore suspension (containing about $1 \times 10^6$ cfu/mL) and 900 µL of a composition described in Example 1. All samples were incubated for 15 minutes and then plated on petri dishes containing TSA growth medium. The inoculated plates were then incubated at 37° C. for 48 hours and the number of bacterial colonies, if any, counted. Please note that while specific amounts and volumes are described, different amounts and volumes can be used. For example, a treated sample can contain 100 µL of pathogen spore suspension (containing about $1 \times 10^6$ cfu/mL), 500 µL of serum, and 9,400 µL of a composition disclosed herein. An untreated sample can contain 100 µL of pathogen spore suspension (containing about $1 \times 10^6$ cfu/mL) and 9,900 µL of a composition disclosed herein.

The results of this series of experiments are shown in Table 16. The results indicate that Composition F4, F6, F13, F14, F42, F45, F80, F83, F88, F89 and F90 show greater potential as a disinfectant for applications involving hard surfaces, devices, and other apparatuses. Compositions showing no growth in the treated samples were selected for further analysis as described in Example 3.

TABLE 16

*B. subtilis* Spore Viability Assay

| Formulation | Treatment Time | Incubation Time | Count[a] No Serum | Count[a] 5% Serum |
|---|---|---|---|---|
| 97 ppm HOCl | 15 minutes | 48 hours | 0 | >500 |
| 0.1% TWEEN ® 80 + 64 ppm HOCl | 15 minutes | 48 hours | 43 | >500 |

TABLE 16-continued

*B. subtilis* Spore Viability Assay

| Formulation | Treatment Time | Incubation Time | Count[a] No Serum | Count[a] 5% Serum |
|---|---|---|---|---|
| 0.25% Glutaraldehyde | 15 minutes | 48 hours | >500 | >500 |
| 0.5% Glutaraldehyde | 15 minutes | 48 hours | >500 | >500 |
| F1 | 15 minutes | 48 hours | 44 | 339 |
| F2 | 15 minutes | 48 hours | 41 | >500 |
| F3 | 15 minutes | 48 hours | >500 | >500 |
| F4 | 15 minutes | 48 hours | 0 | 0 |
| F6 | 15 minutes | 48 hours | 0 | 0 |
| F13 | 15 minutes | 48 hours | 0 | 0 |
| F14 | 15 minutes | 48 hours | 0 | 0 |
| F15 | 15 minutes | 48 hours | >500 | >500 |
| F24 | 15 minutes | 48 hours | 0 | ND |
| F25 | 15 minutes | 48 hours | ND | 3 |
| F28 | 15 minutes | 48 hours | 0 | ND |
| F42 | 15 minutes | 48 hours | ND | 0 |
| F45 | 15 minutes | 48 hours | ND | 0 |
| F78 | 15 minutes | 48 hours | 0 | >500 |
| F79 | 15 minutes | 48 hours | 0 | >500 |
| F80 | 15 minutes | 48 hours | 0 | 0 |
| F81 | 15 minutes | 48 hours | 0 | >500 |
| F82 | 15 minutes | 48 hours | >500 | >500 |
| F83 | 15 minutes | 48 hours | 0 | 0 |
| F84 | 15 minutes | 48 hours | 0 | >500 |
| F85 | 15 minutes | 48 hours | 0 | >500 |
| F86 | 15 minutes | 48 hours | 0 | >500 |
| F87 | 15 minutes | 48 hours | 0 | >500 |
| F88 | 15 minutes | 48 hours | 0 | 0 |
| F89 | 15 minutes | 48 hours | 0 | 0 |
| F90 | 15 minutes | 48 hours | 0 | 0 |
| F91 | 15 minutes | 48 hours | 0 | >500 |

[a]Values designated >500 indicate that there were too many colonies to count (TMTC), so an estimate of great than 500 was assigned.

Example 3

Spore Viability Assays Using *Bacillus subtilis*

This example illustrates how to conduct a spore viability assay using compositions disclosed herein.

Stock pathogen spore suspensions were prepared as described in Example 2.

In one series of experiments, assay samples were prepared as described in Example 2, except that only treated samples were prepared for each composition, the samples were incubated for 30 minutes, a neutralizing agent was used to inhibit the activity of the microbial agent being tested, for each treatment period samples were serially diluted 1 in 10 over a 6-fold range after treatment using a neutralizing agent, and the treated sample was plated on petri dishes containing TSA growth medium, incubated at 30° C. to 35° C. for 5 days and the number of bacterial colonies, if any, counted. The purpose of the neutralizing agent, such as, e.g., Dey-Engley Broth (DE), was to deactivate an antimicrobial agent like Hypochlorous Acid, Polyhexamethylene Biguanide and/or another agent whose activity functions as a cleaner, disinfectant or sterilizer, thereby improving the accuracy of the time point measurement.

The results are presented in Table 17. The results indicate that Composition F62, F63, F64 and F66 show greater potential as a disinfectant for applications involving hard surfaces, devices and other apparatuses. Compositions F67, F68, F69, F70 and F71 also showed potential as a disinfectant for applications involving hard surfaces, devices and other apparatuses.

TABLE 17

B. subtilis Spore Viability Assay

| Formulation | Treatment Time | Incubation Time | Count[a] | | | | | |
|---|---|---|---|---|---|---|---|---|
| | | | 1 | 2 | 3 | 4 | 5 | 6 |
| F62 | 30 minutes | 5 Days | 0 | 0 | 0 | 0 | 0 | 52 |
| F63 | 30 minutes | 5 Days | 0 | 0 | 0 | 0 | 20 | 34 |
| F64 | 30 minutes | 5 Days | 0 | 0 | 0 | >500 | >500 | >500 |
| F65 | 30 minutes | 5 Days | 0 | >500 | >500 | >500 | >500 | >500 |
| F66 | 30 minutes | 5 Days | ND | 0 | 0 | 0 | 0 | 0 |
| F67 | 30 minutes | 5 Days | 0 | 0 | >500 | >500 | >500 | >500 |
| F68 | 30 minutes | 5 Days | 0 | 0 | >500 | >500 | >500 | >500 |
| F69 | 30 minutes | 5 Days | 0 | 0 | >500 | >500 | >500 | >500 |
| F70 | 30 minutes | 5 Days | 0 | 0 | >500 | >500 | >500 | >500 |
| F71 | 30 minutes | 5 Days | 0 | 0 | >500 | >500 | >500 | >500 |
| F72 | 30 minutes | 5 Days | >500 | >500 | >500 | >500 | >500 | >500 |
| F74 | 30 minutes | 5 Days | >500 | >500 | >500 | >500 | >500 | >500 |
| F74 | 30 minutes | 5 Days | >500 | >500 | >500 | >500 | >500 | >500 |
| F75 | 30 minutes | 5 Days | >500 | >500 | >500 | >500 | >500 | >500 |
| F76 | 30 minutes | 5 Days | >500 | >500 | >500 | >500 | >500 | >500 |

[a]Values designated >500 indicate that there were too many colonies to count (TMTC), so an estimate of great than 500 was assigned.
ND, Not Determined.

In another series of experiments, assay samples were prepared as described in Example 2, except that only treated samples were prepared for each composition, the samples were incubated for 30 minutes, 500 µL of pathogenic spore suspension containing about $5 \times 10^6$ cfu/mL was used for Composition F60, a neutralizing agent was used to inhibit the activity of the microbial agent being tested, for each treatment period samples were serially diluted 1 in 10 over a 6-fold range after treatment using a neutralizing agent, and the treated sample was plated on petri dishes containing TSA growth medium, incubated at 35° C.±2° C. for 2 days and the number of bacterial colonies, if any, counted.

The results are presented in Table 18. Compositions F28, F136 and F137 showed a greater than 6 log-reduction in B. subtilis spore viability and Composition F60 showed a 6 log-reduction in spore viability. The results indicate that Compositions F28, F60, F136 and F137 are effective disinfectants.

TABLE 18

B. subtilis Spore Viability Assay

| Formulation | Treatment Time | Incubation Time | Count[a] | | | | | |
|---|---|---|---|---|---|---|---|---|
| | | | 1 | 2 | 3 | 4 | 5 | 6 |
| F28 | 30 minutes | 48 hours | 0 | 0 | 0 | 0 | 0 | 0 |
| F60 | 30 minutes | 48 hours | 0 | 0 | 0 | 0 | 0 | 0 |
| F136 | 30 minutes | 48 hours | 0 | 0 | 0 | 0 | 0 | 0 |
| F137 | 30 minutes | 48 hours | 0 | 0 | 0 | 0 | 0 | 0 |

[a]Values designated >500 indicate that there were too many colonies to count (TMTC), so an estimate of great than 500 was assigned.

Example 4

Stability Experiments

This example illustrates how to conduct composition stability studies using compositions disclosed herein.

Stock pathogen spore suspensions were prepared as described in Example 2.

In one series of experiments, compositions disclosed herein were prepared, loaded into a bottle, and stored at room temperature for 6 months. Assay samples of the compositions from the stored bottles were prepared as described in Example 2, except that only treated samples were prepared for each composition, the samples were incubated for 30 minutes, the pathogen spore suspension contained about $1 \times 10^8$ cfu/mL, a neutralizing agent was used to inhibit the activity of the microbial agent being tested, for each treatment period samples were serially diluted 1 in 10 over a 6-fold range after treatment using a neutralizing agent, and the treated sample was plated on petri dishes containing TSA growth medium, incubated at 30° C. to 35° C. for 5 days and the number of bacterial colonies, if any, counted on the second day of incubation.

The results are presented in Table 19. Composition F60 showed a 6 log-reduction in B. subtilis spore viability. The results indicate that Composition F60 is an effective disinfectant and its effectiveness is stable for at least 6 months.

TABLE 19

B. subtilis Spore Viability Assay

| Formulation | Treatment Time | Incubation Time | Count[a] | | | | | |
|---|---|---|---|---|---|---|---|---|
| | | | 1 | 2 | 3 | 4 | 5 | 6 |
| F60 | 30 minutes | 48 hours | 0 | 0 | 0 | 0 | 0 | 0 |

[a]Values designated >500 indicate that there were too many colonies to count (TMTC), so an estimate of great than 500 was assigned.

Example 5

Bacteria Viability Assays Using Clostridium difficile

This example illustrates how to conduct composition stability studies using compositions disclosed herein.

Stock pathogen bacteria suspensions of Clostridium difficile were prepared by a third-party contract laboratory according to standard industry procedures.

In one series of experiments, assay samples of the compositions were prepared as described in Example 2, except that only treated samples were prepared for each composition, the samples were incubated for 1 minute, a neutralizing agent was used to inhibit the activity of the microbial agent being tested, for each treatment period samples were serially diluted 1 in 10 over a 6-fold range after treatment using a neutralizing agent, and the treated sample was plated on petri dishes containing TSA growth medium, incubated at 30° C. to 35° C. for 2 days and the number of bacterial colonies, if any, counted.

The results are presented in Table 20. Composition F60 showed a 6.0 log reduction in *C. difficile* viability. The results indicate that Composition F60 is an effective disinfectant against *C. difficile* bacteria as well as *B. subtilis* spores.

TABLE 20

| | | | | | | | | |
|---|---|---|---|---|---|---|---|---|
| | *C. difficile* Bacteria Viability Assay | | | | | | | |
| | Treatment | Incubation | | | Count[a] | | | |
| Formulation | Time | Time | 1 | 2 | 3 | 4 | 5 | 6 |
| F60 | 1 minute | 48 hours | 0 | 0 | 0 | 0 | 0 | 0 |

[a]Values designated >500 indicate that there were too many colonies to count (TMTC), so an estimate of great than 500 was assigned.

Example 6

Disinfection of Medical Device

Stock pathogen spore suspensions were prepared as described in Example 2.

A test assay was set up by placing an endoscope into a sterile container inside a biosafety cabinet and inoculating this device with 4.0 mL of a test inoculum solution comprising $1 \times 10^6$ cfu/mL of the pathogenic spore suspension along the 5% organic soil was used to simulate the level of contamination of endoscope in clinical use. The soiled endoscope was then removed from test inoculum solution and air-dried for one hour. The soiled device was then transferred to a sterile plastic container inside a biosafety cabinet and cleaned with Composition F60 (see Example 1). After the cleaning process, the cleaned device was transferred to a sterile plastic container inside a biosafety cabinet and was extracted with sterile water. The extracted water was filtered through a 0.45 um membrane filter. The filter was then used to inoculate a 9 mL culture broth. Two, 10-fold dilutions were then prepared from the inoculate broth, except that the last dilution was in TSM-B broth. Each extracted solution was incubated for 14 days at 30-35° C. Visual turbidity was observed and compared to both negative and positive controls. For positive controls, the soiled device was not cleaned with a test formulation or any other disinfectant but underwent the extraction process. For negative controls, 1) the device was incubated in a control inoculum solution that was identical to the test inoculum solution, except that the solution lacked a pathogenic spore suspension and the organic soil; and 2) the device was left uncoiled and underwent the same cleaning and extraction process as the test device.

Composition F60 showed a 6 log-reduction in *B. subtilis* spore viability. The results indicate that formulation F60 did effectively disinfect an inoculated device at an exposure time of no more than 30 minutes.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

The invention claimed is:

1. A composition consisting of 7% to 13% by weight of the composition of a polyhexamethylene biguanide, 45% to 55% by weight of the composition of an isopropanol, and one or more carriers.

2. The composition according to claim 1, wherein the polyhexamethylene biguanide is in an amount of at least 11% to at most 13% by weight of the composition.

3. The composition according to claim 1, wherein the polyhexamethylene biguanide is in an amount of at least 7% to at most 11% by weight of the composition.

4. The composition according to claim 1, wherein the isopropanol is in an amount of at least 50% to at most 55% by weight of the composition.

5. The composition according to claim 1, wherein the isopropanol is in an amount of at least 45% to at most 50% by weight of the composition.

6. The composition according to claim 1, wherein the polyhexamethylene biguanide is in an amount of 8% to 12% by weight of the composition.

7. The composition according to claim 6, wherein the polyhexamethylene biguanide is in an amount of 10% to 12% by weight of the composition.

8. The composition according to claim 6, wherein the polyhexamethylene biguanide is in an amount of 8% to 10% by weight of the composition.

9. The composition according to claim 6, wherein the polyhexamethylene biguanide is in an amount of about 10% by weight of the composition.

10. The composition according to claim 6, wherein the polyhexamethylene biguanide is in an amount of 9% to 11% by weight of the composition.

11. The composition according to claim 10, wherein the polyhexamethylene biguanide is in an amount of about 10% by weight of the composition.

12. The composition according to claim 1, wherein the isopropanol is in an amount of 47% to 53% by weight of the composition.

13. The composition according to claim 12, wherein the isopropanol is in an amount of about 49% by weight of the composition.

14. The composition according to claim 12, wherein the isopropanol is in an amount of about 51% by weight of the composition.

15. The composition according to claim 12, wherein the isopropanol is in an amount of about 50% by weight of the composition.

16. A composition consisting of 8% to 12% by weight of the composition of a polyhexamethylene biguanide, 47% to 53% by weight of the composition of an isopropanol, and one or more carriers.

17. The composition according to claim 16, wherein the polyhexamethylene biguanide is in an amount of 9% to 11% by weight of the composition.

18. The composition according to claim 17, wherein polyhexamethylene biguanide is in an amount of about 10% by weight of the composition and the isopropanol is in an amount of about 50% by weight of the composition.

19. A composition consisting of 9% to 11% by weight of the composition a polyhexamethylene biguanide, 47% to 53% by weight of the composition of an isopropanol, and one or more carriers.

20. The composition according to claim 19, wherein polyhexamethylene biguanide is in an amount of about 10% by weight of the composition and the isopropanol is in an amount of about 50% by weight of the composition.

* * * * *